(12) United States Patent
Webber et al.

(10) Patent No.: US 6,977,298 B2
(45) Date of Patent: Dec. 20, 2005

(54) TRICYCLIC INHIBITORS OF POLY(ADP-RIBOSE) POLYMERASES

(75) Inventors: Stephen Evan Webber, San Diego, CA (US); Stacie S. Canan-Koch, La Jolla, CA (US); Jayashree Tikhe, San Diego, CA (US); Lars Henrik Thoresen, College Station, TX (US)

(73) Assignees: Agouron Pharmacetucals, Inc., La Jolla, CA (US); Cancer Research Campaign Technology Limited, London (GB)

( * ) Notice: Subject to any disclaimer, the term of this patent is extended or adjusted under 35 U.S.C. 154(b) by 0 days.

(21) Appl. No.: 11/004,261

(22) Filed: Dec. 3, 2004

(65) Prior Publication Data

US 2005/0085460 A1 Apr. 21, 2005

Related U.S. Application Data

(63) Continuation of application No. 10/264,018, filed on Oct. 2, 2002, now abandoned, which is a continuation of application No. 09/479,896, filed on Jan. 10, 2000, now Pat. No. 6,495,541.
(60) Provisional application No. 60/115,431, filed on Jan. 11, 1999.

(51) Int. Cl.$^7$ .................... C07D 487/06; C07D 471/06; C07D 481/00
(52) U.S. Cl. ......................................... 540/520; 546/84
(58) Field of Search ............................. 540/520; 546/84

(56) References Cited

U.S. PATENT DOCUMENTS

| | | |
|---|---|---|
| 3,642,820 A | 2/1972 | Hester et al. |
| 3,883,590 A | 5/1975 | Schmerling |
| 3,900,477 A | 8/1975 | Philipp et al. |
| 3,932,406 A | 1/1976 | Buttner et al. |
| 3,950,343 A | 4/1976 | Philipp et al. |
| 3,978,066 A | 8/1976 | Philipp et al. |
| 4,033,960 A | 7/1977 | Seng et al. |
| 4,910,193 A | 3/1990 | Buchheit |
| 5,215,738 A | 6/1993 | Lee et al. |
| 5,246,933 A | 9/1993 | Turnbull et al. |
| 5,272,143 A | 12/1993 | Benson et al. |
| 5,342,946 A | 8/1994 | Hamilton |
| 5,587,384 A | 12/1996 | Zhang et al. |
| 5,589,483 A | 12/1996 | West |
| 5,659,082 A | 8/1997 | Flitter et al. |
| 5,756,510 A | 5/1998 | Griffin et al. |
| 5,756,548 A | 5/1998 | Flitter et al. |

FOREIGN PATENT DOCUMENTS

| | | |
|---|---|---|
| EP | 0018493 | 11/1980 |
| EP | 0 525 584 A1 | 7/1992 |
| GB | 2297089 | 7/1996 |
| JP | 57144286 | 9/1982 |
| JP | 6434988 | 2/1989 |
| WO | WO 9509159 | 4/1995 |
| WO | WO 9524379 | 9/1995 |
| WO | WO 9526186 | 10/1995 |
| WO | WO 9704771 | 2/1997 |
| WO | WO 9719934 | 6/1997 |
| WO | WO 9732576 | 9/1997 |
| WO | WO 9833802 | 8/1998 |
| WO | WO 9851307 | 11/1998 |
| WO | WO 9851308 | 11/1998 |
| WO | WO 9911622 | 3/1999 |
| WO | WO 9911623 | 3/1999 |
| WO | WO 9911624 | 3/1999 |
| WO | WO 9911628 | 3/1999 |
| WO | WO 9911644 | 3/1999 |
| WO | WO 9911645 | 3/1999 |
| WO | WO 99/11649 | 3/1999 |
| WO | WO 9959973 | 11/1999 |
| WO | WO 9959975 | 11/1999 |
| WO | WO 99/59975 | 11/1999 |
| WO | WO 97/04771 | 2/2000 |
| WO | WO 01/23386 | 4/2001 |
| WO | WO 01/23390 | 4/2001 |

OTHER PUBLICATIONS

Muchowski, et al., Isocarbostyrils. II. Conversion of 2–methyl–4–acyl–5–nitroisocarbostyrils to 2–substituted indole–4–carboxylic acids, Chemical Abstracts, vol. 75, No. 23, p. 304, 1971.

C.V. Ananthanarayanan, et al., 3,4–Bridged indoles: Part II. Synthesis of 6–keto–1,5–dihydro–45–diazepino '6, 5, 4–cd!indoles and 3,4–disunstituted indoles as 5–HT antagonist, Chemical Abstracts, vol. 88, No. 17, p. 543, 1978.

M. Somei, et al., Azepinoindole derivatives as ergoline alkaloid–type pharmaceuticals, Chemical Abstracts, vol. 111, No. 11, p. 743, 1989.

R.E. Bowman, et al., 1,3,4,5–tetrahydrobenz 'cd!indoles and related compounds. Part II, Journal of the Chemical Society, Perkin transactions 1., pp. 1926–32, 1972.

(Continued)

Primary Examiner—Bruck Kifle
(74) Attorney, Agent, or Firm—Bryan C. Zielinski; Galina M. Yakovleva

(57) ABSTRACT

Compounds of the formula below are poly(ADP-ribosyl) transferase (PARP) inhibitors, and are useful as therapeutics in treatment of cancers and the amelioration of the effects of stroke, head trauma, and neurodegenerative disease.

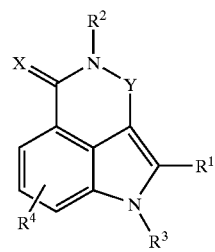

As cancer therapeutics, the compounds of the invention may be used, e.g., in combination with cytotoxic agents and/or radiation.

8 Claims, No Drawings

OTHER PUBLICATIONS

Homing et al., "Isocarbostyrils. II. Conversion of 2–Methyl–4–acyl–5–nitroisocarbostyrils to 2–Substituted indole–4–carboxylic acids," *Canadian Journal of Chemistry*, 49 (17), 2797–2802 (1971).

Clark et al., "1,9–Alkano–Bridged 2,3,4, 5–Tetrahydro–1H–3–benzazepines with Affinity for the $\alpha_2$–Adrenoceptor and the 5–$HT_{1A}$ Receptor," *J. Med. Chem.*, 33, 633–641 (1990).

Santangelo et al., "A Convenient Synthesis of 9–Hydroxy–3, 4,5,6–Tetrahydro–1H–Azepino [5,4,3–cd] Indole from 7–Methoxyindole," *Synthetic Communications*, 23(19), 2717–2725 (1993).

Gmeiner et al., "Synthesis and Dopamine Receptor Binding of 3–Phenylazepino [5,4,3–c,d] indole Derivatives," *Arch. Pharm.*, 328, 329–332 (1995).

Zhang, "PARP Inhibition Results in Substantial Neuroprotection in Cerebral Ischemia," *Cambridge Healthtech Institute's New Therapeutic Opportunities*, Sep. 23–24, Alexis Park Resort, Las Vegas, Nevada (1998).

Saldeen et al., "Nicotinamide–induced apoptosis in insulin producing cells is associated with cleavage of poly (ADP–ribose) polymerase," *Molecular and Cellular Endocrinology*, 139, 99–107 (1998).

Tentori et al., "Role of Wild–Type p53 on the Antineoplastic Activity of Temozolomide Alone or Combined with Inhibitors of Poly(ADP–Ribose) Polyerase," *The Journal of Pharmacology and Experimetal Therapeutics*, 285(2), 884–893 (1998).

Endres et al., "Protective effects of 5–iodo–6–amino–1, 2–benzopyrone, an inhibitor of poly(ADP–ribose) synthetase against peroxynitrite–induced glial damage and stroke development," *European Journal of Pharmacology*, 351, 377–382 (1998).

Pennisi, "A Possible New Partner for Telomerase," *Science*, 282, 1395, 1397 (1998).

Szabo et al., "Protective effect of an inhibitor of poly (ADP–ribose) synthetase in collagen–induced arthritis," *Portland Press Proc.*, 15 (Biology of Nitric Oxide, Part 6), 280 (1998).

Geneste et al., "Recherches en serie de l'imidazo– (4,5, 1–jk)–benzodiazepine–1,4 et de l'imidazo– (1,5,4–ef)—benzodiazepine—1,5," *Eur. J. Med. Chem.*, 13(1), 53–59 (1978); with English abstract.

Endres et al., "Ischemic Brain Injury Is Mediated by the Activation of Poly(ADP–Ribose) Polymerase," *Journal of Cerebral Blood Flow and Metabolism*, 17, 1143–1151 (1997).

Suto et al., "Dihydroisoquinolinones: the design and synthesis of a new series of potent inhibitors of poly (ADP–ribose) polyermase," *Anti Cancer Drug Design*, 7, 107–117 (1991).

Banasik et al., "Specific Inhibitors of Poly (ADP–Ribose0 Synthetase and Mono (ADP–Ribosyl) transferase," *The Journal of Biological Chemistry*, 267(3), 1569–1575 (1992).

Hester, Jr. et al., "Pyrrolo [3,2,1–jk][1,4] benzodiazepines and Pyrrolo [1,2,3–ef][1,5] benzodiazepines Which Have Central Nervous System Activity", *Journal of Medicinal Chemistry*, 13(5), 827–835 (1970).

Smith et al., "Tankyrase, a Poly(ADP–Ribose) Polymerase at Human Telomeres," *Science*, 282, 1484–1487 (1998).

Griffin et al., "Resistance–Modifying Agents. 5. Synthesis and Biological Properties of Quinazololinone Inhibitors of the DNA Repair Enzyme Poly(ADP–ribose) Polymerase (PARP)," *Journal of Medicinal Chemistry*, 5247–5256 (1998).

Bowman et al., "Potentiation of anti–cancer agent cytotoxicity by the potent poly(ADP–ribose) polymerase inhibitors NU1025 and NU1064," *British Journal of Cancer*, 78(10), 1269–1277 (1998).

Denny et al., "Potential Antitumor Agents. 59. Structure–Activity Relationships for 2–Phenylbenzimidazole–4–carboxamides, a New Class of 'Minimal' DNA–Intercalating Agents Which May Not Act via Topoisomerase II," *Journal of Medicinal Chemistry*, 33, 814–819 (1990).

Gilchrist et al., "Cyclisation of *ortho*–Substituted *N*–Arylbenzimidoyl Nitrenes," *J.C.S. Perkin I*, 2303–2307 (1978).

Kubo et al., "Nonpeptide Angiotensin II Receptor Antagonists. Synthesis and Biological Activity of Benzimidazoles," *J. Med. Chem.*, 36, 1772–1784 (1993).

Schneller et al., "Synthesis of *proximal*–Benzoguanine and a Simplified Synthesis of *proximal*–Benzohypoxanthine," *J. Org. Chem.*, 51, 4067–4070 (1986).

Choi, "At the Scene of Ishemic Brain Injury: Is PARP a Perp?," *Nature Medicine*, 3(10), 1073–1074 (1997).

Sculley et al., "The determination of kinetic constants governing the slow, tight–binding inhibition of enzyme–catalysed reactions," *Biochimica et Biophysica Acta*, 874, 44–53 (1986).

Pullen et al., "Chiral separation retention mechanisms in high–performance liquid chromatography using bare silica stationary phase and β–cyclodextrin as a mobile phase additive," *Journal of Chromatography A*, 691, 187–193 (1995).

Pullen et al., "Direct Determination of Substituted Azepinoindole Enantiomers in Rat Plasma Using Silica Stationary Phase and β–Cyclodextrin as a Mobile Phase Additive," *Analytical Chemistry*, 67, 1903–1906 (1995).

Griffin et al., "Novel potent inhibitors of the DNA repair enzyme poly(ADP–ribose) polymerase (PARP)," *Anti–Cancer Drug Design*, 10, 507–514 (1995).

Naidong et al., "Stereospecific determinations of (±)–DU–124884 and its metabolites (±)–KC–9048 in human plasma by liquid chromatography," *Journal of Pharmaceutical and Biomedical Analysis*, 14, 325–337 (1996).

Zingarelli et al., "Protection against myocardial ischemia and reperfusion injury by 3–aminobenzamide, an inhibitor of poly (ADP–ribose) synthetase," *Cardiovascular Research*, 36, 205–215 (1997).

Hayashi et al., "Induction of hepatic poly (ADP–ribose) polymerase by peroxisome proliferators, non–genotoxic hepatocarcinogens," *Cancer Letters*, 127, 1–7 (1998).

Bowes et al., "Effects of inhibitors of the activity of poly (ADP–ribose) synthetase on the liver injury caused by ischaemia–reperfusion: a comparison with radical scavengers," *British Journal of Pharmacology*, 124, 1254–1260 (1998).

Szabo et al., "Role of poly(ADP–ribose) synthetase in inflammation and ischaemia–reperfusion," *TiPS*, 19, 287–298 (1998).

Simonin et al., "Identification of Potential Active–site Residues in the Human Poly (ADP–ribose) Polymerase," *The Journal of Biological Chemistry*, 268(12), 8529–8535 (1993).

Marsischky et al., "Role of Glutamic Acid 988 of Human Poly–ADP–ribose Polymerase in Polymer Formation," *The Journal of Biological Chemistry*, 270(7), 3247–3254 (1995).

Eliasson et al., "Poly (ADP–ribose) polymerase gene disruption renders mice resistant to cerebral ischemia," *Nature Medicine*, 3(10), 1089–1095 (1997).

Cosi et al., "Poly (ADP–ribose) Polymerase (PARP) Revisited, *Annals New York Academy of Sciences*," 366–379 (1997).

Sawant et al., "Synthesis of Some Pentacyclic Quinoxalines," *J. Shivaji Univ. (Science, )*, 17, 63–65 (1977).

Bowman et al., "1,3,4,5–Tetrahydrobenz[cd] indoles and Related Compounds. Part II," *J.C.S. Perkin I*, 1926–1932 (1972).

Ananthanarayanan et al., "3,4–Bridged Indoles: Part II–Synthesis of 6–Keto–1,5–dihydro–4,5–diazepino[6,5,4–*cd*]indoles & 3,4–Disubstituted Indoles as 5–HT Antagonists," *Indian Journal of Chemistry*, 15B, 710–714 (1977).

Segal, *Enzyme Kinetics. Behavior and Analysis of Rapid Equilibrium and Steady–State Enzyme Systems*, ch. 3, John Wiley and Sons, Inc., 100–125 (1975).

Gall et al., "Syntheses of 7–Substituted Indoline Derivatives," *Journal*, 20, 1538–1544 (1955).

Somei et al., "The Chemistry of Indoles. XLIV. Synthetic Study Directed toward 3,4,5,6–Tetrahydro–1H–azepino[5,4, 3–*cd*] indoles," *Chem. Pharm. Bull*, 36(3), 1162–1168 (1988).

Babiychuk et al., "Higher plants possesss two structurally different poly(ADP–ribose) polymerases," *The Plant Journal*, 15(5) 635–645 (1998).

Kawamura et al., "An alternative form of poly(ADP–ribose) polymerase in Drosophila melanogaster and its ectopic expression in rat–1 cells," *Biochemical and Biophysical Research Communication*, 251, 35–40 (1998).

Demerson et al., "Pyrrolo[4,3,2–*de*]isoquinolones with Central Nervous System and Antihypertensive Activities," *Journal of Medicinal Chemistry*, 17(11), 1140–1145 (1974).

Murcia et al., "Poly(ADP–ribose) polymerase: a molecular nick–sensor," *TIBS*, 19, 172–176 (1994).

Bowes et al., "Inhibitors of the activity of poly(ADP–ribose) synthetase reduce the cell death caused by hydrogen peroxide in human cardiac myoblasts," *British Journal of Pharmacology*, 124, 1760–1766 (1998).

Mahajan et al., "Purification and cDNA Cloning of Maize Poly(ADP)–Ribose Polymerase," *Plant Physiol.*, 118, 895–905 (1998).

Zhang, J., "PARP inhibition: a novel approach to treat ischaemia/reperfusion and inflammation–related injuries," *Emerging Drugs: The prospect for Improved Medicines*, 209–221, (1999).

Love et al., "Neuronal accumulation of poly(ADP–ribose) after brain ischaemia," *Neuropathology and Applied Neurobiology*, 25, 98–103 (1999).

Mandir et al., "Poly(ADP–ribose) polymerase activation mediates 1–methyl–4–phenyl–1,2,3,6–tetrahydropyridine (MPTP)–induced parkinsonism," *Proc. Natl. Acad. Sci. USA* 96, 5774–5779 (1999).

Pieper et al., "Poly(ADP–ribose) polymerase, nitric oxide, and cell death," *Trends Pharmacolg. Sci., 20: 171–181* (1999).

Burkart et al., "Mice lacking the poly(ADP–ribose) polymerase gene are resistant to pancreatic beta–cell destruction and diabetes development induced by streptozocin," *Nature Medicine, 5, 314–319 (1999)*.

Kamenka et al., "Syntheses en Serie de la Ceto 6 imidazo [4,5,1–ij] quinoleine," *Chem. 10: 459 (1973)*.

Higgins, J., "Benzimidazole Polymers from Aldehydes and Tetraamines," *Journal of Polymer Science, Part A–I, 8, 171–177 (1970)*.

Imai, Y., "Facile Syntheses of 2H–1,2,4–Benzothiadiazine 1,I–Dioxides and 4–Oxo–3,4–Dihydroquinazolines from 2–Aminobenzenesulfonamide or 2–Aminobeazamide and Aldehydes in the Presence of Sodium Hydrogen Sulfite," *Synthesis, 35–36 (Jan. 1981)*.

Ackerly, N., "A Novel Approach to Dual–Acting Thromboxane Receptor Antagonist/Synthase Inhibitors Based on the Link of 1,3–Dioxane–Thromboxane Receptor Antagonists and Thromboxane Synthase Inhibitors," *J. Med. Chem. 38, 1608–1628 (1995)*.

Breslin et al., "Synthesis and Anti–HIV–1 Activity of 4,5, 6,7–Tetrahydro–5–methylimidazo–[4,5,1–jk][1,4] benzodiazein–2(1H)–one (TIBO) Derivatives," *J. Med. Chem. 38, 771–793 (1995)*.

Szabo et al., "Protection against peroxynitrite–induced fibroblast injury and arthritis development by inhibition of poly(ADP–ribose) synthase," *Proc. Natl. Acad. Sci. USA 95, 3867–3872 (Mar. 1998)*.

Maryanoff et al., "Potential Anxiolytic Agents. Pyrido [1,2–a] benzimidazoles; A New Structural Class of Ligands for the Benzodiazepine Binding Site on GABA–A Receptors," *J. Med. Chem. 38, 16–20 (1995)*.

Prox et al., "Rapid Structure Elucidation of Drug Metabolites by Use of Stable Isotopes," *Xenobiotica, 3(2), 103–112 (1973)*.

US 6,977,298 B2

TRICYCLIC INHIBITORS OF POLY(ADP-RIBOSE) POLYMERASES

This application is a continuation of application Ser. No. 10/264,018, filed Oct. 2, 2002, now abandoned, which is a continuation of application Ser. No. 09/479,896, filed Jan. 10, 2000, now U.S. Pat. No. 6,495,541, which claims the benefit of Provisional Patent Application No. 60/115,431 filed Jan. 11, 1999, which are hereby incorporated by reference in their entireties.

FIELD OF THE INVENTION

The invention pertains to compounds that inhibit poly (ADP-ribose) polymerases, thereby retarding the repair of damage to DNA strands, and to methods of preparing such compounds. The invention also relates the use of such compounds in pharmaceutical compositions and therapeutic treatments useful for potentiation of anti-cancer therapies and inhibition of neurotoxicity consequent to stroke, head trauma, and neurodegenerative diseases.

BACKGROUND OF THE INVENTION

Poly(ADP-ribose) polymerases (PARPs), nuclear enzymes found in almost all eukaryotic cells, catalyze the transfer of ADP-ribose units from nicotinamide adenine dinucleotide ($NAD^+$) to nuclear acceptor proteins, and are responsible for the formation of protein-bound linear and branched homo-ADP-ribose polymers. Activation of PARP and resultant formation of poly(ADP-ribose) can be induced by DNA strand breaks after exposure to chemotherapy, ionizing radiation, oxygen free radicals, or nitric oxide (NO).

Because this cellular ADP-ribose transfer process is associated with the repair of DNA strand breakage in response to DNA damage caused by radiotherapy or chemotherapy, it can contribute to the resistance that often develops to various types of cancer therapies. Consequently, inhibition of PARP may retard intracellular DNA repair and enhance the antitumor effects of cancer therapy. Indeed, in vitro and in vivo data show that many PARP inhibitors potentiate the effects of ionizing radiation or cytotoxic drugs such as DNA methylating agents. Therefore, inhibitors of the PARP enzyme are useful as cancer chemotherapeutics.

In addition, it has been shown that inhibition of PARP promotes resistance to brain injury after stroke (Endres et al., "Ischemic Brain Injury is Mediated by the Activation of Poly(ADP-Ribose)Polymerase," *J. Cerebral Blood Flow Metab.* 17:1143–1151 (1997); Zhang, "PARP Inhibition Results in Substantial Neuroprotection in Cerebral Ischemia," *Cambridge Healthtech Institute's Conference on Acute Neuronal Injury: New Therapeutic Opportunities*, Sept. 18–24, 1998, Las Vegas, Nev.). The activation of PARP by DNA damage is believed to play a role in the cell death consequent to stroke, head trauma, and neurodegenerative diseases. DNA is damaged by excessive amounts of NO produced when the NO synthase enzyme is activated as a result of a series of events initiated by the release of the neurotransmitter glutamate from depolarized nerve terminals (Cosi et al., "Poly(ADP-Ribose) Polymerase Revisited: A New Role for an Old Enzyme: PARP Involvement in Neurodegeneration and PARP Inhibitors as Possible Neuroprotective Agents," *Ann. N.Y. Acad. Sci.*, 366–379). Cell death is believed to occur as a result of energy depletion as $NAD^+$ is consumed by the enzyme-catalyzed PARP reaction. Therefore, inhibitors of the PARP enzyme are useful inhibitors of neurotoxicity consequent to stroke, head trauma, and neurodegenerative diseases.

Further, inhibition of PARP should be a useful approach for treatment of conditions or diseases associated with cellular senescence, such as skin aging, through the role of PARP in the signaling of DNA damage. See, e.g., U.S. Pat. No. 5,589,483, which describes a method to extend the lifespan and proliferative capacity of cells comprising administering a therapeutically effective amount of a PARP inhibitor to the cells under conditions such that PARP activity is inhibited. Hence, inhibitors of the PARP enzyme are useful therapeutics for skin aging.

In yet a further application, PARP inhibition is being explored at the clinical level to prevent development of insulin-dependent diabetes mellitus in susceptible individuals (Saldeen et al., "Nicotinamide-induced apoptosis in insulin producing cells in associated with cleavage of poly (ADP-ribose) polymerase," *Mol. Cellular Endocrinol.* (1998), 139:99–107). PARP inhibitors should therefore be useful as diabetes-prevention therapeutics.

PARP inhibition is also an approach for treating inflammatory conditions such as arthritis (Szabo et al., "Protective effect of an inhibitor of poly(ADP-ribose) synthetase in collagen-induced arthritis," *Portland Press Proc.* (1998), 15:280–281; Szabo, "Role of Poly(ADP-ribose) Synthetase in Inflammation," *Eur. J. Biochem.* (1998), 350(1):1–19; Szabo et al., "Protection Against Peroxynitrite-induced Fibroblast Injury and Arthritis Development by Inhibition of Poly(ADP-ribose) Synthetase," *Proc. Natl. Acad. Sci. USA* (1998), 95(7):3867–72). PARP inhibitors are therefore useful as therapeutics for inflammatory conditions.

Inhibition of PARP has usefulness for protection against myocardial ischemia and reperfusion injury (Zingarelli et al., "Protection against myocardial ischemia and reperfusion injury by 3-aminobenzamide, an inhibitor of poly (ADP-ribose) synthetase," *Cardiovascular Research* (1997), 36:205–215). Therefore, PARP inhibitors are useful in therapy of cardiovascular diseases.

The PARP family of enzymes is extensive. It has recently been shown that tankyrases, which bind to the telomeric protein TRF-1, a negative regulator of telomere length maintenance, have a catalytic domain that is strikingly homologous to PARP and have been shown to have PARP activity in vitro. It has been proposed that telomere function in human cells is regulated by poly(ADP-ribosyl)ation. PARP inhibitors have utility as tools to study this function. Further, as a consequence of regulation of telomerase activity by tankyrase, PARP inhibitors should have utility as agents for regulation of cell life-span, e.g., for use in cancer therapy to shorten the life-span of immortal tumor cells, or as anti-aging therapeutics, since telomere length is believed to be associated with cell senescence.

Competitive inhibitors of PARP are known. For example, Banasik et al. ("Specific Inhibitors of Poly(ADP-Ribose) Synthetase and Mono(ADP-Ribosyl)transferase," *J. Biol. Chem.* (1992) 267: 1569–1575) examined the PARP-inhibiting activity of 132 compounds, the most potent of which were 4-amino-1,8-naphthalimide, 6(5H)-phenanthridone, 2-nitro-6(5H)-phenanthridone, and 1,5-dihydroxyisoquinoline. Griffin et al. reported the PARP-inhibiting activity for a series of benzamide compounds (U.S. Pat. No. 5,756,510; see also "Novel Potent Inhibitors of the DNA Repair Enzyme poly (ADP-ribose)polymerase (PARP)," *Anti-Cancer Drug Design* (1995), 10:507–514) and quinalozinone compounds (International Publication No. WO 98/33802). Suto et al. reported PARP inhibition by a series of dihydroisoquinoline compounds ("Dihydroisoquinolines: The Design and Synthesis of a New Series of Potent Inhibitors of Poly(ADP-ribose) Polymerase," *Anti-Cancer Drug Design* (1991), 7:107–117). Griffin et al. have reported other PARP inhibitors of the quinazoline class ("Resistance-Modifying Agents. 5. Synthesis and Biological Properties of Quinazoline Inhibitors of the DNA Repair Enzyme Poly(ADP-ribose) Polymerase (PARP)," *J. Med. Chem.*, ASAP Article 10.1021/jm980273t S0022-2623(98)00273-8; Web Release Date: Dec. 1, 1998).

Nonetheless, there is still a need for small-molecule compounds that are potent PARP inhibitors, especially those that have physical and chemical properties desirable for pharmaceutical applications.

SUMMARY OF THE INVENTION

The present invention is directed to compounds that function as potent poly(ADP-ribosyl)transferase (PARP) inhibitors and are useful as therapeutics, especially in treatment of cancers and the amelioration of the effects of stroke, head trauma, and neurodegenerative disease. As cancer therapeutics, the compounds of the invention may be used in combination with DNA-damaging cytotoxic agents, for example, topotecan, irinotecan, or temozolomide, and/or radiation.

In particular, the present invention is directed to compounds of the general formula (I):

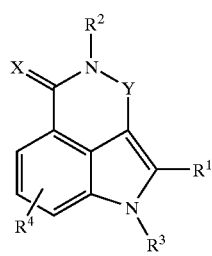

(I)

wherein:
$R^1$ is: H;
halogen;
cyano;
an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, and amino, alkoxy, alkyl, and aryl groups unsubstituted or substituted with one or more substituents selected from halogen, hydroxy, nitro, carboxy, and optionally substituted amino and ether groups (such as O-aryl)); or
—C(O)—$R^{10}$, where $R^{10}$ is: H; an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, amino, and alkyl and aryl groups unsubstituted or substituted with one or more substituents selected from halo, hydroxy, nitro, and amino); or $OR^{100}$ or $NR^{100}R^{110}$, where $R^{100}$ and $R^{110}$ are each independently H or an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, amino, and alkyl and aryl groups unsubstituted or substituted with one or more substituents selected from halogen, hydroxy, nitro, and optionally substituted amino groups);
$R^2$ is H or alkyl;
$R^3$ is H or alkyl;
$R^4$ is H, halogen or alkyl;
X is O or S;
Y is $(CR^5R^6)(CR^7R^8)_n$ or $N=C(R^5)$, where:
n is 0 or 1;
$R^5$ and $R^6$ are each independently H or an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, amino, and lower alkyl, lower alkoxy, or aryl groups unsubstituted or substituted with one or more substituents selected from halogen, hydroxy, nitro, and amino); and
$R^7$ and $R^8$ are each independently H or an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, amino, and lower alkyl, lower alkoxy, and aryl groups unsubstituted or substituted with one or more substituents selected from halogen, hydroxy, nitro, and amino);
where when $R^1$, $R^4$, $R^5$, $R^6$, and $R^7$ are each H, $R^8$ is not unsubstituted phenyl.

The invention is also directed to pharmaceutically acceptable salts, prodrugs, active metabolites, and solvates of such compounds. Preferred compounds of the formula (I) include those where $R^2$ and $R^3$ are each independently selected from H and methyl.

In a preferred embodiment, the inventive compounds include those of generic formula (II):

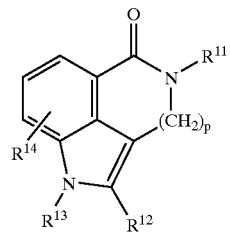

(II)

wherein:
p is 1 or 2;
$R^{11}$ is H or alkyl;
$R^{12}$ is halogen or an optionally substituted aryl, alkyl, alkenyl, alkynyl or acyl group —C(O)—$R^{10}$ as defined above;
$R^{13}$ is H or alkyl; and
$R^{14}$ is H or halogen;
as well as pharmaceutically acceptable salts, prodrugs, active metabolites, and solvates of such compounds.

In preferred compounds of the formula (II), $R^{11}$ and $R^{13}$ are each independently selected from H and methyl. More preferably, the invention is directed to compounds of formula (II) where $R^{11}$ and $R^{13}$ are each H, and $R^{12}$ is optionally substituted aryl, and to pharmaceutically acceptable salts, prodrugs, active metabolites, and solvates of such compounds. In another preferred embodiment of compounds of formula (II), $R^{11}$ and $R^{13}$ are each H, and $R^{12}$ is halogen or optionally substituted aryl.

In another preferred embodiment, the inventive compounds include those of generic formula (III) below, as well as pharmaceutically acceptable salts, prodrugs, active metabolites, and solvates thereof:

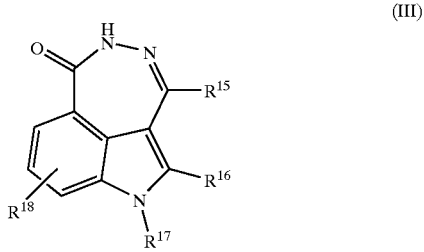

(III)

wherein:
$R^{15}$ is H, halogen, or an alkyl, alkenyl, alkynyl, cycloalkyl, heterocycloalkyl, aryl, or heteroaryl group unsubstituted or substituted with one or more substituents selected from halogen, hydroxy, nitro, amino, and alkyl and aryl groups unsubstituted or substituted with one or more substituents selected from halogen, hydroxy, nitro, and amino;

$R^{16}$ is H; halogen; cyano; or an alkyl, alkenyl, alkynyl, cycloalkyl, heterocycloalkyl, aryl, or heteroaryl group unsubstituted or substituted with one or more substituents selected from halogen, hydroxy, nitro, amino, and alkyl and aryl groups unsubstituted or substituted with one or more substituents selected from halogen, hydroxy, nitro, and amino;

$R^{17}$ is H or alkyl; and
$R^{18}$ is H, halogen, or alkyl;
where $R^{15}$, $R^{16}$, $R^{17}$ and $R^{18}$ are not all H.

In preferred compounds of the formula (III), $R^{15}$ is substituted phenyl or $(CH_2)_q$aryl, where q is 1 or 2.

In other preferred compounds of the formula (III), $R^{16}$ is subsituted or unsubstituted aryl.

The present invention is also directed to a method of inhibiting PARP enzyme activity, comprising contacting the enzyme with an effective amount of a compound of formula (I), (II), or (III), or a pharmaceutically acceptable salt, prodrug, active metabolite, or solvate thereof. The compounds of the invention are potent PARP inhibitors and preferably have a PARP-inhibiting activity corresponding to a $K_i$ of 100 μM or less in the PARP enzyme inhibition assay.

The present invention is further directed to a method of potentiating the cytotoxicity of a cytotoxic drug or ionizing radiation, comprising contacting cells with an effective amount of a compound of formula (I), (II), or (III), or a pharmaceutically acceptable salt, prodrug, active metabolite, or solvate thereof, in combination with a cytotoxic drug or ionizing radiation. The compounds of the invention preferably have a cytotoxicity potentiation activity corresponding to a $PF_{50}$ of at least 1 in the cytotoxicity potentiation assay.

The present invention is also directed to pharmaceutical compositions comprising an effective PARP-inhibiting amount of a compound of formula (I), (II), or (III), or a pharmaceutically acceptable salt, prodrug, active metabolite, or solvate thereof, together with a pharmaceutically acceptable carrier therefor.

The invention also provides therapeutic interventions appropriate in disease or injury states where PARP activity is deleterious to a patient, the therapeutic methods comprising inhibiting PARP enzyme activity in the relevant tissue of the patient by administering a compound of formula (I), (II), or (III), or a pharmaceutically acceptable salt, prodrug, active metabolite, or solvate thereof. In one such therapeutic intervention method provided by the present invention, the effectiveness of a cytotoxic drug or radiotherapy administered to a mammal in the course of therapeutic treatment is improved by administering to the patient, e.g., a mammal in need of treatment, an effective PARP-inhibiting amount of a compound of formula (I), (II), or (III), or a pharmaceutically acceptable salt, prodrug, active metabolite, or solvate thereof, in conjunction with the administration of the cytotoxic drug or radiotherapy.

Another therapeutic intervention method provided by the present invention is for delaying the onset of cell senescence associated with skin aging in a human, comprising administering to fibroblast cells in the human an effective PARP-inhibiting amount of a compound of formula (I), (II), or (III), or a pharmaceutically acceptable salt, prodrug, active metabolite, or solvate thereof.

Yet another therapeutic intervention method provided by the present invention is a method for reducing the neurotoxicity consequent to stroke, head trauma, and neurodegenerative diseases in a mammal by administering an effective amount of a compound of formula (I), (II), or (III), or a pharmaceutically acceptable salt, prodrug, active metabolite, or solvate thereof, to the mammal.

The compounds of the present invention provide a therapeutic approach to treatment of inflammatory conditions, comprising administering an effective amount of a compound of formula (I), (II), or (III), or a pharmaceutically acceptable salt, prodrug, active metabolite, or solvate thereof, to a patient in need of treatment.

Yet a further therapeutic intervention method provided by the present invention is a cardiovascular therapeutic method for protecting against myocardial ischemia and reperfusion injury in a mammal, comprising administering to the mammal an effective amount of a compound of formula (I), (II), or (III), or a pharmaceutically acceptable salt, prodrug, active metabolite, or solvate thereof.

The present invention is further directed to methods of synthesizing the tricyclic compounds of formula (I), wherein a 4-carboalkoxy indole (IV) is converted to an intermediate 3-substituted-4-carboalkoxy indole, thereby incorporating the intended ring carbon atoms, terminally substituted with one nitrogen atom, usually in the form of a nitro group. Additional functional groups, such as formyl or acyl, may be incorporated at the 3-position in this step. The nitro group is reduced to an amine and cyclized upon the 4-carboalkoxy group in an amide-forming reaction to yield the tricyclic heterocycle. The synthetic methods may further comprise derivatization at N-1 and C-2. The 3-formyl or 3-acyl intermediates can be converted to nitrogen-containing intermediates or to tricyclic indoles with N-N bonds, such as the compounds of formula (III).

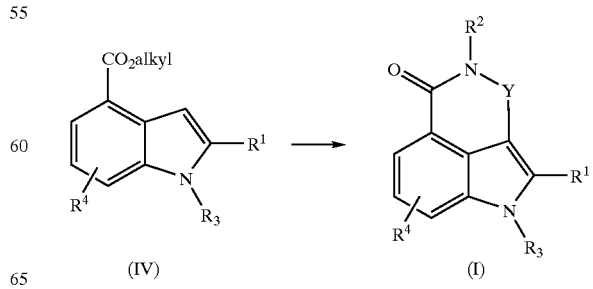

DETAILED DESCRIPTION OF THE INVENTION AND PREFERRED EMBODIMENTS

PARP-Inhibiting Agents:

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

represents a cyclopentyl group, etc.

As used herein, the term "alkyl" means a branched- or straight-chained (linear) paraffinic hydrocarbon group (saturated aliphatic group) having from 1 to 10 carbon atoms in its chain, which may be generally represented by the formula $C_kH_{2k+1}$, where k is an integer of from 1 to 10. Examples of alkyl groups include methyl, ethyl, n-propyl, isopropyl, n-butyl, isobutyl, t-butyl, pentyl, n-pentyl, isopentyl, neopentyl, and hexyl, and the simple aliphatic isomers thereof. A "lower alkyl" is intended to mean an alkyl group having from 1 to 4 carbon atoms in its chain.

The term "alkenyl" means a branched- or straight-chained olefinic hydrocarbon group (unsaturated aliphatic group having one or more double bonds) containing 2 to 10 carbons in its chain. Exemplary alkenyls include ethenyl, 1-propenyl, 2-propenyl, 1-butenyl, 2-butenyl, isobutenyl, and the various isomeric pentenyls and hexenyls (including both cis and trans isomers).

The term "alkynyl" means a branched or straight-chained hydrocarbon group having one or more carbon-carbon triple bonds, and having from 2 to 10 carbon atoms in its chain. Exemplary alkynyls include ethynyl, propynyl, 1-butynyl, 2-butynyl, and 1-methyl-2-butynyl.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

The term "heterocycle" refers to a saturated, partially saturated, unsaturated, or aromatic, monocyclic or fused or non-fused polycyclic, ring structure having one or more heteroatoms selected from N, O, and S. Exemplary heterocycles include heterocycloalkyl, heteroaryl, and heterocycloalkyl-heteroaryl groups.

A "cycloalkyl group" is intended to mean a non-aromatic monovalent, monocyclic or fused polycyclic, ring structure having a total of from 3 to 18 carbon ring atoms (but no heteroatoms). Exemplary cycloalkyls include cyclopropyl, cyclobutyl, cyclopentyl, cyclopentenyl, cyclohexyl, cycloheptyl, adamantyl, phenanthrenyl, and like groups.

A "heterocycloalkyl group" is intended to mean a non-aromatic monovalent, monocyclic or fused polycyclic, ring structure having a total of from 3 to 18 ring atoms, including 1 to 5 heteroatoms selected from nitrogen, oxygen, and sulfur. Illustrative examples of heterocycloalkyl groups include pyrrolidinyl, tetrahydrofuryl, piperidinyl, piperazinyl, morpholinyl, thiomorpholinyl, aziridinyl, and like groups.

The term "aryl" means an aromatic monocyclic or fused polycyclic ring structure having a total of from 4 to 18, preferably 6 to 18, ring carbon atoms (no heteroatoms). Exemplary aryl groups include phenyl, naphthyl, anthracenyl, and the like.

A "heteroaryl group" is intended to mean an aromatic monovalent, monocyclic or fused polycyclic, ring structure having from 4 to 18, preferably 5 to 18, ring atoms, including from 1 to 5 heteroatoms selected from nitrogen, oxygen, and sulfur. Illustrative examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, and the like.

The term "optionally substituted" is intended to indicate that the specified group is unsubstituted or substituted by one or more suitable substituents, unless the optional substituents are expressly specified, in which case the term indicates that the group is unsubstituted or substituted with the specified substituents. Unless indicated otherwise (e.g., by indicating that a specified group is unsubstituted), the various groups defined above may be generally unsubstituted or substituted (i.e., they are optionally substituted) with one or more suitable substituents.

The term "substituent" or "suitable substituent" is intended to mean any substituent for a group that may be recognized or readily selected by the artisan, such as through routine testing, as being pharmaceutically suitable. Illustrative examples of suitable substituents include hydroxy, halogen (F, Cl, I, or Br), oxo, alkyl, acyl, sulfonyl, mercapto, nitro, alkylthio, alkoxy, cycloalkyl, heterocycloalkyl, aryl, heteroaryl, carboxy, amino (primary, secondary, or tertiary), carbamoyl, aryloxy, heteroaryloxy, arylthio, heteroarylthio, and the like (e.g., as illustrated by the exemplary compounds described herein). Suitable substituents are seen from the exemplary compounds that follow.

Preferred optional substituents for alkyl and aryl groups in the compounds of the invention include halogens and aryl groups. Especially preferred for substituted alkyl groups are perfluoro-substituted alkyls. Especially preferred optional substituents for aryl moieties include halogen, lower alkyl, —OH, —$NO_2$, —CN, —$CO_2H$, O-lower alkyl, aryl, —O-aryl, aryl-lower alkyl, —$CO_2CH_3$, —$CONH_2$, —$OCH_2CONH_2$, —$NH_2$, —$SO_2NH_2$, —$OCHF_2$, —$CF_3$, —$OCF_3$, and the like. Aryl moieties may also be optionally substituted by two substituents forming a bridge, for example —O—$(CH_2)_z$—O—, where z is an integer of 1, 2, or 3.

A "prodrug" is intended to mean a compound that is converted under physiological conditions or by solvolysis, or metabolically, to a specified compound that is pharmaceutically active.

An "active metabolite" is intended to mean a pharmacologically active product produced through metabolism in the body of a specified compound.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free-acid or base form of the specified compound and that is pharmaceutically suitable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If an inventive compound is a base, a desired salt may be prepared by any suitable method known in the art, including treatment of the free base with: an inorganic acid, such as hydrochloric acid, hydrobromic acid, sulfuric acid, nitric acid, phosphoric acid, and the like; or with an organic acid, such as acetic acid, maleic acid, succinic acid, mandelic acid, fumaric acid, malonic acid, pyruvic acid, oxalic acid, glycolic acid, salicylic acid, pyranosidyl acid such as glucuronic acid or galacturonic acid; alpha-hydroxy acid such as citric acid or tartaric acid; amino acid such as aspartic acid or glutamic acid; aromatic acid such as benzoic acid or cinnamic acid; sulfonic acid such as p-toluenesulfonic acid or ethanesulfonic acid; or the like.

If an inventive compound is an acid, a desired salt may be prepared by any suitable method known in the art, including treatment of the free acid with an inorganic or organic base, such as an amine (primary, secondary, or tertiary), an alkali metal or alkaline earth metal hydroxide, or the like. Illustrative examples of suitable salts include: organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystalline or polymorph forms, all of which are intended to be within the scope of the present invention and specified formulas.

In some cases, the inventive compounds will have chiral centers. When chiral centers are present, the inventive compounds may exist as single stereoisomers, racemates, and/or mixtures of enantiomers and/or diastereomers. All such single stereoisomers, racemates, and mixtures thereof are intended to be within the broad scope of the generic structural formulae (unless otherwise indicated). Preferably, however, the inventive compounds are used in essentially optically pure form (as generally understood by those skilled in the art, an optically pure compound is one that is enantiomerically pure). Preferably, the compounds of the invention are at least 90% of the desired single isomer (80% enantiomeric excess), more preferably at least 95% (90% e.e.), even more preferably at least 97.5% (95% e.e.), and most preferably at least 99% (98% e.e.).

In some cases, compounds can occur in tautomeric forms. In such cases, it is intended that both tautomers are encompassed by the structural formulae.

The present invention is directed to the following PARP-inhibiting agents: compounds of the formula

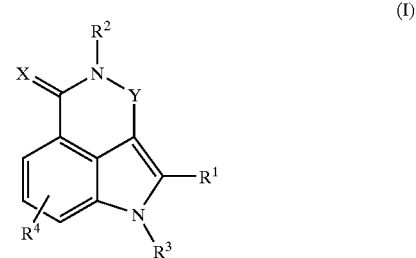

(I)

wherein $R^1$, $R^2$, $R^3$, $R^4$, X, and Y are as defined above; and pharmaceutically acceptable salts, prodrugs, active metabolites, and solvates thereof. In preferred embodiments, the PARP-inhibiting agents are compounds of the formula (I) where $R^2$ and $R^3$ are each independently H or methyl, and pharmaceutically acceptable salts, prodrugs, active metabolites, and solvates thereof.

More preferably, the agents are compounds of formula (II) or (III):

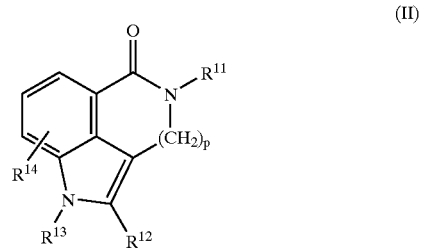

(II)

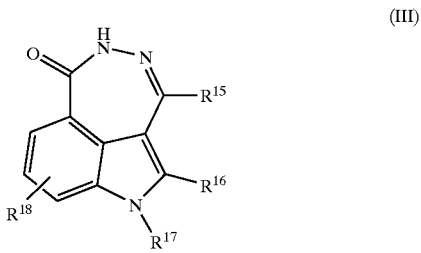

(III)

wherein the variables are as defined above, or pharmaceutically acceptable salts, prodrugs, active metabolites, or solvates thereof. In preferred embodiments for formula (II) and (III), $R^{11}$, $R^{13}$, and $R^{17}$ are each independently H or methyl.

In a preferred embodiment, the inventive agents are compounds of formula (II) and pharmaceutically acceptable salts, prodrugs, active metabolites and solvates, where $R^{11}$ and $R^{13}$ are each H, and $R^{12}$ is an optionally substituted aryl group. In another preferred embodiment, the inventive agents are compounds of formula (III) and pharmaceutically acceptable salts, prodrugs, active metabolites and solvates, where $R^{17}$ is H or methyl and $R^{15}$ is optionally substituted aryl or alkyl.

In other preferred embodiments, $R^{16}$ is substituted or unsubstituted aryl and $R^{15}$ is hydrogen.

In other preferred embodiments, $R^{16}$ is H, and $R^{15}$ is substituted or unsubstituted aryl or alkyl.
Preferred compounds of the invention include:
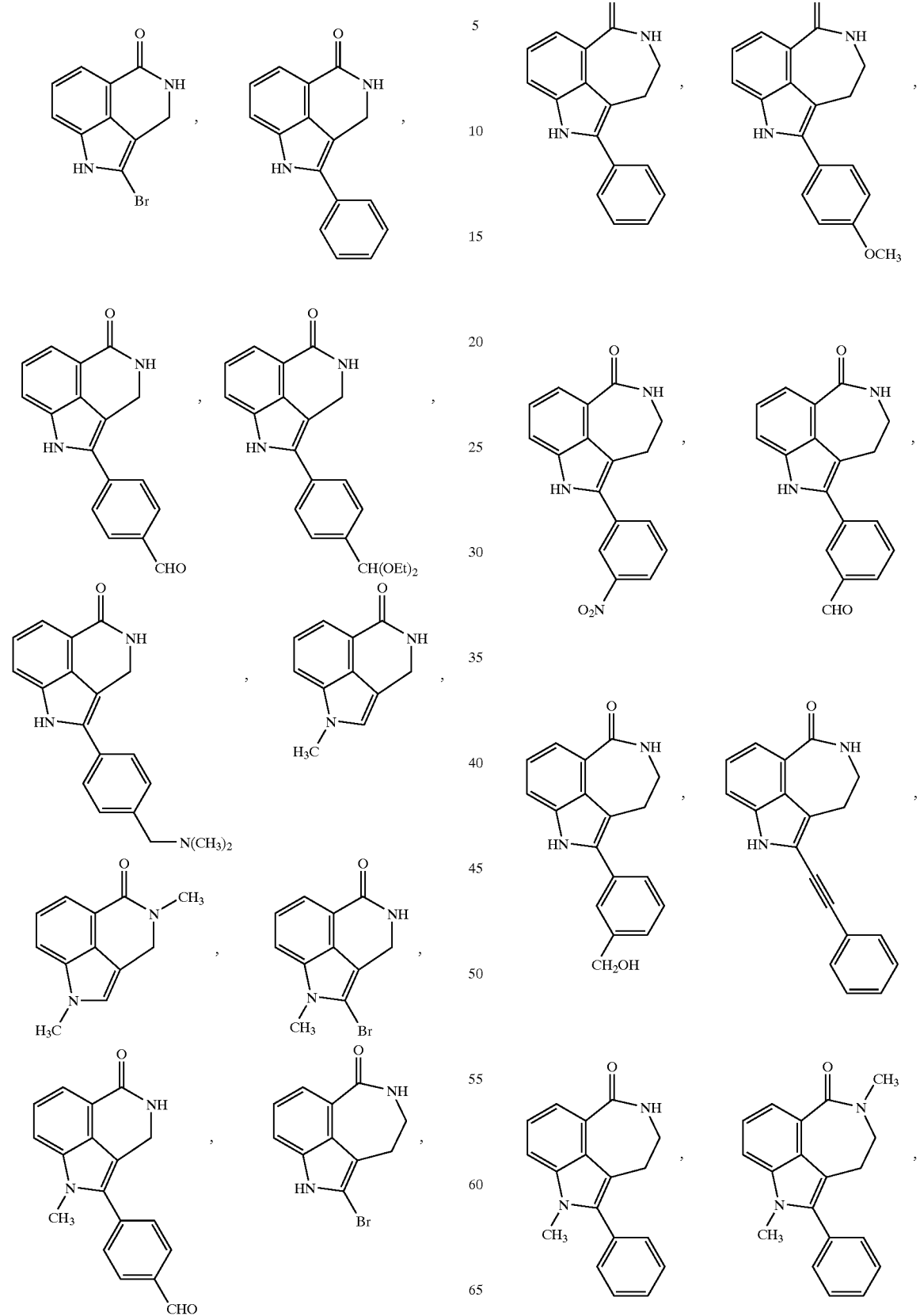

-continued
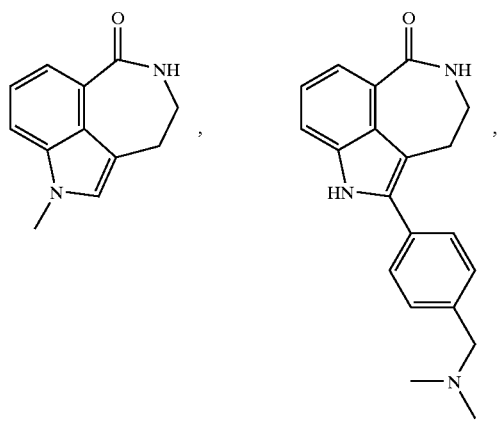
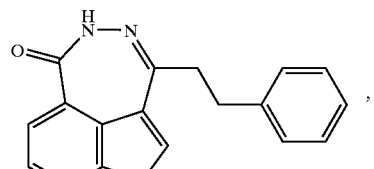
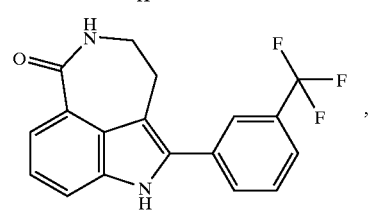
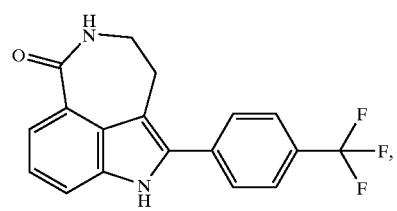
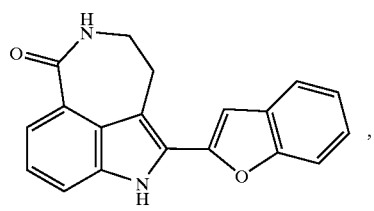
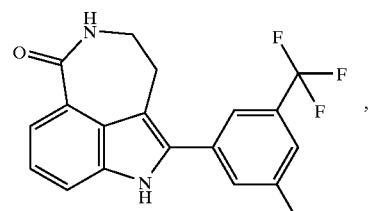
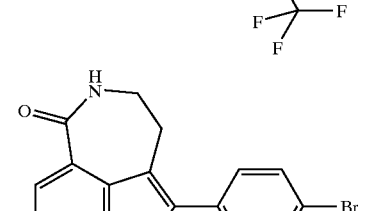
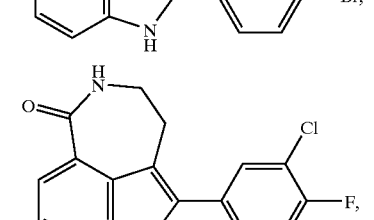
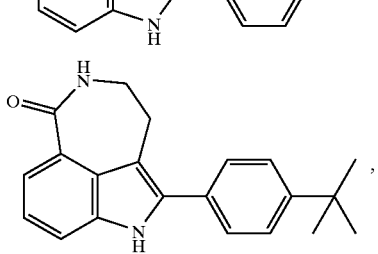

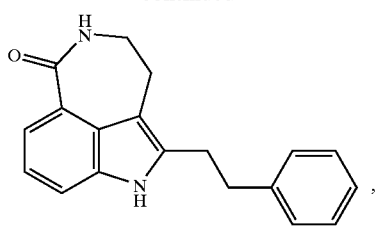,
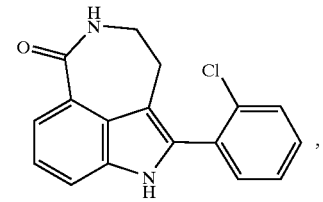,
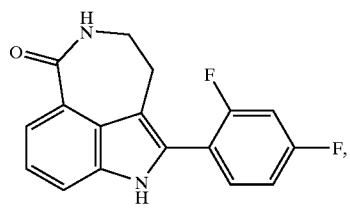,
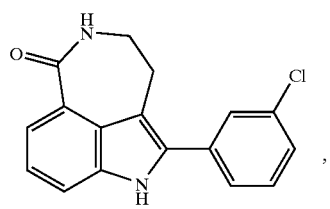,
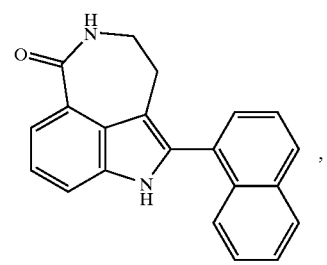,
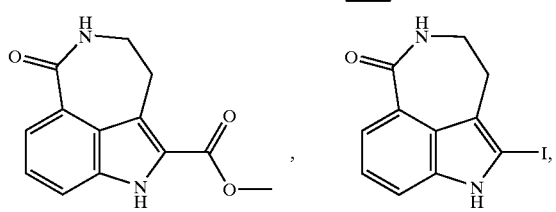,
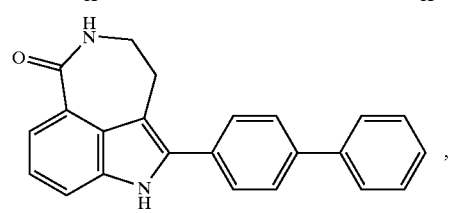,
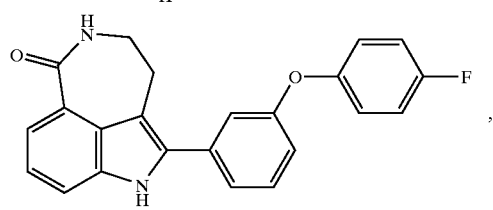,
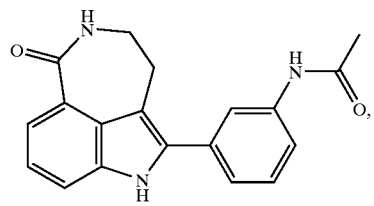,
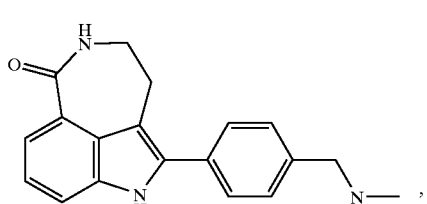,
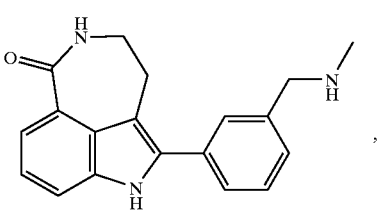,
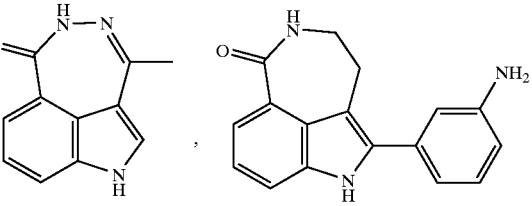,
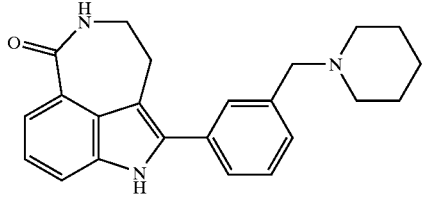,
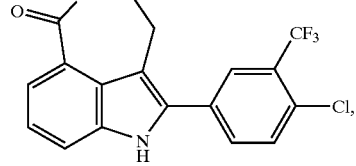,
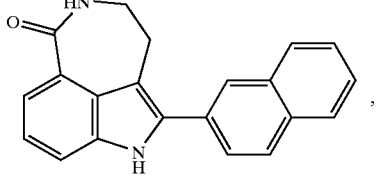,
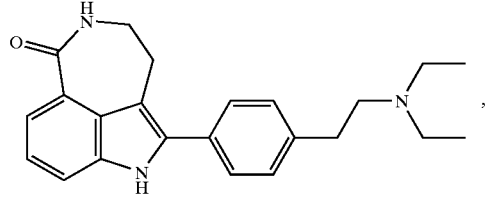,

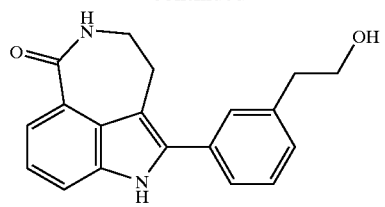,
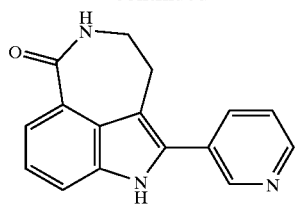,
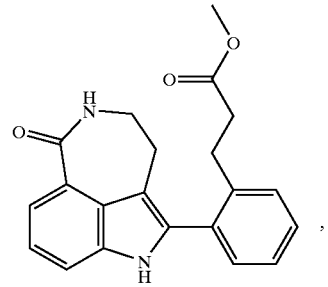,
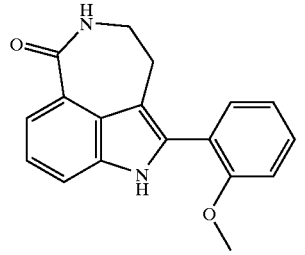,
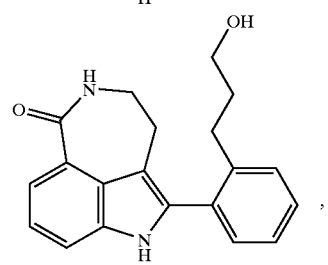,
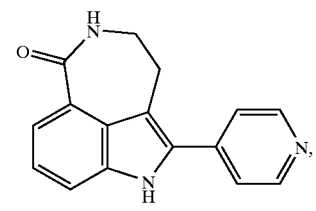,
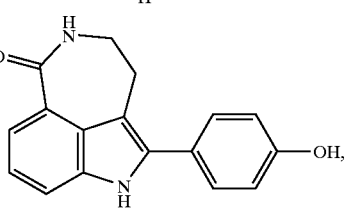,
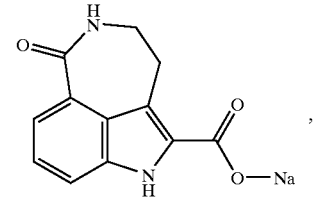,
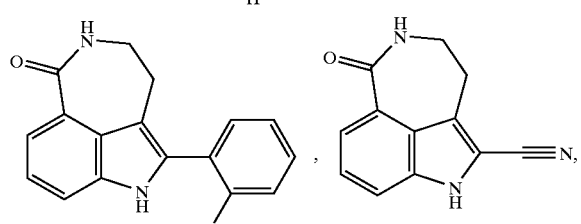,
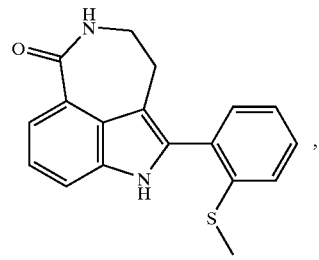,
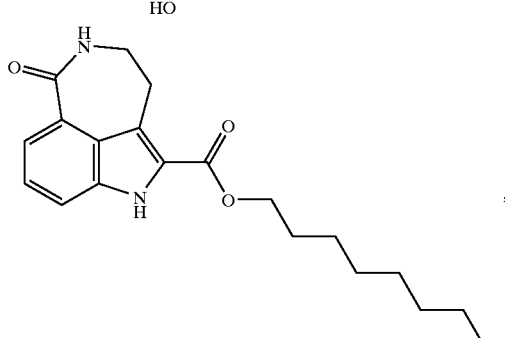,
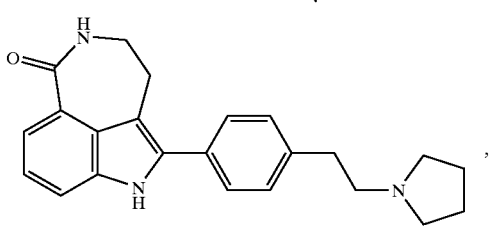,
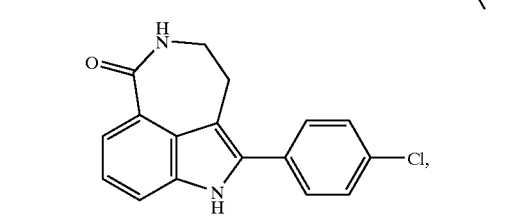,
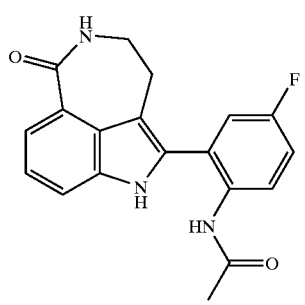, -continued

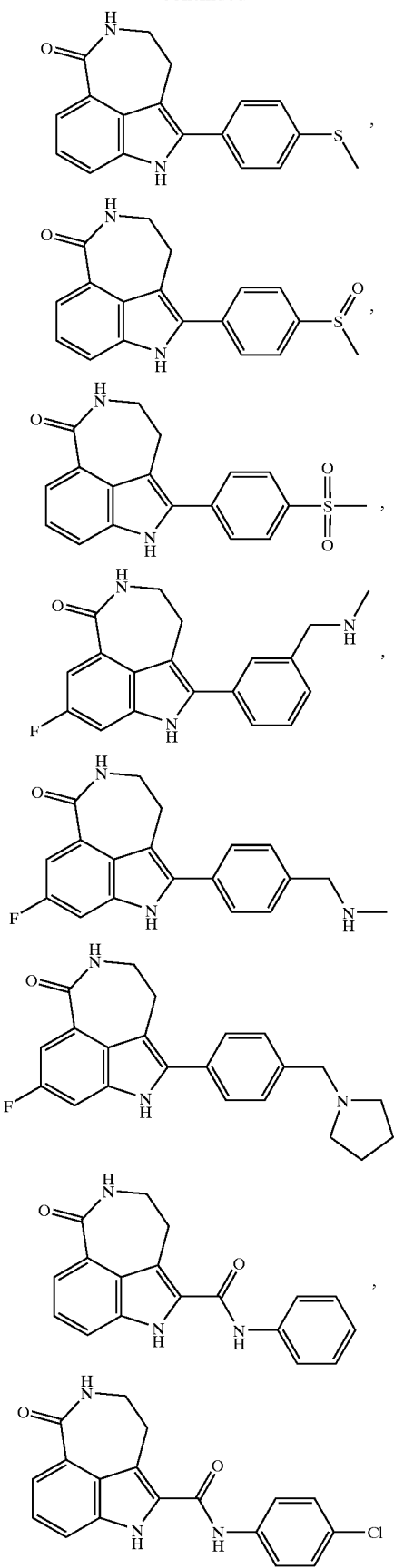
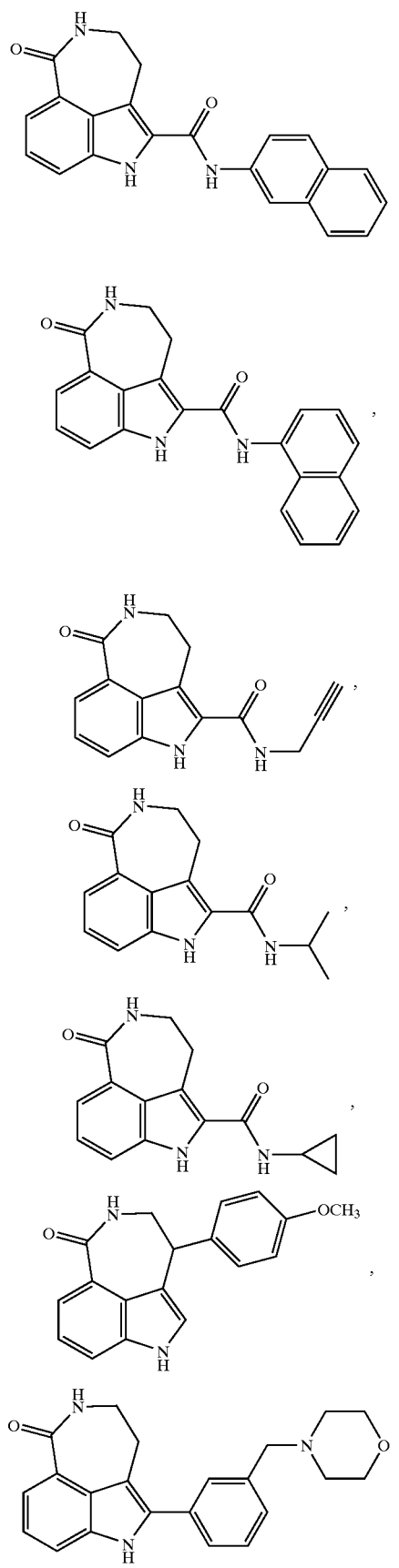

-continued

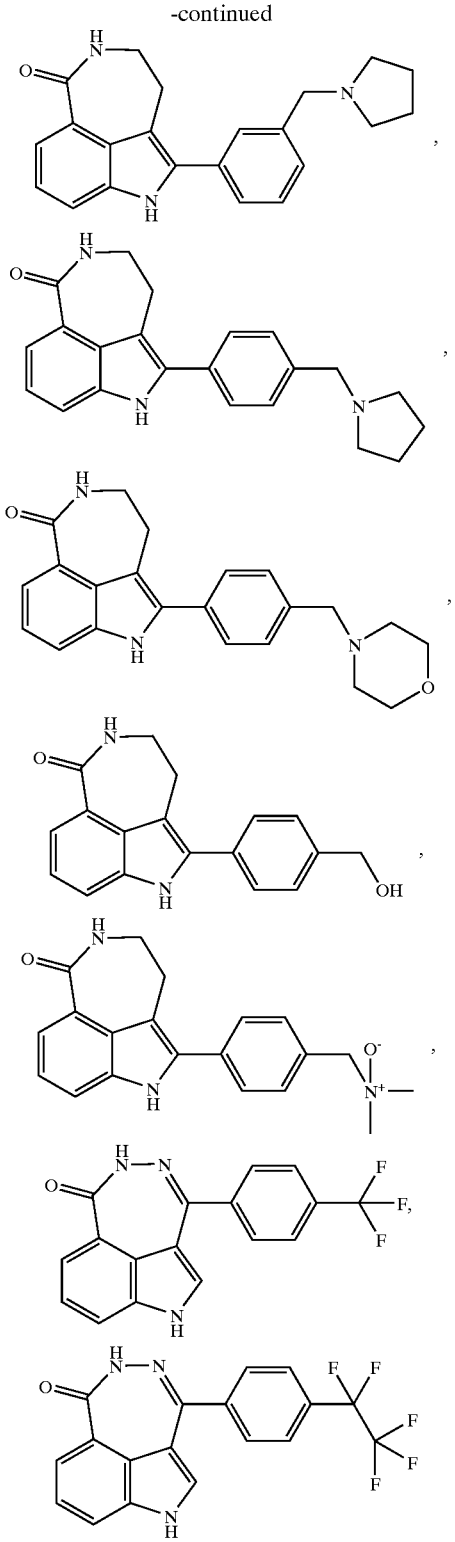

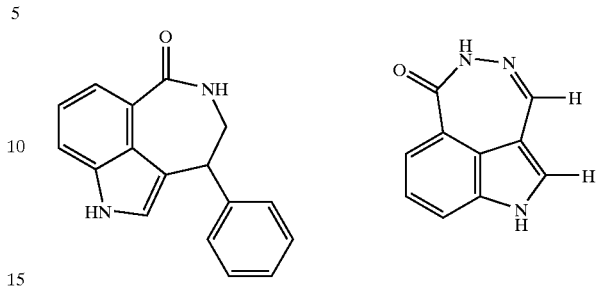

"Treating" or "treatment" is intended to mean mitigating or alleviating an injury or a disease condition in a mammal, such as a human, that is mediated by the inhibition of PARP activity, such as by potentiation of anti-cancer therapies or inhibition of neurotoxicity consequent to stroke, head trauma, and neurodegenerative diseases. Types of treatment include: (a) as a prophylactic use in a mammal, particularly when the mammal is found to be predisposed to having the disease condition but not yet diagnosed as having it; (b) inhibition of the disease condition; and/or (c) alleviation, in whole or in part, of the disease condition.

One treatment method involves improving the effectiveness of a cytotoxic drug or radiotherapy administered to a mammal in the course of therapeutic treatment, comprising administering to the mammal an effective amount of an agent (compound, pharmaceutically acceptable salt, prodrug, active metabolite, or solvate) in conjunction with administration of the cytotoxic drug (e.g., topotecan or irinotecan) or radiotherapy. The PARP-inhibiting agents may also be advantageously used in a method for reducing neurotoxicity consequent to stroke, head trauma, and neurodegenerative diseases in a mammal by administering a therapeutically effective amount of an inventive agent to the mammal. The PARP-inhibiting agents of the invention may also be used in a method for delaying the onset of cell senescence associated with skin aging in a human, comprising administering to fibroblast cells in the human an effective PARP-inhibiting amount of an agent. Further, the agents may also be used in a method for helping prevent the development of insulin-dependent diabetes mellitus in a susceptible individual, comprising administering a therapeutically effective amount of an agent. Additionally, the agents may also be employed in a method for treating an inflammatory condition in a mammal, comprising administering a therapeutically effective amount of an agent to the mammal. Moreover, the agents may also be used in a method for treating cardiovascular disease in a mammal, comprising administering to the mammal a therapeutically effective amount of a PARP-inhibiting agent. As knowledge regarding the therapeutic roles of PARP inhibitors progresses in the art, other utilities of the PARP-inhibiting agents of the invention will become apparent.

The activity of the inventive compounds as inhibitors of PARP activity may be measured by any of the suitable methods known or available in the art, including by in vivo and in vitro assays. An example of a suitable assay for activity measurements is the PARP enzyme inhibition assay described herein.

Administration of the compounds of the formula (I) and their pharmaceutically acceptable prodrugs, salts, active metabolites, and solvates may be performed according to Pharmaceutical Methods and Compositions:

The invention is also directed to a method of inhibiting PARP enzyme activity, comprising contacting the enzyme with an effective amount of a compound of formula (I), or a pharmaceutically acceptable salt, prodrug, active metabolite, or solvate thereof. For example, PARP activity may be inhibited in mammalian tissue by administering a compound of formula (I) or a pharmaceutically acceptable salt, prodrug, active metabolite, or solvate thereof. In addition to the compounds specified above, the following known compounds have been found to be useful for inhibiting PARP enzyme activity:

any of the accepted modes of administration available in the art. Illustrative examples of suitable modes of administration include oral, nasal, parenteral, topical, transdermal, and rectal delivery. Oral and intravenous delivery are preferred.

An inventive compound of formula (I) or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents (including other PARP-inhibiting agents), depending upon the intended use.

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulphate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition contains at least a therapeutically effective amount of a PARP-inhibiting agent (i.e., a compound of formula (I), (II), or (III), or a pharmaceutically acceptable salt, prodrug, active metabolite, or solvate thereof), and preferably contains one or more pharmaceutical dosage units. The selected dose may be administered to a mammal, for example, a human patient, in need of treatment of a condition mediated by inhibition of PARP activity, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an agent that, when administered to a mammal in need thereof, is sufficient to effect treatment for injury or disease condition mediated by inhibition of PARP activity, such as for potentiation of anti-cancer therapies and inhibition of neurotoxicity consequent to stroke, head trauma, and neurodegenerative diseases. The amount of a given compound of the invention that will be therapeutically effective will vary depending upon factors such as the particular compound, the disease condition and the severity thereof, the identity of the mammal in need thereof, which amount may be routinely determined by artisans.

It will be appreciated that the actual dosages of the PARP-inhibiting agents used in the pharmaceutical compositions of this invention will be selected according to the particular complex being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, with courses of treatment repeated at appropriate intervals.

Synthetic Processes:

The present invention is further directed to methods of synthesizing the PARP-inhibiting agents by processes such as those set forth below for exemplary compounds of the invention. In the following examples, the structures of the compounds were confirmed by one or more of the following: proton magnetic resonance spectroscopy, infrared spectroscopy, elemental microanalysis, mass spectrometry, thin layer chromatography, high performance liquid chromatography, and melting point.

Proton magnetic resonance ($^1$H NMR) spectra were determined using a 300 megahertz Tech-Mag, Bruker Avance 300DPX, or Bruker Avance 500 DRX spectrometer operating at a field strength of 300 or 500 megahertz (MHz). Chemical shifts are reported in parts per million (ppm, δ) downfield from an internal tetramethylsilane standard. Alternatively, $^1$H NMR spectra were referenced to residual protic solvent signals as follows: CHCl$_3$=7.26 ppm; DMSO=2.49 ppm; C$_6$HD$_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz (Hz). Infrared absorption (IR) spectra were obtained using a Perkin-Elmer 1600 series or a Midac Corporation FTIR spectrometer. Elemental microanalyses were performed by Atlantic Microlab Inc. (Norcross, Ga.) or Galbraith Laboratories (Nashville, Tenn.), and gave results for the elements stated within ±0.4% of the theoretical values. Flash column chromatography was performed using Silica gel 60 (Merck Art 9385). Analytical thin layer chromatography (TLC) was performed using precoated sheets of Silica 60 F$_{254}$ (Merck Art 5719). Melting points (mp) were determined on a MelTemp apparatus and are uncorrected. All reactions were performed in septum-sealed flasks under a slight positive pressure of argon, unless otherwise noted. All commercial solvents were reagent-grade or better and used as supplied.

The following abbreviations may be used herein: Et$_2$O (diethyl ether); DMF (N,N-dimethylformamide); DMSO (dimethylsulfoxide); MeOH (methanol); EtOH (ethanol); EtOAc (ethyl acetate); THF (tetrahydrofuran); Ac (acetyl); Me (methyl); Et (ethyl); and Ph (phenyl).

The general reaction protocols described below may be used to prepare the compounds of the invention.

General Synthetic Scheme 1:

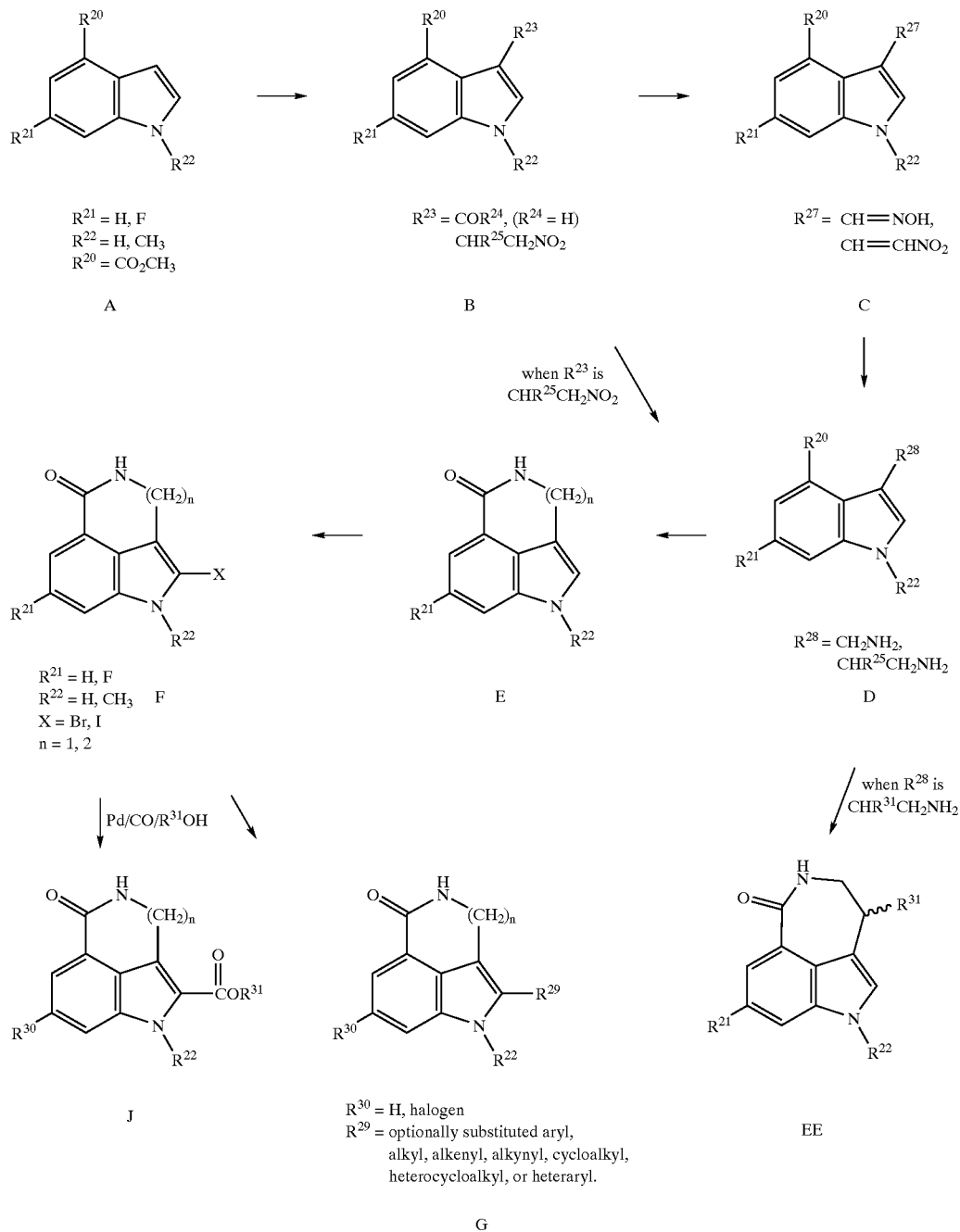

In Scheme 1, 4-carbomethoxyindole A is formylated or acylated under various Vilsmeier or Friedel-Crafts conditions to yield B, where $R^{23}$ is CHO or $COR^{24}$. 4-Carbomethoxyindole A serves as substrate for a 1,4-addition reaction to yield the nitroethyl intermediate B, where $R^{23}$ is $CHR^{25}CH_2NO_2$. Intermediate B, where $R^{23}$ is CHO, is transformed to the corresponding oxime ($R^{27}$ is CH=NOH) or nitroalkene ($R^{27}$ is CH=CHNO$_2$) C, which is then catalytically reduced to the aminoalkyl derivative D. Nitroethyl intermediate B is transformed directly to D (when $R^{23}$ is $CHR^{25}CH_2NO_2$) by reduction in some cases. Compound D spontaneously cyclizes to tricyclic lactams E (n=2) and EE. Exposure of intermediate D to basic conditions also leads to tricyclic lactams E and EE. Compound E is optionally N-alkylated to form N-alkylated E or halogenated to yield F. Intermediate F can be transformed via a metal-catalyzed reaction (typically with palladium as catalyst) into a number of different substituted tricyclic lactams G, where $R^{29}$ is aryl, alkyl, alkenyl or alkynyl. G is optionally further modified at $R^{22}$, $R^{29}$ and $R^{30}$.

Acyl-substituted compounds of formula J (e.g., compound 42) can be made by reaction with CO and the corresponding alcohol with Pd/C catalyst. The esters J may be further converted to other acyl derivatives by hydrolysis to the free acid, followed by activation to —C(O)-Lv, where Lv is a leaving group, by standard methods (e.g., March, *Advanced Organic Chemistry: Reactions, Mechanisms, and Structure,* 4th edition, August 1992, John Wiley & Sons, New York, ISBN 0471601802), and, for example, conversion to amides or other acyl derivatives by reactions generally known in the art. Alternatively, the esters J can be directly converted to amides by standard aminolysis reactions, e.g., by reaction with primary or secondary amines such as dimethylamine or pyrrolidine.

General Synthesis Scheme 2:

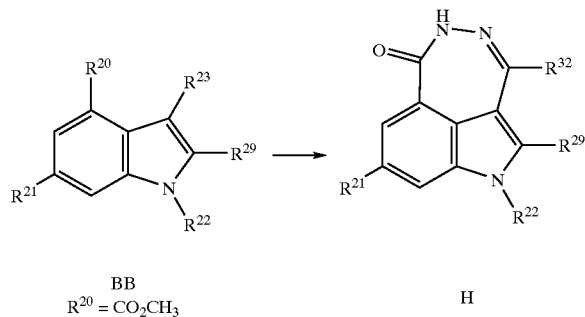

BB
$R^{20} = CO_2CH_3$

H $R^{21}$, $R^{22}$=H
$R^{23}$=COR$^{24}$, ($R^{24}$=H, aryl, (CH)$_q$aryl), q=1 or 2 $R^{32}$=H, aryl, (CH$_2$)$_q$aryl)
$R^{29}$=optionally substituted aryl, alkyl, alkenyl, alkynyl, cycloalkyl, heterocycloalkyl, or heteroaryl, or H.

In Scheme 2, intermediate BB, where $R^{23}$ is CHO, (CO)aryl, or CO(CH$_2$)$_q$aryl where q is 1 or 2, is transformed to tricyclic acyl hydrazone H by reaction with hydrazine.

General Synthetic Scheme 3:

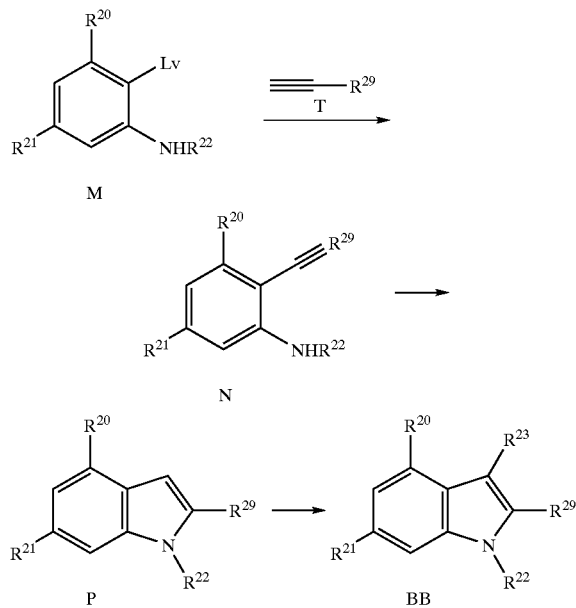

In Scheme 3, the M, where Lv includes, for example, I, Br, or triflate, is coupled with a substituted alkyne T using palladium and copper catalysts (See e.g. Sonogashira, K., Tohda, Y., Hagihara, N. *Tetrahedron Lett.* 1975, 50, 4467–4470, incorporated herein by reference). The intermediate N can be cyclized with palladium catalyst (See e.g. Arcadi, A., Cacchu, S., Marinellito, F. *Tetrahedron Lett.*

1989, 30, 2581–2584, incorporated herein by reference) to give P which is further modified as described in Scheme 1 to the intermediate BB.

EXAMPLES

The invention is further described by reference to the following specific examples. Unless otherwise indicated, all percentages and parts are by weight, and all temperatures are in degrees Celsius.

Example A 3,4-Dihydropyrrolo[4,3,2-de]isoguinolin-5-(1)-one (1)

Compound 1 was prepared as described below according to the procedure of Demerson et al., *J. Med Chem.* (1974), 17:1140, starting from methyl indole-4-carboxylate.

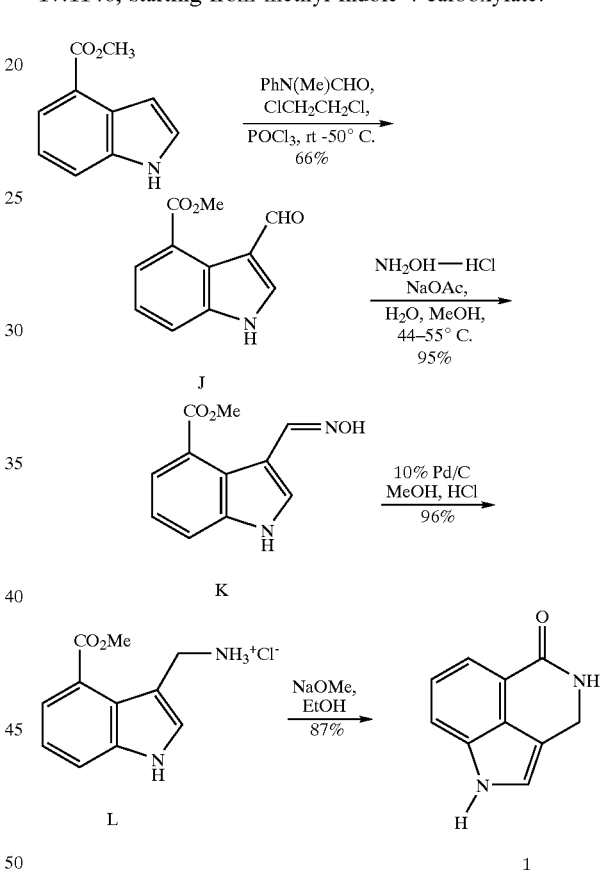

(a) Methyl indole-4-carboxylate:

A solution of methyl 2-methyl-3-nitrobenzoate (9.85 g, 50.5 mmol) and dimethylformamide dimethyl acetal (20.1 mL, 151 mmol) in DMF (53 mL) was heated at 130° C. for 8 hours (h). The solution was concentrated on a high-vacuum rotovap to give the benzoate enamine as a viscous dark-red oil, 12.2 g (97% yield). $^1$H NMR (DMSO-d$_6$) δ 2.83 (s, 6H), 3.85 (s, 3H), 5.42 (d, 1H, J=13.6 Hz), 6.41 (d, 1H, J=13.6 Hz), 7.25 (t, 1H, J=7.9 Hz), 7.76 (d, 1H, J=7.9 Hz), 7.88 (d, 1H, J=7.9 Hz).

A solution of the benzoate enamine (12.2 g, 48.4 mmol) in toluene (200 mL) was treated with 10% palladium-on-carbon (2.7 g), and the mixture was hydrogenated under 50 p.s.i. of hydrogen at room temperature for 1.5 h. The mixture was filtered through a pad of Celite, and the pad was rinsed with EtOAc. The crude product was purified by flash chromatography (3:1 hexanes:EtOAc) to yield methyl indole-4-carboxylate as a yellow solid, 6.89 g (81%). mp 68–70° C.; $^1$H NMR (DMSO-d$_6$) δ 3.95 (s, 3H), 7.02 (s, 1H), 7.25 (t, 1H, J=7.6 Hz), 7.60 (s, 1H), 7.75 (d, 1H, J=7.6 Hz), 7.80 (d, 1H, J=7.6 Hz), 11.54 (bs, 1H).

(b) Intermediate J—methyl 3-formylindole-4-carboxylate:

A solution of methyl indole-4-carboxylate (250 mg, 1.43 mmol) in dichloroethane (2 mL) was treated with a solution of POCl$_3$-DMF (1.5 equivalent (eq)) at room temperature (rt). The orange solution was heated at 50° C. for 1 hour. The reaction solution was poured into ice-cold aqueous (aq.) NaOAc (1g in 2 mL), the aqueous solution was adjusted to pH=8 with 1M NaOH, and extracted with EtOAc (10 mL×3). The organic solution was washed with water and brine, dried (Na$_2$SO$_4$), filtered, and concentrated to give methyl 3-formyl-indole-4-carboxylate as an oil, 271 mg (93%). $^1$H NMR (300 MHz, d$_6$-DMSO) δ 3.68 (s, 3H), 7.16 (t, 1H, J=7.8 Hz), 7.40 (dd, $^1$H, J=7.8, 0.8 Hz), 7.56 (d, 1H, J=7.8, 0.8 Hz), 8.16 (d, 1H, J=3.2 Hz), 10.00 (s, 1H), 12.30 (br s, 1H).

(c) Intermediate K—methyl 3-formylindole-4-carboxylate-oxime:

A mixture of J (2.5 g, 12.3 mmol), N-hydroxylamine hydrochloride (4.27 g, 61.4 mmol), NaOAc (5.04 g, 61.4 mmol), H$_2$O (25 mL), and MeOH (25 mL) was stirred for 1 h at ~50° C. At this time the mixture was cooled to room temperature and concentrated under vacuum to remove the MeOH. Fifty mL of H$_2$O was added, and the solid was filtered and washed with additional H$_2$O. The pure white solid was dried under vacuum at 40° C. (2.57 g, 95%). $^1$H NMR (DMSO-d$_6$) δ 3.88 (s, 3H), 7.23 (t, 1H, J=7.7 Hz), 7.59 (dd, 1H, J=7.4, 1.1 Hz), 7.70 (dd, 1H, J=8.1, 1.1 Hz), 8.01 (s, 1H),8.52(d, 1H, J=3.0Hz), 11.13(s, 1H), 11.97(bs, 1H).

(d) Intermediate L—methyl 3-aminomethylindole-4-carboxylate hydrochloride:

Dry HCl gas was added to a solution of oxime intermediate K (2.4 g, 11 mmol) in 130 mL MeOH. Under an argon atmosphere, 0.2 g of 10% Pd/C was added. Using a three-way valve, the system was evacuated under vacuum. Hydrogen gas was introduced via a balloon, and the reaction mixture was vigorously stirred for 4 h. At this time the balloon was removed, and argon was reintroduced. The mixture was filtered and concentrated to give a solid which became violet in color. The solids were washed with Et$_2$O, protected from air and light, and placed under vacuum at room temperature. The violet solid (2.5 g, 96%) was used without further purification. $^1$H NMR (DMSO-d$_6$) δ 3.89 (s, 3H), 4.31 (m, 2H), 7.23 (t, 1H, J=7.7 Hz), 7.68 (d, 1H, J=2.6 Hz), 7.74 (dd, $^1$H, J=8.1, 1.1 Hz), 7.78 (dd, $^1$H, J=7.2, 1.1 Hz), 8.05 (bs, 3H), 11.92 (bs, 1H).

(e) Compound 1—3,4-dihydropyrrolo[4,3,2-de]isoquinolin-5-(1H)-one:

A solution of intermediate L (2.4 g, 10.0 mmol) in 24 mL absolute EtOH was added to a methanolic solution of NaOMe (0.45 g Na, 24 mL anhydrous MeOH). After stirring at room temperature for 1.5 h, the mixture was concentrated under vacuum to give a residue. With stirring, ice-cold H$_2$O (75 mL) was added to the residue, and the solids were filtered and washed with cold H$_2$O (50 mL). Drying in a vacuum oven at 40° C. afforded 1.51 g (87%) of analytically pure 1 as a tan solid. $^1$H NMR (DMSO-d$_6$) δ 4.78 (s, 2H), 7.14 (t, 1H, J=7.7 Hz), 7.18 (s, 1H), 7.30 (d, 1H, J=7.0 Hz), 7.44 (d, 1H, J=8.1 Hz), 7.59 (s, 1H), 11.13 (bs, 1H); HRMS (M+H) 173.0718; Anal. (C$_{10}$H$_8$N$_2$O.0.2 H$_2$O) C, H, N.

Example B

2-Bromo-3,4-dihydropyrrolo[4,3,2-de]isoquinolin-5-(1H)-one (2)

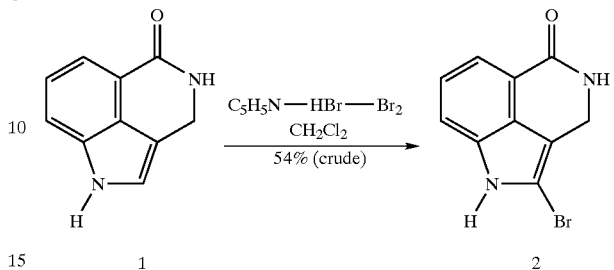

A suspension of Compound 1 (0.086 g, 0.5 mmol) in 40 mL CH$_2$Cl$_2$ was treated with 90% pyridinium tribromide (0.267 g, 0.75 mmol) at 0° C. The reaction mixture was stirred at 0° C. for 30 minutes (min.). The solvent was removed in vacuo, and ice-water was added to the residue. The resulting suspension was stirred vigorously at 0° C. for 30 min. and then filtered, to give 0.068 g (54%) of a brown solid, which was used in the next step without further purification. IR (KBr) 3172, 1655, 1606, 1441, 1367, 1292, 755 cm$^{-1}$; $^1$H NMR (DMSO-d$_6$) δ 4.61 (s, 2H), 7.17 (t, 1H, J=6.0 Hz), 7.32 (d, 1H, J=6.0 Hz), 7.39 (d, 1H, J=6.0 Hz), 7.71 (s, 1H), 11.92 (s, 1H); LRMS (M+H) 251/253.

Example C

Phenyl-3,4-dihydropyrrolo[4,3,2-de]isoquinolin-5-(1H)-one (3)

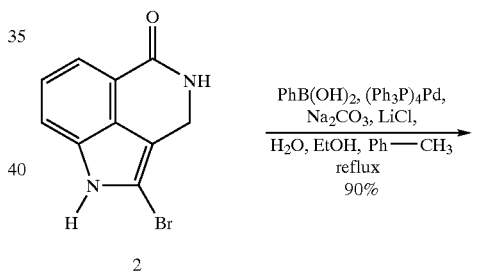

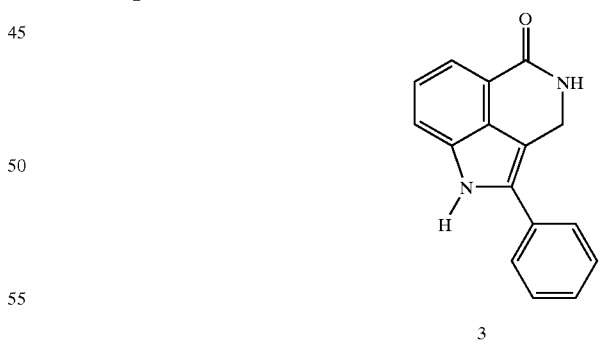

To a suspension of 2 (0.1065 g, 0.424 mmol) in 20 mL toluene/10 mL EtOH was added phenylboronic acid (0.08 g, 0.636 mmol), Na$_2$CO$_3$ (0.113 g, 1.06 mmol) dissolved in a minimum amount of water, LiCl (0.054 g, 1.27 mmol), and tetrakis(triphenylphosphine)palladium(0) (24.5 mg, 21.0 μmol). The reaction mixture was refluxed for 16 h. The solvent was removed in vacuo, and the residue was taken up in EtOAc and washed with saturated aqueous NaHCO$_3$, H$_2$O, and brine. The organic layer was dried over Na$_2$SO$_4$ and concentrated to give a yellow solid, which was purified by flash column chromatography eluting with a gradient of 20% of EtOAc in hexanes to give 0.098 g of a mixture of 3 as a yellow solid. mp 215–218° C. (dec); $^1$H NMR (DMSO-d$_6$) δ 5.04 (s, 2H), 7.17 (t, 1H, J=7.5 Hz), 7.34 (d, 1H, J=6.6 Hz), 7.35 (d, 1H, J=7.4 Hz), 7.50 (m, 4H), 7.66 (d, 1H, J=7.7 Hz), 7.84 (s, 1H), 11.64 (s, 1H); HRMS (M+H) 249.1023.

Example D

Compounds 4 and 5

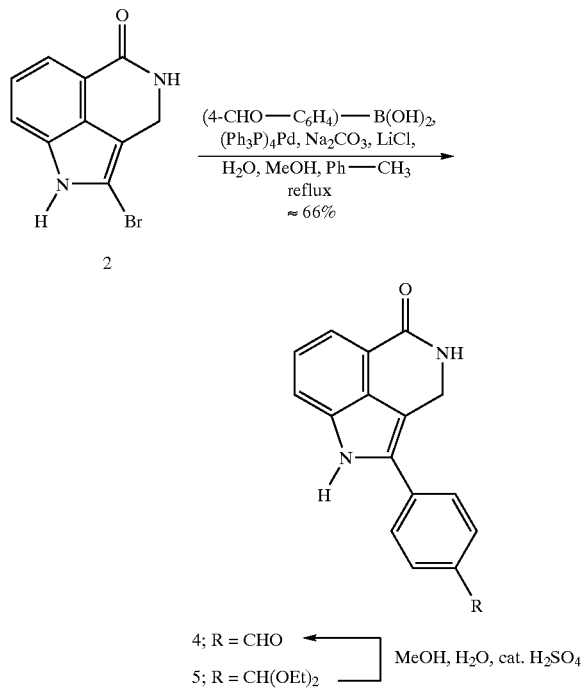

To a suspension of Compound 2 in 30 mL toluene/15 mL EtOH was added 4-formylbenzeneboronic acid (0.457 g, 3.05 mmol), Na$_2$CO$_3$ (0.538 g, 5.08 mmol) dissolved in a minimum amount of water, LiCl (0.258 g, 6.09 mmol), and tetrakis(triphenylphosphine)palladium(0) (0.117 g, 0.102 mmol). The reaction mixture was refluxed for 48 h. The solvent was removed in vacuo, and the residue was taken up in EtOAc and washed with saturated aqueous NaHCO$_3$, H$_2$O , and brine. The organic layer was dried over MgSO$_4$ and concentrated to give a yellow solid, which was purified by flash column chromatography eluting with a gradient of 60–80% of EtOAc in CHCl$_3$ to give 0.370 g of a mixture of 4 and 5. Acetal 5 was converted to the aldehyde 4 using 5 mL MeOH/3 mL H$_2$O and a catalytic amount of conc. H$_2$SO$_4$.

4: IR (KBr) 1694, 1653, 1601, 1261, 821, 746 cm$^{-1}$; $^1$H NMR (DMSO-d$_6$) δ 5.09 (s, 2H), 7.26 (t, 1H, J=6.0 Hz), 7.36 (d, 1H, J=6.0 Hz), 7.50 (d, 1H, J=6.0 Hz), 7.85 (d, 2H, J=9.0 Hz), 7.91 (s, 1H), 8.02 (d, 2H, J=9.0 Hz), 10.01 (s, 1H), 11.86 (s, 1H); LRMS (M+H) 277.

5: $^1$H NMR (DMSO-d$_6$) δ 1.15 (t, 6H, J=6.0 Hz), 3.70 (q, 4H, J=6.0 Hz), 5.03 (s, 2H), 5.51 (s, 1H), 7.20 (t, 1H, J=6.0 Hz), 7.33 (d, 1H, J=6.0 Hz), 7.46 (d, 1H, J=6.0 Hz), 7.51 (d, 2H, J=9.0 Hz), 7.65 (d, 2H, J=9.0 Hz), 7.82 (s, 1H), 11.65 (s, 1H).

Example E

Compound 6

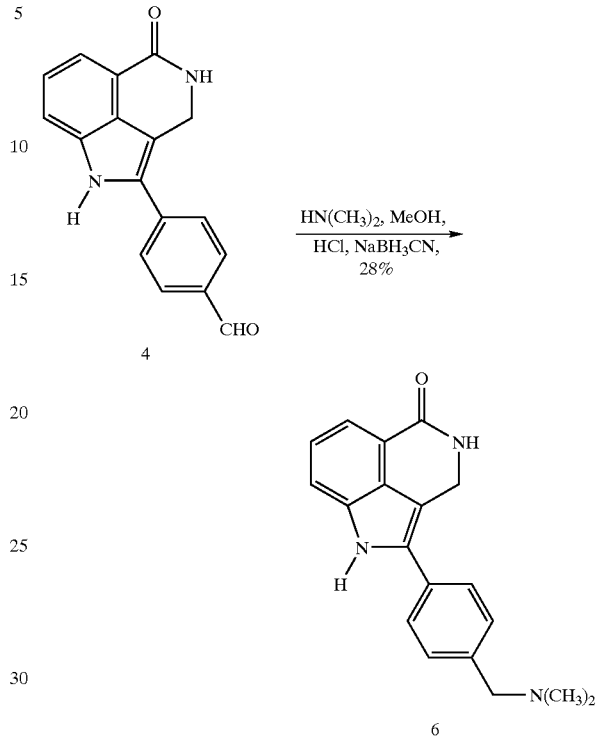

To a solution of 2M (CH$_3$)$_2$NH in MeOH (0.81 mL, 1.61 mmol) was added 5N HCl-MeOH (0.11 mL, 0.536 mmol), followed by a suspension of the aldehyde 4 (0.074 g, 0.268 mmol) in 3 mL MeOH and NaBH$_3$CN (0.017 g, 0.268 mmol). The resulting suspension was stirred for 72 h at room temperature. Concentrated HCl was added until the pH was less than 2, and the MeOH was removed in vacuo. The residue was taken up in H$_2$O and extracted with EtOAc. The aqueous solution was brought to about pH 9 with solid KOH and extracted with EtOAc. The organic layer was dried over MgSO$_4$ and concentrated to give a yellow solid, which was purified by flash silica gel chromatography eluting with a gradient of 3% MeOH in CHCl$_3$ to 10% MeOH/NH$_3$ in CHCl$_3$, to give 0.023 g of an orange solid. $^1$H NMR (DMSO-d$_6$) δ 2.17 (s, 6H), 3.44 (s, 2H), 5.04 (s, 2H), 7.19 (t, 1H, J=6.0 Hz), 7.33 (d, 1H, J=6.0 Hz), 7.42 (d, 1H, J=6.0 Hz), 7.48 (d, 2H, J=9.0 Hz), 7.63 (d, 2H, J=9.0 Hz), 7.81 (s, 1H), 11.62 (s, 1H); LRMS (M+H) 306; Anal. (C$_{19}$H$_{19}$N$_3$O.0.75 H$_2$O) C, H, N.

Example F

Compounds 7 and 7a

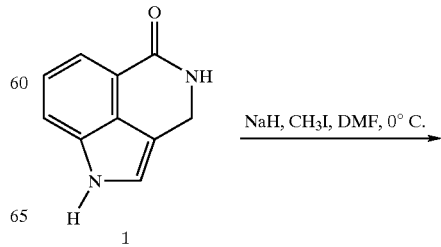

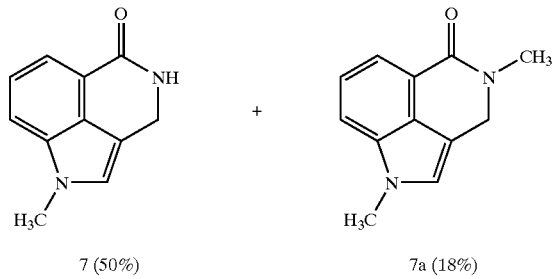

7 (50%)   7a (18%)

Sixty percent sodium hydride (0.267 g, 6.67 mmol) was added to a solution of 1 (0.50 g, 2.9 mmol) in 7 mL DMF at 0° C. The reaction mixture was stirred at 0° C. for 30 min., and then iodomethane (0.18 mL, 2.9 mmol) was added at 0° C. The reaction mixture was allowed to warm to room temperature and stirred for 1.5 h. The solvent was removed in vacuo, and the residue was taken in EtOAc and washed with $H_2O$ and brine. The organic layer was dried over $MgSO_4$ and concentrated to give a brown solid, which was purified by flash silica gel chromatography eluting with a gradient of 0–1% of MeOH in $CHCl_3$ to give 0.270 g (50%) of 7 and 0.104 g (18%) of 7a, both as pale yellow solids.

7: IR (KBr) 3205, 1658, 1610, 1475, 1302, 1280, 817 $cm^{-1}$; $^1$H NMR (DMSO-$d_6$) δ 3.80 (s, 3H), 4.76 (s, 2H), 7.15 (s, 1H), 7.18 (t, 1H, J=6.0 Hz), 7.31 (d, 1H, J=6.0 Hz), 7.51 (d, 1H, J=6.0 Hz), 7.62 (s, 1H); LRMS (M+H) 187.

7a: IR (KBr) 1666, 1618, 1425, 1300, 1272, 1189, 742 $cm^{-1}$; $^1$H NMR (DMSO-$d_6$) δ 3.05 (s, 3H), 3.81 (s, 3H), 4.89 (s, 2H), 7.17–7.22 (m, 2H), 7.35 (d, 1H, J=6.0 Hz), 7.51 (d, 1H, J=6.0 Hz); LRMS (M+H) 201.

Example G

Compound 9

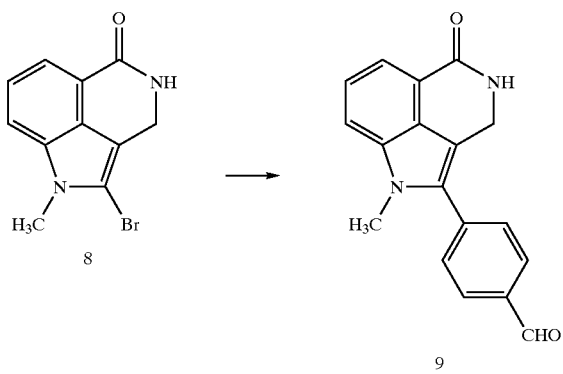

Compound 9 was prepared from bromide 8 using a procedure similar to that described above for preparing Compound 4. IR (KBr) 1699, 1662, 1601, 1466, 1292, 1226 $cm^{-1}$; $^1$H NMR (DMSO-$d_6$) δ 3.82 (s, 3H), 4.88 (s, 2H), 7.30 (t, 1H, J=6.0 Hz), 7.39 (d, 1H, J=6.0 Hz), 7.65 (d, 1H, J=6.0 Hz), 7.78 (s, 1H), 7.82 (d, 2H, J=9.0 Hz), 8.05 (d, 2H, J=9.0 Hz), 10.08 (s, 1H); HRMS (M+H) 291.1130.

Example H 3,4,5,6-tetrahydro-1H-azepino[5,4,3-cd]indol-6-one (10)

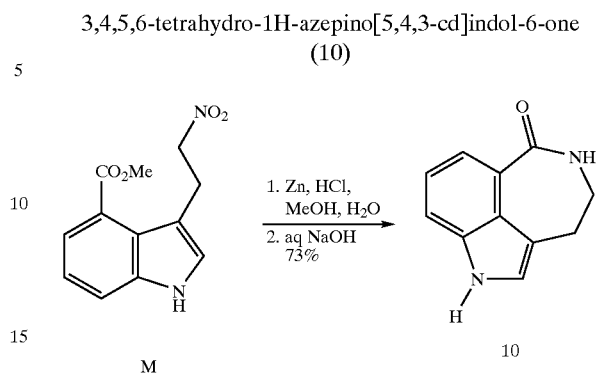

Compound 10 was prepared according to a process generally described by Clark et. al (J. Med. Chem. (1990), 33:633–641) and Somei et. al (Chem. Pharm. Bull. (1988), 36:1162–1168).

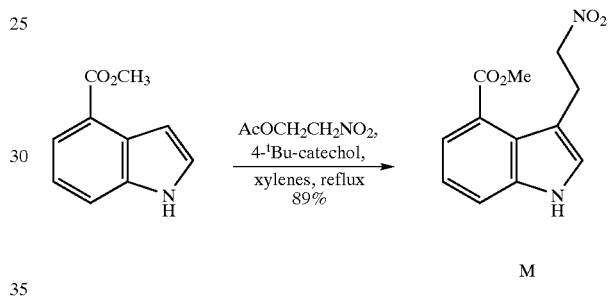

Compound M was first prepared as follows. A solution of methyl indole-4-carboxylate (3.28 g, 18.7 mmol) and nitroethylacetate (2.99 g, 22.5 mmol) in xylenes (23 mL) was treated with 4-t-butylcatechol (22 mg) and heated at reflux for 3.5 h. The solution was allowed to cool to room temperature and the solvent removed under reduced pressure. The residue was purified by flash chromatography (3:1 hexanes:EtOAc), to give a pale-yellow solid, 4.13 g (89%). mp 101–102° C.; $^1$H NMR (DMSO-$d_6$) δ 3.54 (t, 2H, J=7.0 Hz), 3.93 (s, 3H), 4.79 (t, 2H, J=7.0 Hz), 7.23 (m, 2H), 7.43 (s, 1H), 7.66 (m, 2H), 11.49 (bs, 1H); HRMS (M+H) Calcd for $C_{12}H_{12}N_2O_4$+H: 249.0875, Found: 249.0870.

Intermediate M (1.12 g, 4.53 mmol) was dissolved in MeOH (70 mL) by gently heating. Aqueous 2M HCl (70 mL) was added. With vigorous stirring, 7.0 g of zinc dust was added portionwise, and the resulting mixture was heated at reflux for 30 min. The hot reaction mixture was filtered; the filtrate was treated with aqueous 2M NaOH (85 mL), and the resulting mixture was filtered through a paper-lined Buchner funnel. The filter cake was rinsed with MeOH. The MeOH was removed under reduced pressure, and the aqueous mixture was extracted with EtOAc (2×100 mL). The organic solution was washed with water and brine, dried ($Na_2SO_4$), filtered, and concentrated. The crude product was crystallized with $CH_2Cl_2$/MeOH to give the tricycle as a yellow solid, 611 mg (73%). mp 234–236° C.; $^1$H NMR (DMSO-$d_6$) δ 2.55 (m, 2H), 2.98 (m, 2H), 7.22 (t, 1H, J=7.7 Hz), 7.3 (s, 1H), 7.58 (d, 1H, J=7.7 Hz), 7.70 (d, 1H, J=7.7Hz), 8.04 (bt, 1H), 11.17 (bs, 1H); Anal. ($C_{11}H_{10}N_2O$) C, H, N.

Example I

2-Bromo-3,4,5,6-tetrahydro-1H-azepino[5,4,3-cd]indol-6-one (11)

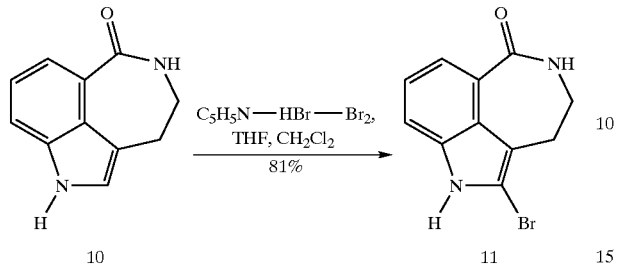

Compound 10 (264 mg, 1.42 mmol) in CH$_2$Cl$_2$ (30 mL) and THF (30 mL) was treated with pyridinium tribromide (0.534 g, 1.67 mmol) at 0° C. The orange solution was stirred for 10 min., and then allowed to warm to ambient temperature and stirred for an additional hour. Water (30 mL) was added, and the organic solvents were removed in vacuo. The aqueous solution was adjusted to pH=8–9 with 1M NaOH and extracted with CH$_2$Cl$_2$ (3×30 mL). The organic solution was washed with water and brine, dried (Na$_2$SO$_4$), filtered, and concentrated. The crude product was recrystallized (CH$_2$Cl$_2$/MeOH) to yield the tricyclic bromide as a yellow solid, 305 mg (81%). mp 204–206° C. (dec); $^1$H NMR (DMSO-d$_6$) δ 2.85 (m, 2H), 3.45 (m, 2H), 7.25 (t, 1H, J=7.8 Hz), 7.52 (d, 1H, J=7.8 Hz), 7.72 (d, 1H, J=7.8 Hz), 8.14 (bt, 1H), 12.05 (bs, 1H); HRMS (M+H) Calcd for C$_{11}$H$_9$BrN$_2$O+H: 264.9976, Found: 264.9984.

Example J

2-Phenyl-3,4,5,6-tetrahydro-1H-azepino[5,4,3-cd]indol-6-one (12)

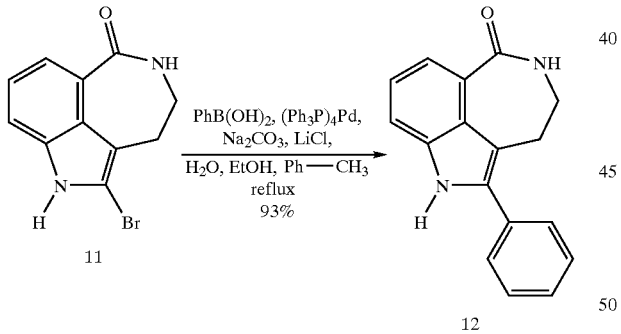

Tricyclic bromide 11 (0.2 g, 0.75 mmol) in toluene (20 mL) and EtOH (10 mL) was treated with solid Na$_2$CO$_3$ (0.199 g, 1.88 mmol), LiCl (0.095 g, 2.25 mmol), phenylboronic acid (0.138 g, 1.13 mmol), and water (0.50 mL). The solution was degassed and tetrakis(triphenylphosphine)palladium(0) (43 mg, 5 mol %) was added. The solution was heated at reflux for 5 h, and then cooled to ambient temperature and diluted with water (20 mL). The aqueous layer was adjusted to pH=7–8 with saturated aqueous K$_2$CO$_3$ and extracted with EtOAc (20 mL×3). The organic solution was washed with water and brine, and dried (Na$_2$SO$_4$), filtered, and concentrated. The crude product was recrystallized (CH$_2$Cl$_2$/MeOH/hexanes) to yield the 2-phenyltricycle as a pale-yellow solid, 183 mg (93%). mp 249–255° C. (dec); $^1$H NMR (CDCl$_3$/CD$_4$OD) δ 3.14 (m, 2H), 3.53 (m, 2H), 7.23 (t, 1H, J=7.7 Hz), 7.33 (m, 1H), 7.44 (m, 2H), 7.55 (m, 3H), 7.83 (d, 1H, J=7.7 Hz); HRMS (M+H) Calcd for C$_{17}$H$_{14}$N$_2$O+H: 263.1184, Found: 263.1189; Anal. (C$_{17}$H$_{14}$N$_2$O.0.8 H$_2$O) C, H, N.

Example K 2-(4-Methoxyphenyl)-3,4,5,6-tetrahydro-1H-azepino[5,4,3-cd]indol-6-one (13)

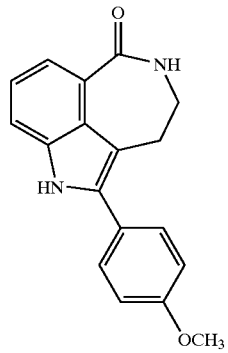

(13)

Tricyclic bromide 11 (48 mg, 0.18 mmol) in toluene (5 mL) and EtOH (2.5 mL) was treated with solid Na$_2$CO$_3$ (48 mg, 0.45 mmol), LiCl (23 mg, 0.54 mmol), p-methoxyphenylboronic acid (41 mg, 0.27 mmol), and water (0.25 mL). The solution was degassed, and tetrakis(triphenylphosphine)palladium(0) (10 mg, 5 mol %) was added. The solution was heated at reflux for 13 h, and then cooled to ambient temperature and diluted with water (10 mL). The aqueous layer was adjusted to pH=7–8 with saturated aqueous K$_2$CO$_3$ and extracted with EtOAc (10 mL×3). The organic solution was washed with water and brine, dried (Na$_2$SO$_4$), filtered, and concentrated. The crude product was recrystallized (MeOH/THF) to yield the 2-(p-methoxyphenyl)tricycle as a white solid, 47.4 mg (89%). mp 143–148° C. (dec); $^1$H NMR (DMSO-d$_6$) δ 3.08 (m, 2H), 3.38 (m, 2H), 3.87 (s, 3H), 7.14 (d of ABq, 2H, J=8.6 Hz), 7.22 (t, 1H, J=7.5 Hz), 7.57 (d, $^1$H, J=7.5 Hz), 7.64 (d of ABq, 2H, J=8.6 Hz), 7.70 (d, $^1$H, J=7.5 Hz,), 8.11 (bt, 1H), 11.52 (bs, 1H); HRMS (M+H) Calcd for C$_{18}$H$_{16}$N$_2$O$_2$+H: 293.1290, Found: 293.1301; Anal. (C$_{18}$H$_{16}$N$_2$O$_2$) C, H, N.

Example L 2-(3-Nitrophenyl)-3,4,5,6-tetrahydro-1H-azepino[5,4,3-cd]indol-6-one (14)

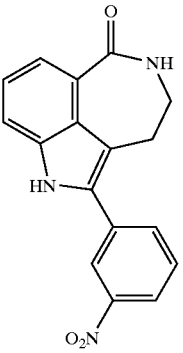

(14)

Tricyclic bromide 11 (27 mg, 0.10 mmol) in 1,4-dioxane (1.0 mL) was treated with solid K$_2$CO$_3$ (41 mg, 0.30 mmol), m-nitrophenylboronic acid (34 mg, 0.20 mmol), and water (0.25 mL). The solution was degassed and tetrakis (triphenylphosphine)palladium(0) (12 mg, 10 mol %) was added. The solution was heated at 100° C. for 1 h, then cooled to ambient temperature and diluted with water (2 mL). The aqueous layer was adjusted to pH=7–8 with saturated aqueous $K_2CO_3$ and extracted with EtOAc (5 mL×3). The organic solution was washed with water and brine, dried ($Na_2SO_4$), filtered, and concentrated. The crude product was purified by flash chromatography (3–5% MeOH in $CHCl_3$) to yield 14 as a yellow solid, 26.3 mg (87%). mp 268–270° C. (dec.); $^1H$ NMR (DMSO-$d_6$) δ 3.16 (m, 2H), 3.45 (m, 2H), 7.33 (m, 1H), 7.65 (m, 1H), 7.76 (m, 1H), 7.78 (m, 1H), 8.30 (m, 1H), 8.53 (bs, 1H), 8.16 (m, 2H), 11.93 (bs, 1H); HRMS (M+Na) Calcd for $C_{17}H_{13}N_3O_3$+Na: 330.0855, Found: 330.0847; Anal. ($C_{17}H_{13}N_3O_3 \cdot H_2O$) C, H, N.

Example M 2-(3-Hydroxymethylphenyl)-3,4,5,6-tetrahydro-1H-azepino[5,4,3-cd]indol-6-one (16)

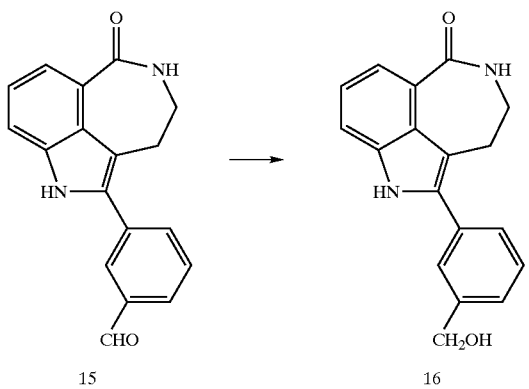

In a manner similar to that described above for Compound 12, the tricyclic bromide (381 mg, 1.44 mmol) and 3-formylbenzeneboronic acid (345 mg, 2.16 mmol) were coupled to yield 2-(3-formylphenyl)-3,4,5,6-tetrahydro-1H-azepino[5,4,3-cd]indol-6-one 15, 346 mg (83%), as a tan solid. $^1H$ NMR (300 MHz, $d_6$-DMSO) δ 2.86 (m, 2H), 3.16 (m, 2H), 7.01 (t, 1H, J=7.8 Hz), 7.34 (d, 1H, J=7.3 Hz), 7.50 (m, 2H), 7.73 (m, 2H), 7.85 (br t, 1H), 7.94 (s, 1H), 9.88 (s, 1H), 11.50 (br s, 1H).

Compound 16 was isolated as a by-product from the reductive amination of 15 with dimethylamine and sodium cyanoborohydride, and recrystallized ($CH_2Cl_2$/hexanes), to give a pale-yellow solid. mp 258–259° C. (dec); $^1H$ NMR (DMSO-$d_6$) δ 3.11 (m, 2H), 3.43 (m, 2H), 4.64 (d, 2H, J=5.5 Hz), 5.36 (t, 1H, J=5.5 Hz), 7.26 (t, 1H, J=7.6 Hz), 7.41 (m, 1H), 7.56 (m, 3H), 7.66 (m, 1H), 7.73 (d, 1H, J=7.6 Hz), 8.14 (m, 1H), 11.64 (bs, 1H); Anal. ($C_{18}H_{18}N_2O_2 \cdot 0.25 H_2O$) C, H, N.

Example N 2-(Phenylethynyl)-3,4,5,6-tetrahydro-1H-azepino[5,4,3-cd]indol-6-one (17)

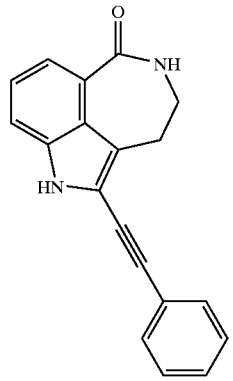

Tricyclic bromide 11 (58.6 mg, 0.22 mmol) in DMF (1 mL) was degassed and treated with tributyl(phenylethynyl)tin (95.2 mg, 0.24 mmol) and tetrakis(triphenylphosphine)palladium(0) (13 mg, 2 mol %). One crystal of 2,6-di-t-butyl-4-methyl phenol was added, and the solution was heated at 60° C. for 10 h. Starting material was still present, so the solution was heated at 100° C. for an additional 2 h. The reaction mixture was cooled to ambient temperature and diluted with water (2 mL) and extracted with EtOAc (5 mL×3). The organic solution was washed with water and brine, dried ($Na_2SO_4$), filtered, and concentrated. The crude product was purified by radial chromatography (2 mm $SiO_2$; 3% MeOH in $CH_2Cl_2$) to yield 17 as a white solid (34.8 mg, 55%). mp 255–256° C. (dec); $^1H$ NMR (DMSO-$d_6$) δ 11.86 (s, 1H), 8.17 (m, 1H), 7.75 (d, 1H, J=7.6 Hz), 7.63 (m, 3H), 7.51 (m, 3H), 7.33 (t, 1H, J=7.6 Hz), 3.50 (m, 2H), 3.09 (m, 2H); HRMS (FAB, M+H) Calcd for $C_{19}H_{14}N_2O$+H: 287.1184, Found: 287.1192; Anal. ($C_{19}H_{14}N_2O \cdot 0.6 H_2O$) C, H, N.

Example O

1-Methyl-2-phenyl-3,4,5,6-tetrahydro-1H-azepino[5,4,3-cd]indol-6-one (18)

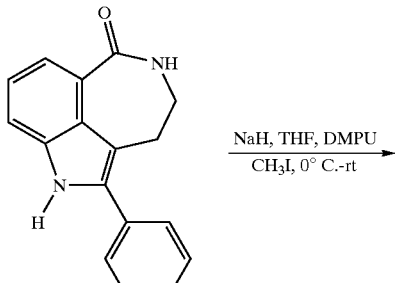

-continued

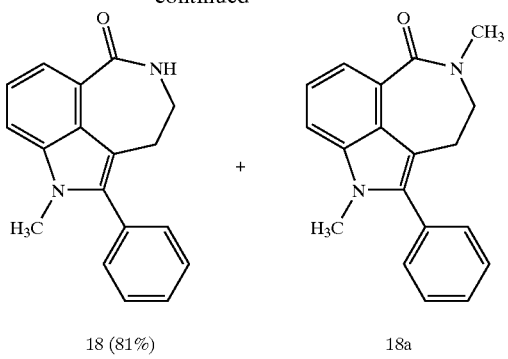

18 (81%)        18a

A solution of compound 12 (51.3 mg, 0.20 mmol) in THF (1 mL) and 0.1 mL 1,3-dimethyl-3,4,5,6-tetrahydro-2(1H)-pyrimidinone (DMPU) was cooled with an ice/water bath and treated dropwise with a suspension of NaH (0.45 mmol) in THF (0.5 mL). The yellow mixture was allowed to stir at 0° C. for 10 min., and was treated dropwise with a 1M solution of iodomethane in THF (0.22 mL, 0.22 mmol). The mixture was allowed to warm to ambient temperature and stirred for 30 min. The reaction was quenched at 0° C. with saturated aqueous $NH_4Cl$, and extracted with EtOAc (5 mL×3). The organic solution was washed with water and brine, dried ($Na_2SO_4$), filtered, and concentrated. The crude product was purified by radial chromatography (2 mm $SiO_2$; 1–5% MeOH in $CH_2Cl_2$) to yield 18 as a white solid, 44.9 mg (81%). mp 254–256° C. (dec.); $^1$H NMR (DMSO-$d_6$) δ 2.88 (m, 2H), 3.40 (m, 2H), 3.74 (s, 3H), 7.34 (t, 1H, J=7.7 Hz), 7.56 (m, 5H), 7.73 (d, 1H, J=7.7 Hz), 7.80 (d, 1H, J=7.7 Hz), 8.15 (bt, 1H); Anal. ($C_{18}H_{16}N_2O.0.75\ H_2O$) C, H, N.

Compound 18a, 1,5-dimethyl-2-phenyl-3,4,5,6-tetrahydro-1H-azepino[5,4,3-cd]indol-6-one, was isolated as a minor product. mp 175–177° C.; $^1$H NMR (DMSO-$d_6$) δ2.91 (m, 2H), 3.19 (s, 3H), 3.65 (m, 2H), 3.75 (s, 3H), 7.34 (t, 2H, J=7.8 Hz), 7.58 (m, 5H), 7.72 (d, 1H, J=7.8 Hz), 7.79 (d, 1H, J=7.8 Hz); Anal. ($C_{19}H_{18}N_2O.0.5\ H_2O$) C, H, N.

Example P

1-N-Methyl-3,4,5,6-tetrahydro-1H-azepino[5,4,3-cd]indol-6-one (19)

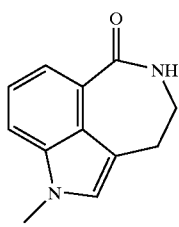

(19)

A solution of methyl indole-4-carboxylate (402 mg, 2.30 mmol) in DMF (5 mL) was cooled with an ice/water bath and treated with NaH (100 mg, 2.5 mmol, 60% in mineral oil). The resulting yellow solution was allowed to stir at 0° C. for 30 min., then a solution of MeI (482 mg, 212 μL, 3.4 mmol) in DMF (3.5 mL) was added dropwise. The solution was allowed to warm to ambient temperature. The reaction was quenched at 0° C. with saturated aqueous $NH_4Cl$ and extracted with EtOAc (10 mL×3). The organic solution was washed with water and brine, dried ($Na_2SO_4$), filtered, and concentrated to give methyl (N-methyl)-indole-4-carboxylate as a yellow oil, 430 mg (99%). The N-methyl carboxy indole was converted into the N-methyl-[5,6,7]-tricyclic indole in a manner similar to that described for Compound (10) to give 1-N-methyl-3,4,5,6-tetrahydro-1H-azepino[5,4,3-cd]indol-6-one as a shiny white solid, 256 mg (54%, after recrystallization ($CH_2Cl_2$/MeOH/hexanes)). mp 194–195° C.; $^1$H NMR (300 MHz, $d_6$-DMSO) δ 2.96 (m, 2H), 3.43 (m, 2H), 3.82 (s, 3H), 7.29 (m, 2H), 7.64 (d, 1H, J=7.7 Hz), 7.72 (d, 1H, J=7.7 Hz), 8.09 (br t, 1H); HRMS (FAB, MH+) Calcd for $C_{12}H_{13}N_2O$: 201.1028, Found: 201.1020; Anal. ($C_{12}H_{12}N_2O.0.2H_2O$) C, H, N.

Example Q (rac)-3-Phenyl-3,4,5,6-tetrahydro-1H-azepino[5,4,3-cd]indol-6-one (20)

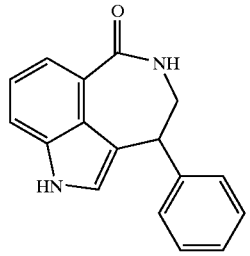

(20)

In a manner similar to that described for the preparation of methyl 3-(nitroethyl)-indole-4-carboxylate D above, methyl indole-4-carboxylate (85 mg, 0.49 mmol) and nitrostyrene (80 mg, 0.54 mmol) were heated at 160° C. in a sealed tube for 12 h. The product was isolated by silica gel chromatography as a brown oil, 132 mg (83%). The intermediate nitro alkane was reduced/cyclized as described to give (rac)-3-phenyl-3,4,5,6-tetrahydro-1H-azepino[5,4,3-cd]indol-6-one as a white solid, 51.4 mg (48%, after chromatography and recrystallization). mp 201–203° C.; $^1$H NMR (300 MHz, $d_6$-DMSO) δ 3.73 (m, 2H), 4.42 (m, 1H), 7.28 (br m, 8H), 7.64 (d, 1H, J=7.9 Hz), 7.77 (d, 1H, J=7.9 Hz), 11.32 (br s, 1H); HRMS (FAB, MH+) Calcd for $C_{17}H_{15}N_2O$: 263.1184, Found: 263.1180; Anal. ($C_{17}H_{14}N_2O.0.25\ H_2O$) C, H, N.

Example R 2-(4-Fluorophenyl)-3,4,5,6-tetrahydro-1H-azepino[5,4,3-cd]indol-6-one (23)

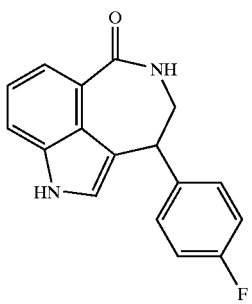

(23)

In a manner similar to that described for Compound 12, the tricyclic bromide (100 mg, 0.54 mmol) and 4-fluorobenzeneboronic acid (79 mg, 0.57 mmol) were coupled to yield 2-(4-fluorophenyl)-3,4,5,6-tetrahydro-1H-azepino[5,4,3-cd]indol-6-one, 107 mg (99%), as a pale-yellow solid. $^1$H NMR (300 MHz, $d_6$-DMSO) δ 3.04 (m, 2H), 3.38 (m, 2H), 7.22 (app t, 1H, J=7.7 Hz), 7.39 (m, 2H), 7.56 (dd, 1H, J=8.0, 0.9 Hz), 7.64 (m, 3H), 8.05 (br t, 1H), 11.57 (br s, 1H); HRMS (FAB, MH+) Calcd for $C_{17}H_{14}FN_2O$: 281.1090, Found: 281.1093; Anal. ($C_{17}H_{13}FN_2O \cdot 0.6\ H_2O$) C, H, N.

Example S

8-Bromo-2-phenyl-3,4,5,6-tetrahydro-1H-azepino[5,4,3-cd]indol-6-one

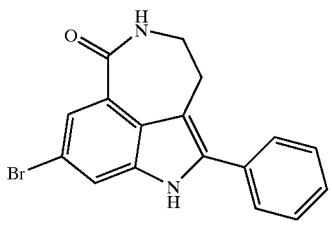

(26)

(26)

A solution of Compound 12 (2-phenyl-3,4,5,6-tetrahydro-1H-azepino[5,4,3-cd]indol-6-one) (22 mg, 0.08 mmol) in $CH_2Cl_2$ (1 mL) and THF (1 mL) was treated with pyridinium tribromide (29 mg, 0.09 mmol). The solution was stirred for 3 hours at room temperature and then diluted with water (2 mL), and the aqueous layer was adjusted to pH=9–10 with 1M NaOH. The mixture was extracted with $CH_2Cl_2$ (3×5 mL). The organic solution was washed with water and brine, dried ($Na_2SO_4$), filtered, and concentrated. The crude product was purified by radial chromatography (1 mm silica gel; 1% MeOH in $CHCl_3$) to give the 8-bromo compound, 12.8 mg (47%), as a pale-yellow solid. $^1$H NMR (300 MHz, $d_6$-DMSO) δ 3.06 (m, 2H), 3.39 (m, 2H), 7.43 (app t, 1H, J=7.4 Hz), 7.55 (app t, 2H, J=7.6 Hz), 7.66 (app d, 2H, J=7.6 Hz), 7.70 (app d, 1H, J=1.5 Hz), 7.75 (app d, 1H, J=1.5 Hz), 8.24 (br t, 1H), 11.77 (br s, 1H); HRMS (FAB, MH+) Calcd for $C_{17}H_{14}BrN_2O$: 341.0289, Found: 341.0294.

Example T 2-(4-(N,N-Dimethylamino)methylphenyl)-3,4,5,6-tetrahydro-1H-azepino[5,4,3-cd]indol-6-one (21)

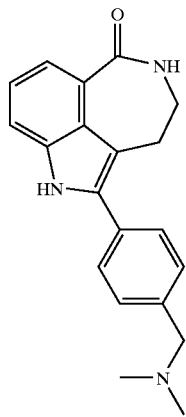

(21)

In a manner similar to that described above for Compound 12, the tricyclic bromide (168 mg, 0.63 mmol) and 4-formylbenzeneboronic acid (142 mg, 0.95 mmol) were coupled to yield 2-(4-formylphenyl)-3,4,5,6-tetrahydro-1H-azepino[5,4,3-cd]indol-6-one, 141 mg (77%), as a yellow solid. mp 238–240° C. (dec.); $^1$H NMR (300 MHz, $d_6$-DMSO) δ 3.12 (m, 2H), 3.42 (m, 2H), 7.28 (t, 1H, J=7.6 Hz), 7.59 (d, 1H, J=7.6 Hz), 7.62 (d, 1H, J=7.6 Hz), 7.88 (d of ABq, 2H, J=7.7 Hz), 8.05 (d of ABq, 2H, J=7.7 Hz), 8.11 (br t, 1H), 10.07 (s, 1H), 11.75 (br s, 1H); HRMS (FAB, MH+) Calcd for $C_{18}H_{15}N_2O_2$: 291.1134, Found: 291.1132.

The aldehyde (310 mg, 1.07 mmol) in MeOH (40 mL) was treated with dimethyl amine (2M solution in MeOH, 6.41 mmol). The solution was cooled with an ice/water bath and treated dropwise with a solution of sodium cyanoborohydride (74 mg, 1.18 mmol) and zinc chloride (80 mg, 0.59 mmol) in MeOH (10 mL). The resulting solution was adjusted to pH=6–7 with 2M methanolic HCl. After stirring for 30 min., the reaction was quenched with conc. HCl (0.2 mL) and the methanol was removed by evaporation. The residue was diluted with water (30 mL). The solution adjusted to pH=10–11 with KOH (s) and extracted with $CH_2Cl_2$ (30 mL×3). The organic solution was washed with water and brine, dried ($Na_2SO_4$), filtered, and concentrated. The crude product was crystallized ($CH_2Cl_2$/MeOH/hexanes) to give 2-(4-(N,N-dimethylamino)methylphenyl)-3,4,5,6-tetrahydro-1H-azepino[5,4,3-cd]indol-6-one, 245 mg (72%), as an off-white solid. mp 226–229° C. (dec.); $^1$H NMR (300 MHz, $d_6$-DMSO) δ 2.18 (s, 6H), 3.06 (m, 2H), 3.40 (m, 2H), 3.44 (s, 2H), 7.21 (t, 1H, J=7.7 Hz), 7.43 (d of ABq, 2H, J=7.9 Hz), 7.56 (d, 1H, J=7.7 Hz), 7.61 (d of ABq, 2H, J=7.9 Hz), 7.69 (d, 1H, J=7.7 Hz), 8.05 (br t, 1H), 11.53 (br s, 1H); HRMS (FAB, MH+) Calcd for $C_{20}H_{22}N_3O$: 320.1763; Found: 320.1753; Anal. ($C_{20}H_{21}N_3O \cdot 0.55H_2O$) C, H, N.

Example U 2-(3-(N,N-Dimethylamino)methylphenyl)-3,4,5,6-tetrahydro-1H-azepino[5,4,3-cd]indol-6-one (22)

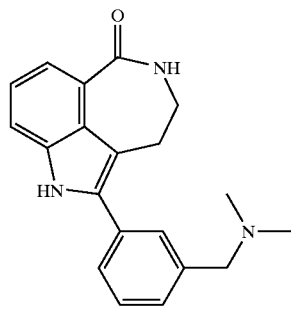

(22)

The aldehyde compound 15 (346 mg, 1.19 mmol) in MeOH (40 mL) was treated with dimethyl amine (2M solution in MeOH, 7.16 mmol). The solution was cooled with an ice/water bath and treated dropwise with a solution of sodium cyanoborohydride (82 mg, 1.31 mmol) and zinc chloride (89 mg, 0.66 mmol) in MeOH (10 mL). The resulting solution was adjusted to pH=6–7 with 2M methanolic HCl. After stirring for 30 min., the reaction was quenched with conc. HCl (0.2 mL) and the methanol was removed by evaporation. The residue was diluted with water (30 mL). The solution was adjusted to pH=10–11 with KOH (s) and extracted with $CH_2Cl_2$ (30 mL×3). The organic solution was washed with water and brine, dried ($Na_2SO_4$), filtered, and concentrated. The crude product was crystallized ($CH_2Cl_2$/MeOH/hexanes) to give 2-(3-(N,N-dimethylamino)methylphenyl)-3,4,5,6-tetrahydro-1H-azepino[5,4,3-cd]indol-6-one, 332 mg (87%), as shiny yellow crystals. mp 222–225° C.; $^1$H NMR (300 MHz, d$_6$-DMSO) δ 2.20 (s, 6H), 3.06 (m, 2H), 3.40 (m, 2H), 3.50 (s, 2H), 7.21 (t, 1H, J=7.7 Hz), 7.41 (br d, 1H, J=7.4 Hz), 7.50 (m, 4H), 7.69 (d, 1H, J=7.1 Hz), 8.05 (br t, 1H), 11.56 (br s, 1H); HRMS (FAB, MH+) Calcd for C$_{20}$H$_{22}$N$_3$O: 320.1763, Found: 320.1753; Anal. (C$_{20}$H$_{21}$N$_3$O.0.25 H$_2$O) C, H, N.

Example V

Compound 25

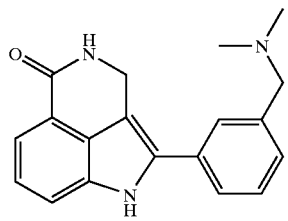

(25)

To a solution of 2M (CH$_3$)$_2$NH in MeOH (0.6 mL, 1.13 mmol) was added 5N HCl-MeOH (0.08 mL, 0.380 mmol) followed by a suspension of the aldehyde (0.055 g, 0.188 mmol) in 3 mL MeOH and NaBH$_3$CN (0.012 g, 0.188 mmol). The resulting suspension was stirred for 24 h at room temperature. Concentrated HCl was added until the pH was less than 2, and the MeOH was removed in vacuo. The residue was taken up in H$_2$O and extracted with EtOAc. The aqueous solution was brought to about pH 9 with solid(s) KOH and extracted with EtOAc. The organic layer was dried over MgSO$_4$ and concentrated to give a yellow solid, which was purified by flash silica gel chromatography eluting with a gradient of CHCl$_3$ to 10% MeOH/NH$_3$ in CHCl$_3$ to give 0.024 g of a yellow solid. $^1$H NMR (DMSO-d$_6$) 2.18 (s, 6H), 3.45 (s, 2H), 5.03 (s, 2H), 7.20–7.30 (m, 2H), 7.35 (d, 1H, J=6 Hz), 7.40–7.58 (m, 3H), 7.60 (s, 1H), 7.79 (s br, 1H), 11.68 (s br, 1H); HRMS 306.1626.

Example W 1,5-Dihydro-[1,2]diazepino[4,5,6-cd]-indol-6-one (27)

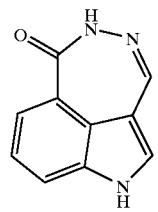

(27)

A solution of the intermediate J (3-formyl carboxy indole (246 mg, 1.21 mmol)) in MeOH (10 mL) and AcOH (0.1 mL) was treated with hydrazine hydrate (176 mg, 3.5 mmol) and the solution was heated at reflux for 30 min. The solution was cooled in an ice/water bath and the precipitated solid was collected by filtration to give 1,5-dihydro-[1,2]diazepino[4,5,6-cd]-indol-6-one, 168 mg (75%), as a bright-yellow solid. mp 335–336° C. (dec.); $^1$H NMR (300 MHz, d$_6$-DMSO) δ 7.11 (t, 1H, J=7.8 Hz), 7.44 (m, 3H), 7.56 (d, 1H, J=2.7 Hz), 10.09 (s, 1H), 11.74 (br s, 1H); Anal. (C$_{10}$H$_7$N$_3$O) C, H, N.

Example X 1,5-Dihydro-3-phenyl-[1,2]diazepino[4,5,6-cd]-indol-6-one (28)

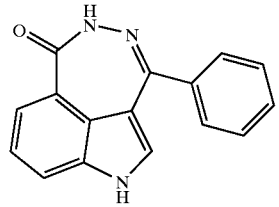

(28)

A solution of methyl indole-4-carboxylate (40 mg, 0.23 mmol) in dichloroethane (2 mL) was treated with benzoyl chloride (0.69 mmol) at room temperature. The orange solution was cooled with an ice/water bath and treated with aluminum chloride (0.69 mmol). The dark-orange solution was warmed to room temperature over 1 hour, then poured into ice-cold aqueous 2M HCl. The aqueous solution was adjusted to pH=9–10 with KOH (s), and extracted with CH$_2$Cl$_2$ (10 mL×3). The organic solution was washed with water and brine, dried (Na$_2$SO$_4$), filtered, and concentrated. The crude product was purified by radial chromatography (1 mm silica gel; 3% MeOH in CHCl$_3$) to give methyl 3-phenacyl-indole-4-carboxylate as an oil, 63 mg (99%). A solution of the 3-phenacyl carboxy indole (60 mg, 0.25 mmol) in MeOH (5 mL) and conc. HCl (0.1 mL) was treated with hydrazine hydrate (36 mg, 0.73 mmol) and the solution was heated at reflux for 3 h. The reaction was quenched with ice/water, and the aqueous layer was adjusted to pH=10–11 with KOH (s) and extracted with CH$_2$Cl$_2$ (30 mL×3). The organic solution was washed with water and brine, dried (Na$_2$SO$_4$), filtered, and concentrated. The crude product was crystallized (CH$_2$Cl$_2$/hexanes) to give 1,5-dihydro-3-phenyl-[1,2]diazepino[4,5,6-cd]-indol-6-one, 33 mg (51%), as a bright-yellow solid. mp 177–179° C.; $^1$H NMR (300 MHz, d$_6$-DMSO) δ 7.22 (m, 2H), 7.47 (m, 3H), 7.58 (m, 4H), 10.45 (s, 1H), 11.92 (br s, 1H); Anal. (C$_{10}$H$_7$N$_3$O.0.75 H$_2$O) C, H, N.

Example Y 1,5-Dihydro-3-phenethyl-[1,2]diazepino[4,5,6-cd]-indol-6-one (29)

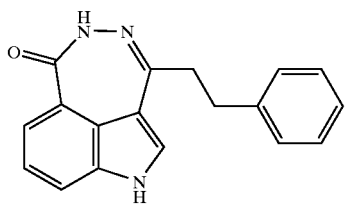

(29)

A solution of methyl indole-4-carboxylate (250 mg, 1.43 mmol) in dichloroethane (3 mL) was treated with 3-phenylpropionyl chloride (361 mg, 2.14 mmol) at room temperature. The orange solution was cooled to 0° C. and treated with aluminum chloride (572 mg, 4.29 mmol). The reaction mixture was stirred at room temperature for 2 h, then poured into ice-cold 1M aqueous HCl. The aqueous solution was adjusted to pH=8 with 1M NaOH, and extracted with CH$_2$Cl$_2$ (10 mL×3). The organic solution was washed with water and brine, dried (Na$_2$SO$_4$), filtered, and concentrated to give methyl 3-(3-phenylpropionyl)-indole-4-carboxylate as a pale-yellow solid, 395 mg (90%). A solution of the 3-(3-phenylpropionyl)-4-carboxy indole (95.5 mg, 0.31 mmol) in MeOH (3 mL) and HCl (0.1 mL) was treated with hydrazine hydrate (47 mg, 0.93 mmol) and the solution was heated at reflux for 8 h. The solution was cooled in an ice/water bath and the precipitated solid was collected by filtration to give 1,5-dihydro-3-phenethyl-[1,2]diazepino[4,5,6-cd]-indol-6-one, 60.2 mg (71%). The crude product was purified by radial chromatography (2 mm SiO$_2$, 5:1 hexanes:EtOAc) to give a yellow solid. mp 182–183.5° C.; $^1$H NMR (300 MHz, d$_6$-DMSO) δ 2.80 (m, 2H), 2.84 (m, 2H), 7.22 (m, 2H), 7.31 (m, 4H), 7.54 (m, 2H), 7.81 (s, 1H), 10.19 (s, 1H), 11.92 (br s, 1H); Anal. (C$_{10}$H$_7$N$_3$O.0.1 H$_2$O) C, H, N.

Example Z 2-(3-Trifluoromethyl-phenyl)-1,3,4,5-tetrahydro-azepino[5,4,3-cd]indol-6-one (30)

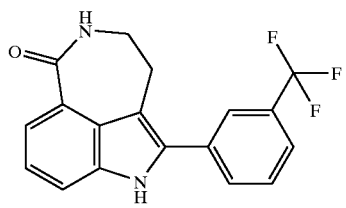

(30)

In a manner similar to that described for Compound 12, the tricyclic bromide (300 mg, 1.13 mmol) and 3-trifluoromethylphenylboronic acid (322 mg, 1.70 mmol) were coupled to yield 2-(3-trifluoromethyl-phenyl)-1,3,4,5-tetrahydro-azepino[5,4,3-cd]indol-6-one, 300 mg (80%), as a pale-yellow solid. mp 212.5–213.5° C.; $^1$H NMR (300 MHz, d$_6$-DMSO) δ 3.08 (m, 2H), 3.40 (m, 2H), 7.27 (app t, 1H, J=7.8 Hz), 7.60 (d, 1H, J=7.8 Hz), 7.71 (d, 1H, J=7.5 Hz), 7.77 (m, 2H), 7.96 (m, 2H), 8.13 (br t, 1H), 11.78 (br s, 1H); MS (FAB, MH+) 331; Anal. (C$_{18}$H$_{13}$F$_3$N$_2$O.0.5 H$_2$O) C, H, N.

Example AA 2-(4-Trifluoromethyl-phenyl)-1,3,4,5-tetrahydro-azepino[5,4,3-cd]indol-6-one (31)

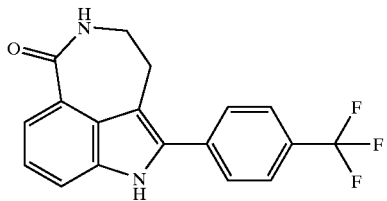

(31)

In a manner analogous to the method described above for Compound 12, the tricyclic bromide (300 mg, 1.13 mmol) and 4-trifluoromethylphenylboronic acid (322 mg, 1.70 mmol) were coupled to yield 2-(4-trifluoromethyl-phenyl)-1,3,4,5-tetrahydro-azepino[5,4,3-cd]indol-6-one, 261 mg (70%), as an off-white solid. mp 208–209° C.; $^1$H NMR (300 MHz, d$_6$-DMSO) δ 3.09 (m, 2H), 3.40 (m, 2H), 7.27 (app t, 1H, J=7.8 Hz), 7.60 (dd, 1H, J=8.1, 0.9 Hz), 7.71 (dd, 1H, J=7.5, 0.6 Hz), 7.88 (m, 4H), 8.13 (br t, 1H), 11.77 (br s, 1H); MS (FAB, MH+) 331; Anal. (C$_{18}$H$_{13}$F$_3$N$_2$O.1.0 H$_2$O) C, H, N.

Example BB

2-Benzofuran-2-yl-1,3,4,5-tetrahydro-azepino[5,4,3-cd]indol-6-one (32)

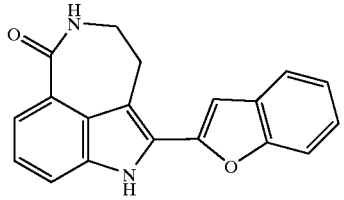

(32)

In a like manner to the example described above for Compound 12, the tricyclic bromide (300 mg, 1.13 mmol) and benzo[b]furan-2-boronic acid (202 mg, 1.24 mmol) were coupled to yield 2-benzofuran-2-yl-1,3,4,5-tetrahydro-azepino[5,4,3-cd]indol-6-one, 262 mg (77%), as a yellow solid. mp 207° C. (dec.); $^1$H NMR (300 MHz, d$_6$-DMSO) δ 3.23 (m, 2H), 3.50 (m, 2H), 7.31 (m, 4H), 7.61 (dd, 1H, J=8.1, 0.9 Hz), 7.70 (m, 3H), 8.14 (brt, 1H), 11.97 (br s, 1H); MS (FAB, MH+) 303; Anal. (C$_{19}$H$_{14}$N$_2$O$_2$.1.8 H$_2$O) C, H, N.

Example CC 2-(3,5-bis-Trifluoromethyl-phenyl)-1,3,4,5-tetrahydro-azepino[5,4,3-cd]indol-6-one (33)

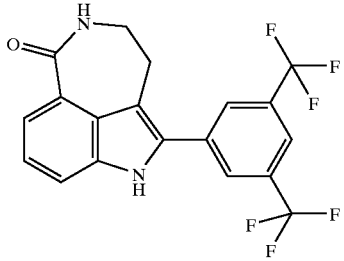

(33)

In a manner similar to that described for preparation of Compound 12, the tricyclic bromide (300 mg, 1,13 mmol) and 3,5-bis-trifluoromethylphenylboronic acid (202 mg, 1.24 mmol) were coupled to yield 2-(3,5-bis-trifluoromethyl-phenyl)-1,3,4,5-tetrahydro-azepino[5,4,3-cd]indol-6-one, 70 mg (16%), as a pale-yellow solid. mp 230° C. (dec.); $^1$H NMR (300 MHz, d$_6$-DMSO) δ 3.11 (m, 2H), 3.42 (m, 2H), 7.31 (app t, 1H, J=7.8 Hz), 7.64 (d, 1H, J=8.1 Hz), 7.73 (d, 1H, J=7.5 Hz), 8.13 (br s, 1H), 8.16 (br t, 1H), 8.28 (br s, 2H), 11.95 (br s, 1H); MS (FAB, MH+) 399; Anal. (C$_{19}$H$_{12}$F$_6$N$_2$O.0.2 hexanes) C, H, N.

Example DD

2-(4-Bromophenyl)-1,3,4,5-tetrahydro-azepino[5,4,3-cd]indol-6-one (34)

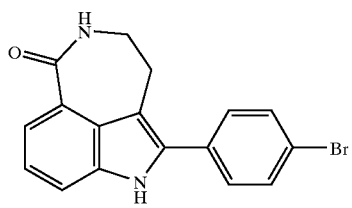

(34)

In a manner similar to that described for Compound 12, 2-iodo-1,3,4,5-tetrahydro-azepino[5,4,3-cd]indol-6-one (85 mg, 0.28 mmol; see Example NN below) and 4-bromophenylboronic acid (62 mg, 0.31 mmol) were coupled to yield 2-(4-bromophenyl)-1,3,4,5-tetrahydro-azepino[5,4,3-cd]indol-6-one, 19 mg (20%), as a white solid. mp 160° C. (dec.); $^1$H NMR (300 MHz, d$_6$-DMSO) δ 3.04 (m, 2H), 3.39 (m, 2H), 7.23 (app t, 1H, J=7.5 Hz), 7.56 (dd, 1H, J=8.1, 0.9 Hz), 7.60 (d, 2H, J=8.7 Hz), 7.69 (dd, 1H, J=7.5, 0.6 Hz), 7.73 (d, 2H, J=8.4 Hz), 8.09 (br t, 1H), 11.64 (br s, 1H); MS (FAB, MH+) 341/343; Anal. (C$_{17}$H$_{13}$BrN$_2$O.0.6 H$_2$O) C, H, N.

Example EE

2-(3-Chloro-4-fluoro-phenyl)-1,3,4,5-tetrahydro-azepino[5,4,3-cd]indol-6-one (35)

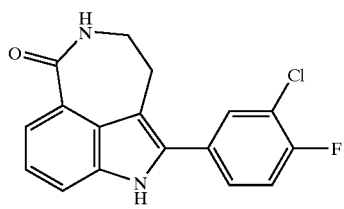

(35)

In a manner similar to that described for Compound 12, the tricyclic bromide (300 mg, 1.13 mmol) and 3-chloro-4-fluorophenylboronic acid (217 mg, 1.24 mmol) were coupled to yield 2-(3-chloro, 4-fluoro-phenyl)-1,3,4,5-tetrahydro-azepino[5,4,3-cd]indol-6-one, 217 mg (61%), as a pale-yellow solid. mp 234–235° C.; $^1$H NMR (300 MHz, d$_6$-DMSO) δ 3.04 (m, 2H), 3.39 (m, 2H), 7.24 (app t, 1H, J=7.8 Hz), 7.57 (dd, 1H, J=8.1, 0.9 Hz), 7.61 (m, 2H), 7.69 (dd, 1H, J=7.5, 0.9 Hz), 7.85 (dd, 1H, J=7.2, 2.1 Hz), 8.10 (br t, 1H), 11.68 (br s, 1H); HRMS (FAB, MH+) Calcd for C$_{17}$H$_{13}$ClFN$_2$O. 315.0700, Found: 315.0704; Anal. (C$_{17}$H$_{12}$ClFN$_2$O.1.0 H$_2$O.0.5 MeOH) C, H, N.

Example FF

2-(4-tert-Butyl-phenyl)-1,3,4,5-tetrahydro-azepino[5,4,3-cd]indol-6-one (36)

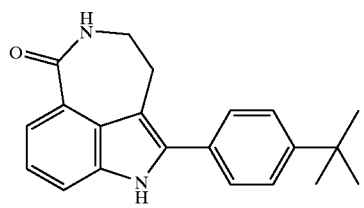

(36)

In a like manner as described for Compound 12, the tricyclic bromide (300 mg, 1.13 mmol) and 4-tert-butylphenylboronic acid (302 mg, 1.70 mmol) were coupled to yield 2-(4-tert-butyl-phenyl)-1,3,4,5-tetrahydro-azepino[5,4,3-cd]indol-6-one, 150 mg (42%), as a white solid. mp 243–244° C.; $^1$H NMR (300 MHz, d$_6$-DMSO) δ 1.33 (s, 9H), 3.05 (m, 2H), 3.38 (m, 2H), 7.20 (app t, 1H, J=7.8 Hz), 7.57 (m, 5H), 7.67 (dd, 1H, J=7.2, 0.6 Hz), 8.07 (br t, 1H), 11.51 (br s, 1H); HRMS (FAB, MH+) Calcd for C$_{21}$H$_{23}$N$_2$O: 319.1810, Found: 319.1813; Anal. (C$_{21}$H$_{22}$N$_2$O.0.3 H$_2$O) C, H, N.

Example GG

2-Phenyl-1,3,4,5-tetrahydro-azepino[5,4,3-cd]indole-6-thione (24)

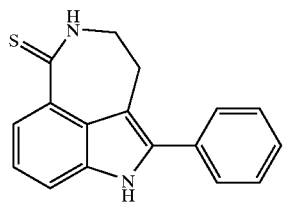

(24)

Compound 12 (48.6 mg, 0.18 mmol) in toluene (2 mL) was treated with Lawesson's reagent (75 mg, 0.18 mmol) at room temperature. The solution was heated at reflux for 2 h, then allowed to cool to room temperature and diluted with water. The mixture was extracted with EtOAc (3×5 mL). The organic solution was washed with water and brine, dried (Na$_2$SO$_4$), filtered, and concentrated. The crude product was crystallized (CH$_2$Cl$_2$/hexanes) to give the thioamide 34.4 mg (68%) as a yellow solid. mp 223–226° C. (dec.); $^1$H NMR (300 MHz, d$_6$-DMSO) δ 3.10 (m, 2H), 3.50 (m, 2H), 7.23 (app t, 1H, J=7.8 Hz), 7.57 (m, 1H), 7.61 (m, 3H), 7.69 (m, 2H), 8.19 (d, 1H, J=7.6 Hz), 10.56 (br t, 1H), 11.68 (br s, 1H); HRMS (FAB, MH+) Calcd for C$_{17}$H$_{15}$N$_2$S: 279.0956, Found: 279.0952; Anal. (C$_{17}$H$_{14}$N$_2$S.0.25 H$_2$O) C, H, N, S.

Example HH

2-Phenethyl-1,3,4,5-tetrahydro-azepino[5,4,3-cd]indol-6-one (37)

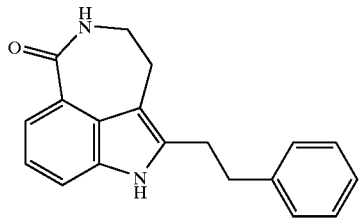

(37)

2-Phenylethynyl-3,4,5,6-tetrahydro-1H-azepino[5,4,3-cd]indol-6-one (Compound 17) (37 mg, 0.13 mmol) and platinum oxide (1.5 mg, 0.05 mmol) were suspended in 2 mL MeOH under an argon atmosphere. The flask was flushed with hydrogen gas and the resulting mixture stirred at 24° C. under 1 atmosphere of hydrogen for 20 h. The catalyst was filtered off and the resulting solution concentrated, leaving a pale-yellow crystalline solid. Purification by radial chromatography (5% MeOH in CHCl$_3$) followed by recrystallization (MeOH/CHCl$_3$/hexanes) yielded 2-phenethyl-1,3,4,5-tetrahydro-azepino[5,4,3-cd]indol-6-one, 14 mg (37%), as a pale-yellow solid. mp 207–208° C.; $^1$H NMR (300 MHz, d$_6$-DMSO) δ 2.60 (m, 2H), 2.95 (m, 4H), 3.26 (m, 2H), 7.17 (m, 6H), 7.46 (dd, 1H, J=7.8, 0.6 Hz), 7.61 (dd, 1H, J=7.5, 0.6 Hz), 7.90 (br t, 1H), 11.16 (br s, 1H); MS (FAB, MH+) 291; Anal. (C$_{19}$H$_{18}$N$_2$O) C, H, N.

Example II 2-(2-Chlorophenyl)-1,3,4,5-tetrahydro-azepino[5,4,3-cd]indol-6-one (38)

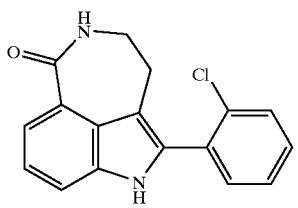

(38)

In a manner similar to that described for Compound 12, the tricyclic bromide (210 mg, 0.79 mmol) and 2-chlorophenylboronic acid (136 mg, 0.87 mmol) were coupled to yield 2-(2-chlorophenyl)-1,3,4,5-tetrahydro-azepino[5,4,3-cd]indol-6-one, 78 mg (33%), as a shiny white solid. mp 275° C. (dec); $^1$H NMR (300 MHz, d$_6$-DMSO) δ 2.76 (m, 2H), 3.38 (m, 2H), 7.23 (app t, 1H, J=7.8 Hz), 7.56 (m, 5H), 7.71 (dd, 1H, J=7.5, 0.9 Hz), 8.07 (br t, 1H), 11.53 (br s, 1H); MS (FAB, MH+) 297; Anal. (C$_{17}$H$_{13}$N$_2$OCl·0.15 H$_2$O) C, H, N.

Example JJ 2-(2,4-Difluoro-phenyl)-1,3,4,5-tetrahydro-azepino[5,4,3-cd]indol-6-one (39)

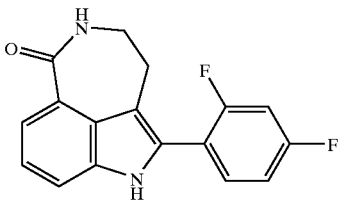

(39)

In a manner similar to that described for Compound 12, the tricyclic bromide (200 mg, 0.75 mmol) and 2,4-difluorophenylboronic acid (131 mg, 0.83 mmol) were coupled to yield 2-(2,4-difluoro-phenyl)-1,3,4,5-tetrahydro-azepino[5,4,3-cd]indol-6-one, 156 mg (69%), as a pale-yellow solid. mp 196–197° C.; $^1$H NMR (300 MHz, d$_6$-DMSO) δ 2.84 (m, 2H), 3.37 (m, 2H), 7.25 (app t, 1H, J=7.7 Hz), 7.27 (m, 1H), 7.47 (m, 1H), 7.57 (dd, 1H, J=8.1, 0.9 Hz), 7.64 (m, 1H), 7.70 (dd, 1H, J=7.5, 0.9 Hz), 8.08 (br t, 1H), 11.58 (br s, 1H); MS (FAB, MH+) 299; Anal. (C$_{17}$H$_{12}$N$_2$OF$_2$·0.3 H$_2$O·0.37 CHCl$_3$) C, H, N.

Example KK 2-(3-Chlorophenyl)-1,3,4,5-tetrahydro-azepino[5.4.3-cd]indol-6-one (40)

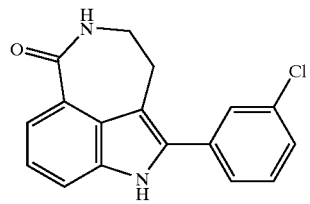

(40)

In a manner similar to that described for Compound 12, the tricyclic bromide (200 mg, 0.75 mmol) and 3-chlorophenylboronic acid (130 mg, 0.83 mmol) were coupled to yield 2-(3-chlorophenyl)-1,3,4,5-tetrahydro-azepino[5,4,3-cd]indol-6-one, 151 mg (67%), as a shiny pale-yellow solid. mp 147–149° C; $^1$H NMR (300 MHz, d$_6$-DMSO) δ 3.06 (m, 2H), 3.39 (m, 2H), 7.24 (app t, 1H, J=7.8 Hz), 7.46 (m, 1H), 7.58 (m, 4H), 7.70 (m, 2H), 7.64 (m, 1H), 8.11 (br t, 1H), 11.68 (br s, 1H); MS (FAB, MH+) 297; Anal. (C$_{17}$H$_{13}$N$_2$OCl·0.9 H$_2$O) C, H, N.

Example LL

2-Naphthalen-1-yl-1,3,4,5-tetrahydro-azepino[5,4,3-cd]indol-6-one (41)

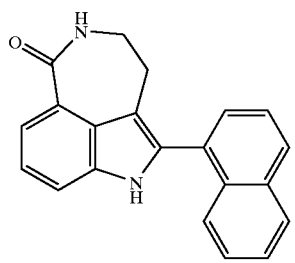
(41)

In a manner similar to that described for Compound 12, the tricyclic bromide (300 mg, 1.13 mmol) and 1-naphthaleneboronic acid (214 mg, 1.24 mmol) were coupled to yield 2-naphthalen-1-yl-1,3,4,5-tetrahydro-azepino[5,4,3-cd]indol-6-one, 70 mg (20%), as an off-white solid. mp 305° C. (dec.); $^1$H NMR (300 MHz, d$_6$-DMSO) δ 2.70 (m, 2H), 3.38 (m, 2H), 7.25 (app t, 1H, J=7.5 Hz), 7.61 (m, 5H), 7.75 (dd, 1H, J=7.5, 0.9 Hz), 7.82 (m, 1H), 8.06 (m, 3H), 11.67 (br s, 1H); MS (FAB, MH+) 313; Anal. ($C_{21}H_{16}N_2O \cdot 0.2\ H_2O$) C, H, N.

Example MM

6-Oxo-3,4,5,6-tetrahydro-1H-azepino[5,4,3-cd]indole-2-carboxylic acid methyl ester (42)

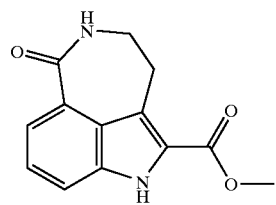
(42)

2-Iodo-1,3,4,5-tetrahydro-azepino[5,4,3-cd]indol-6-one (85 mg, 0.28 mmol; prepared as described below), palladium tetrakis(triphenylphosphine) (19 mg, 0.02 mmol), and triethylamine (52 mg, 0.51 mmol) were combined in toluene:methanol (8:2 (v/v), 2 mL). Carbon monoxide gas was bubbled through the mixture for 10 min. The reaction was then heated at 85° C. in a sealed tube for 16 h. The solvent was evaporated and the orange solid purified by radial chromatography (chloroform to 5% methanol in chloroform). The white solid was recrystallized (chloroform/methanol/hexanes) to yield 6-oxo-3,4,5,6-tetrahydro-1H-azepino[5,4,3-cd]indole-2-carboxylic acid methyl ester, 39 mg (100%), as an off-white solid. mp 266–267° C; $^1$H NMR (300 MHz, d$_6$-DMSO) δ 3.25 (m, 2H), 3.43 (m, 2H), 3.89 (s, 3H), 7.38 (app t, 1H, J=7.8 Hz), 7.61 (dd, 1H, J=8.1, 0.9 Hz), 7.74 (dd, 1H, J=7.5, 0.9 Hz), 8.17 (br t, 1H), 11.93 (br s, 1H); MS (FAB, MH+) 245; Anal. ($C_{13}H_{12}N_2O_3$) C, H, N.

Example NN

Preparation of 2-Iodo-1,3,4,5-tetrahydro-azepino[5,4,3-cd]indol-6-one (43)

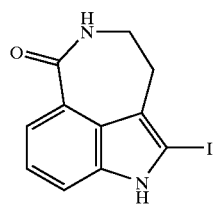
(43)

1,3,4,5-Tetrahydro-azepino[5,4,3-cd]indol-6-one (620 mg, 3.35 mmol) was suspended in 80 mL THF/CH$_2$Cl$_2$ (1:1), and then cooled in an ice bath. Bis(trifluoroacetoxy)-iodo]benzene (1.73 g, 4.02 mmol) and iodine (850 mg, 3.35 mmol) were added and the reaction stirred at 0° C. for 25 min. The ice bath was removed and the reaction allowed to stir for another 30 min. as it warmed to room temperature. The reaction was quenched by addition of aqueous sodium bisulfite. The layers were separated, and the organic layer was dried over MgSO$_4$, filtered, and concentrated in vacuo leaving a yellow solid. The crude solid was purified by flash chromatography (5% MeOH/CHCl$_3$) to yield 1,3,4,5-tetrahydro-azepino[5,4,3-cd]indol-6-one, 308 mg (30%), as a pale-yellow solid: $^1$H NMR (300 MHz, d$_6$-DMSO) δ 2.79 (m, 2H), 3.40 (m, 2H), 7.14 (app t, 1H, J=7.8 Hz), 7.46 (dd, 1H, J=7.8, 0.6 Hz), 7.64 (dd, 1H, J=7.5, 0.9 Hz), 8.06 (br t, 1H), 11.80 (br s, 1H); MS (FAB, MH+) 313.

By following methods analogous to those described in the above examples, the following compounds were also prepared:

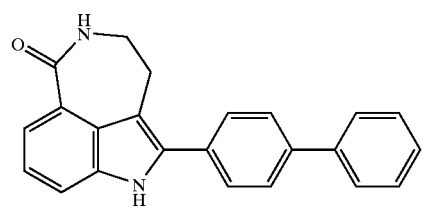
(VV)

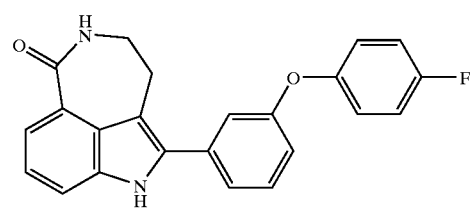
(UU)

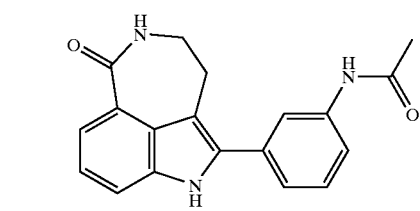
(TT)

Example OO 2-(4-(N-Methylamino)methylphenyl)-3,4,5,6-tetrahydro-1H-azepino[5,4,3-cd]indol-6-one

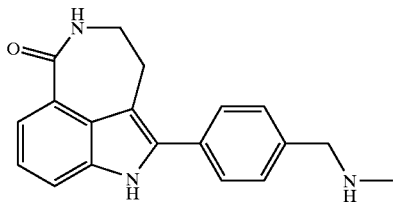

The p-aldehyde (150 mg, 0.52mmol) prepared as described for compound 21 in MeGH (20 mL) was treated, as described, with methyl amine (8.03 M solution in EtOH, 3.10 mmol) and a solution of sodium cyanoborohydride (0.57 mmol) and zinc chloride (0.28 mmol) in MeOH (2 mL) to give, after recrystallization (isopropyl alcohol/hexanes), 2-(4-(N-methylamino)methylphenyl)-3,4,5,6-tetrahydro-1H-azepino[5,4,3-cd]indol-6-one, 108 mg (68%) as a yellow solid: m.p. 208–210° C.; $^1$H NMR (300 MHz, $d_6$-DMSO) δ 2.34 (s, 3H), 3.05 (m, 2H), 3.39 (m, 2H), 3.77 (s, 2H), 7.20 (t, J=7.7 Hz, 1H), 7.54 (m, 3H), 7.61 (d of ABq, J=8.4 Hz, 2H), 7.67 (d, J=7.6 Hz, 1H), 8.07 (br t, 1H), 11.55 (br s, 1H). HRMS (FAB, MH+) Calcd for $C_{19}H_{20}N_3O$: 306.1606. Found: 306.1601. Anal. ($C_{19}H_{19}N_3O$·0.4 $H_2O$) C, H, N.

Example PP 2-(3-(N-Methylamino)methylphenyl)-3,4,5,6-tetrahydro-1H-azepino[5,4,3-cd]indol-6-one

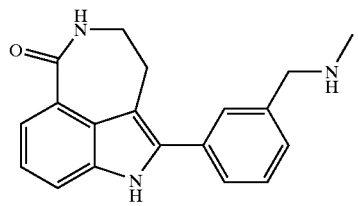

In a manner similar to that described for Compound 22, the aldehyde 15 (200 mg, 0.69 mmol) in MeOH (20 mL) was treated with methyl amine (2.0 M solution in THF, 4.20 mmol) and a solution of sodium cyanoborohydride (0.76 mmol) and zinc chloride (0.38 mmol) in MeOH (1.4 mL) to give, after recrystallization ($CH_2Cl_2$/MeOH/hexanes), 2-(3-(N-methylamino)methylphenyl)-3,4,5,6-tetrahydro-1H-azepino[5,4,3-cd]indol-6-one, 103 mg (49%) as pale yellow powder: m.p. 190–192° C.; $^1$H NMR (300 MHz, $d_6$-DMSO) δ 2.37 (s, 3H), 3.07 (m, 2H), 3.40 (m, 2H), 3.82 (s, 2H), 7.22 (t, J=7.7 Hz, 1H), 7.39 (br d, 1H), 7.49 (m, 1H), 7.56 (m, 2H), 7.68 (m, 2H), 8.09 (br t, 1H), 11.61 (br s, 1H). HRMS (FAB, MH+) Calcd for $C_{19}H_{20}N_3O$: 306.1606. Found: 306.1601. Anal. ($C_{19}H_{19}N_3O$·0.6 $H_2O$) C, H, N.

Example QQ 1,5-Dihydro-3-methyl-[1,2]diazepino[4,5,6-cd]-indol-6-one

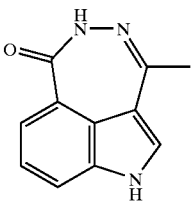

In a manner similar to that described for compound 28, a solution of methyl indole-4-carboxylate (427 mg, 2.44 mmol) in dichloroethane (7 mL) was treated with acetyl chloride (0.5 mL) and aluminum chloride (130 mg). The intermediate ketone (198 mg, 0.92 mmol) in MeOH (5 mL) and conc. HCl (0.05 mL) was treated, as described, with hydrazine hydrate (0.1 mL). The product precipitated, was collected by filtration and rinsed with ice-cold MeOH to give 1,5-dihydro-3-methyl-[1,2]diazepino[4,5,6-cd]-indol-6-one, 168 mg (92%) as a bright yellow solid: m.p. 335–336° C.; $^1$H NMR (300 MHz, $d_6$-DMSO) δ 2.17 (s, 3H), 7.19 (t, J=7.8 Hz, 1H), 7.54 (m, 2H), 7.67 (d, J=2.8Hz, 1H), 10.12 (s, 1H), 11.90 (br s, 1H). HRMS (FAB, MH+) Calcd for $C_{11}H_{10}N_3O$: 200.0824. Found: 200.0827. Anal. ($C_{11}H_9N_3O$) C, H, N.

Example RR 2-(3-Aminophenyl)-3,4,5,6-tetrahydro-1H-azepino[5,4,3-cd]indol-6-one

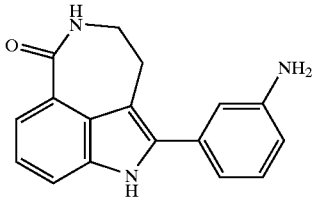

In a manner similar to that described for Compound 12, the tricyclic bromide (428 mg, 1.61 mmol) and 3-aminobenzeneboronic acid monohydrate (300 mg, 1.94 mmol) were coupled to yield 2-(3-aminophenyl)-3,4,5,6-tetrahydro-1H-azepino[5,4,3-cd]indol-6-one, 110 mg (25%) as an off-white solid: $^1$H NMR (300 MHz, $d_6$-DMSO) δ 3.03 (m, 2H), 3.39 (m, 2H), 5.24 (s, 2H), 6.59 (br d, 1H), 6.78 (d, J=7.7 Hz, 1H), 6.84 (m, 2H), 7.18 (m, 2H), 7.52 (d, J=7.9 Hz, 1H), 7.66 (d, J=7.4 Hz, 1H), 8.04 (br t, 1H), 11.41 (brs, 1H). HRMS (FAB, MH+)Calcd for $C_{17}H_{16}N_3O$: 278.1293. Found: 278.1297. Anal. ($C_{17}H_{15}N_3O$·1.1 $H_2O$) C, H, N.

Example SS 2-(3-(3-Piperidin-1-ylmethylphenyl)-3,4,5,6-tetrahydro-1H-azepino[5,4,3-cd]indol-6-one

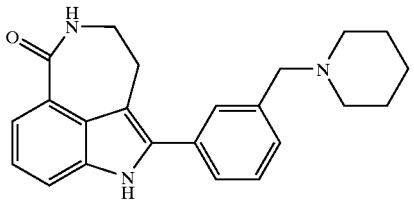

In a manner similar to that described for Compound 22, the aldehyde 15 (109 mg, 0.38 mmol) in MeOH (10 mL) was treated with piperidine (0.19 mL, 1.9 mmol) and a solution of sodium cyanoborohydride (0.57 mmol) and zinc chloride (0.28 mmol) in MeOH (1.1 mL) to give, after recrystallization ($CH_2Cl_2$/hexanes), 2-(3-(3-piperidin-1-ylmethylphenyl)-3,4,5,6-tetrahydro-1H-azepino[5,4,3-cd]indol-6-one, 94.1 mg (69%) as pale yellow powder: m.p. 235–237° C.; $^1$H NMR (300 MHz, $d_6$-DMSO) δ 1.41 (m, 2H), 1.52 (m, 4H), 2.37 (m, 4H), 3.06 (m, 2H), 3.39 (m, 2H), 3.52 (s, 2H), 7.21 (t, J=7.7 Hz, 1H), 7.31 (m, 1H), 7.54 (m, 4H), 7.69 (m, 1H), 8.08 (br t, 1H), 11.58 (br s, 1H). Anal. ($C_{23}H_{25}N_3O.065 H_2O$) C, H, N.

Example TT

N-[3-(6-Oxo-3,4,5,6-tetrahydro-1H-azepino[5,4,3-cd]indol-2-yl)-phenyl]-acetamide

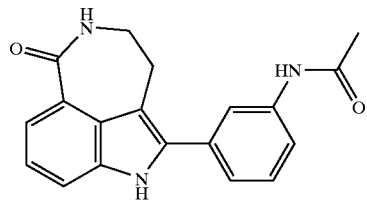

In a manner similar to that described for Compound 12, the tricyclic bromide (300 mg, 1.13 mmol) and 3-acetamidophenylboronic acid (304 mg, 1.70 mmol) were coupled to yield N-[3-(6-Oxo-3,4,5,6-tetrahydro-1H-azepino[5,4,3-cd]indol-2-yl)-phenyl]-acetamide, 10 mg (3%) as a clear solid: m.p. 300.5–302.0° C.; $^1$H NMR (300 MHz, $d_6$-DMSO) δ 2.09 (s, 3H), 3.05 (m, 2H), 3.36 (m, 2H), 7.21 (app t, J=7.5 Hz, 1H), 7.33 (d, J=7.5 Hz, 1H), 7.44 (t, J=7.8 Hz, 1H), 7.57 (m, 2H), 7.68 (d, J=7.5 Hz, 1H), 7.92 (br s, 1H), 8.08 (br t, 1H), 10.10 (br s, 1H), 11.56 (br s, 1H). MS (FAB, MH+) 320. Anal. ($C_{19}H_{17}N_3O_2$) C, H, N.

Example UU

2-[3-(4-Fluoro-phenoxy)-phenyl]-1,3,4,5-tetrahydro-azepino[5,4,3-cd]indol-6-one

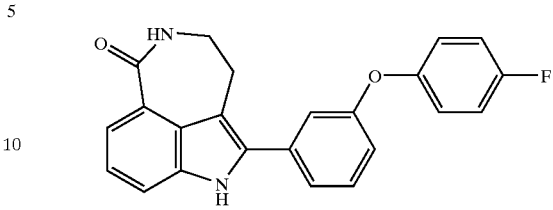

In a manner similar to that described for Compound 12, the tricyclic bromide (200 mg, 0.75 mmol) and 3-(4-fluoro-phenoxy)-phenylboronic acid (213 mg, 0.83 mmol) were coupled to yield 2-[3-(4-fluoro-phenoxy)-phenyl]-1,3,4,5-tetrahydro-azepino[5,4,3-cd]indol-6-one, 170 mg (60%) as a yellow crystalline solid: m.p. 240–241° C.; $^1$H NMR (300 MHz, $d_6$-DMSO) δ 3.01 (m, 2H), 3.38 (m, 2H), 6.99 (m, 2H), 7.21 (m, 6H), 7.42 (m, 1H), 7.54 (m, 2H), 7.68 (m, 1H), 8.09 (br t, 1H), 11.60 (br s, 1H). MS (FAB, MH+) 373. Anal. ($C_{23}H_{17}N_2O_2F.0.5 H_2O$) C, H, N.

Example VV

2-Biphenyl-4-yl-1,3,4,5-tetrahydro-azepino[5,4,3-cd]indol-6-one

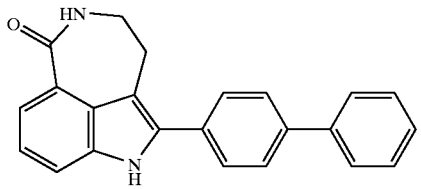

In a manner similar to that described for Compound 12, the tricyclic bromide (150 mg, 0.57 mmol) and 2-Biphenyl-4-boronic acid (123 mg, 0.62 mmol) were coupled to yield 2-Biphenyl-4-yl-1,3,4,5-tetrahydro-azepino[5,4,3-cd]indol-6-one, 87 mg (45%) as a pale yellow solid: m.p. 277–279° C. (dec); $^1$H NMR (300 MHz, $d_6$-DMSO) δ 3.11 (m, 2H), 3.41 (m, 2H), 7.23 (app t, J=7.8 Hz, 1H), 7.40 (m, 1H), 7.51 (app t, J=7.2 Hz, 2H), 7.58 (d, J=8.1 Hz, 1H), 7.77 (m, 7H), 8.10 (br t, 1H), 11.64 (br s, 1H). MS (FAB, MH+) 339 Anal. ($C_{23}H_{18}N_2O.1.15 H_2O$) C, H, N.

Example WW 2-(4-Chloro-3-trifluoromethyl-phenyl)-1,3,4,5-tetrahydro-azepino[5,4,3-cd]indol-6-one

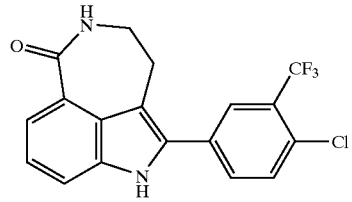

In a manner similar to that described for Compound 12, the tricyclic bromide (100 mg, 0.38 mmol) and 4-chloro-3-trifluoromethyl-phenylboronic acid (150 mg, 0.45 mmol)

were coupled to yield 2-(4-chloro-3-trifluoromethyl-phenyl)-1,3,4,5-tetrahydro-azepino[5,4,3-cd]indol-6-one, 121 mg (88%) as a pale yellow solid: m.p. 118.5–119° C.; $^1$H NMR (300 MHz, d$_6$-DMSO) δ 3.06 (m, 2H), 3.41 (m, 2H), 7.27 (app t, J=7.8 Hz, 1H), 7.60 (dd, J=7.8, 0.9 Hz, 1H), 7.73 (dd, J=7.2, 0.9 Hz, 1H), 7.89 (m, 2H), 8.08 (d, J=1.5 Hz, 1H), 8.14 (br t, 1H), 11.82 (br s, 1H). MS (FAB, MH+) 365. Anal. (C$_{18}$H$_{12}$ClF$_3$N$_2$O.0.45 H$_2$O.0.2 CHCl$_3$) C, H, N.

Example XX

2-Naphthalen-2-yl-1,3,4,5-tetrahydro-azepino[5,4,3-cd]indol-6-one

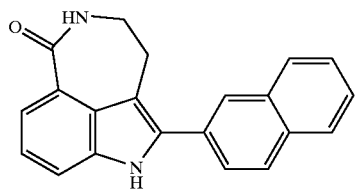

In a manner similar to that described for Compound 12, the tricyclic bromide (300 mg, 1.13 mmol) and 2-naphthaleneboronic acid (214 mg, 1.24 mmol) were coupled to yield 2-Naphthalen-2-yl-1,3,4,5-tetrahydro-azepino[5,4,3-cd]indol-6-one, 130 mg (37%) as a pale yellow solid: m.p. 261–262° C.; $^1$H NMR (300 MHz, d$_6$-DMSO) δ 3.18 (m, 2H), 3.42 (m, 2H), 7.24 (app t, J=7.5 Hz, 1H), 7.58 (m, 3H), 7.72 (dd J=7.5, 0.9 Hz, 1H), 7.84 (dd J=8.4, 1.5 Hz, 1H), 8.07 (m, 5H), 11.74 (br s, 1H). MS (FAB, MH+) 313. Anal. (C$_{21}$H$_{16}$N$_2$O 0.9 H$_2$O) C, H, N.

Example YY

2-[4-(2-Diethylamino-ethyl)-phenyl]-3,4,5,6-tetrahydro-azepino[5,4,3-cd]indol-6-one

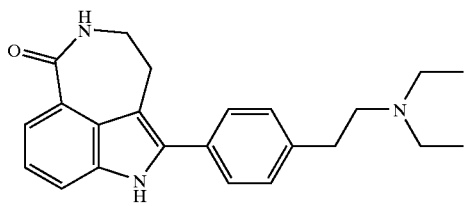

(As described in *Tet. Lett.* 1997 p. 3841) [2-(4-Bromo-phenyl)-ethyl]-diethylamine (256 mg, 1.00 mmol), diboron pinacol ester (279 mg, 1.10 mmol), 1,1'-bis (diphenylphosphino)ferrocenedichloropalladium (24 mg, 0.03 mmol), and potassium acetate (294 mg, 3.00 mmol) were combined in a schlenk tube. The vessel was evacuated then refilled with argon thrice. Degassed DMF (6 mL) was added and the mixture stirred at 80° C. under an argon atmosphere for 2 h. 2-Bromo-3,4,5,6-tetrahydro-azepino[5,4,3-cd]indol-6-one (239 mg, 0.90 mmol), a second portion of 1,1'-bis(diphenylphosphino)ferrocenedichloropalladium (24 mg, 0.03 mmol), and sodium carbonate (2.5 mL of a 2.0 M aqueous solution, 5.00 mmol) were then added and the reaction stirred under an argon atmosphere at 80° C. for another 17 h. The reaction mixture was then poured into 25 mL water then extracted with 25% IPA/CHCl$_3$ (3×20 mL). The combined organic extracts were dried (MgSO$_4$) and concentrated in vacou leaving a brown oil. The crude product was passed through a short silica plug with 25% MeOH/CHCl$_3$ then purified by radial chromatography eluting with 20% MeOH/CHCl$_3$. Crystallization from MeOH/CHCl$_3$/hexanes yielded 2-[4-(2-diethylamino-ethyl)-phenyl]-3,4,5,6-tetrahydro-azepino[5,4,3-cd]indol-6-one, 69 mg (19%) as a white solid: m.p. 224–224.5° C. (dec); $^1$H NMR (300 MHz, d$_6$-DMSO) δ 0.98 (t, J=6.9 Hz, 6H), 2.53 (q, J=7.2 Hz, 4H), 2.69 (m, 4H), 3.04 (m, 2H), 3.37 (m, 2H), 7.19 (t, J=7.8 Hz, 1H), 7.36 (d, J=8.1 Hz, 2H), 7.55 (m, 3H), 7.88 (dd, J=7.5,0.9 Hz, 1H), 8.06 (br t, 1H), 11.51 (br s, 1H). MS (FAB, MH+): 362. Anal. (C$_{23}$H$_{27}$N$_3$O) C, H, N.

Example ZZ

2-[3-(2-Hydroxy-ethyl)-phenyl]-1,3,4,5-tetrahydro-azepino[5,4,3-cd]indol-6-one

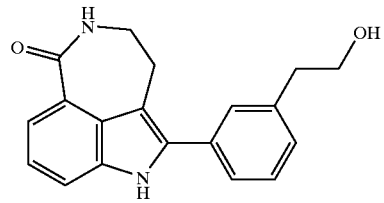

In a manner similar to that described for Example YY, 3-bromophenethyl alcohol (201 mg, 1.00 mmol), diboron pinacol ester (279 mg, 1.10 mmol), 1,1'-bis (diphenylphosphino)ferrocene dichloropalladium (24 mg, 0.03 mmol), and potassium acetate (294 mg, 3.00 mmol), 2-bromo-3,4,5,6-tetrahydro-azepino[5,4,3-cd]indol-6-one (239 mg, 0.90 mmol), a second portion of 1,1'-bis (diphenylphosphino)ferrocenedichloropalladium (24 mg, 0.03 mmol), and sodium carbonate (2.5 mL of a 2.0 M aqueous solution, 5.00 mmol) were reacted to yield 2-[3-(2-hydroxy-ethyl)-phenyl]-1,3,4,5-tetrahydro-azepino[5,4,3-cd]indol-6-one, 135 mg (44%) as an off-white solid: m.p. 187.5–188.5° C.; $^1$H NMR (300 MHz, d$_6$-DMSO) δ 2.82 (t, J=6.9 Hz, 2H), 3.12 (m, 2H), 3.39 (m, 2H), 3.69 (Abq, J=7.2, 5.1 Hz, 2H), 4.71 (t, J=5.1 Hz, 1H), 7.21 (t, J=7.8 Hz, 1H), 7.25 (d, J=7.2 Hz, 1H), 7.49 (m, 4H), 7.68 (dd, J=7.5, 0.9 Hz, 1H), 8.08 (br t, 1H), 11.55 (br s, 1H). MS (FAB, MH+): 307. Anal. (C$_{19}$H$_{18}$N$_2$O$_2$.0.1 H$_2$O) C, H, N.

Example AAA

3-[2-(6-Oxo-3,4,5,6-tetrahydro-1H-azepino[5,4,3-cd]indol-2-yl)-phenyl]-propionic acid methyl ester

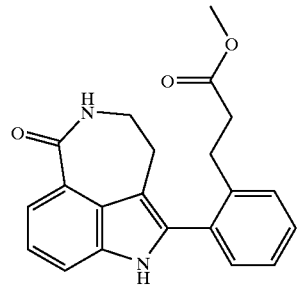

In a manner similar to that described for Example YY, 3-(2-bromo-phenyl)-propionic acid methyl ester (243 mg, 1.00 mmol), diboron pinacol ester (279 mg, 1.10 mmol), 1,1'-bis(diphenyl phosphino)ferrocene dichloropalladium (24 mg, 0.03 mmol), and potassium acetate (294 mg, 3.00 mmol), 2-Bromo-3,4,5,6-tetrahydro-azepino[5,4,3-cd]indol-6-one (239 mg, 0.90 mmol), a second portion of 1,1'-bis(diphenylphosphino)ferrocene dichloropalladium (24 mg, 0.03 mmol), and sodium carbonate (2.5 mL of a 2.0 M aqueous solution, 5.00 mmol) were reacted to yield 3-[2-(6-oxo-3,4,5,6-tetrahydro-1H-azepino[5,4,3-cd]indol-2-yl)-phenyl]-propionic acid methyl ester, 92 mg (29%) as a beige solid: m.p. 201–201.5° C.; $^1$H NMR (300 MHz, $d_6$-DMSO) δ 2.43 (t, J=7.5 Hz, 2H), 2.68 (m, 2H), 2.86 (t, J=8.1 Hz, 2H) 3.38 (m, 2H), 3.47 (s, 3H), 7.20 (t, J=7.8 Hz, 1H), 7.37 (m, 4H), 7.52 (dd, J=7.8, 0.6 Hz, 1H), 7.70 (dd, J=7.5,0.6 Hz, 1H), 8.04 (br t, 1H), 11.41 (br s, 1H). MS (FAB, MH+): 349. Anal. ($C_{21}H_{20}N_2O$·0.3 $CHCl_3$) C, H, N.

Example BBB

2-[2-(3-Hydroxy-propyl)-phenyl]-1,3,4,5-tetrahydro-azepino[5,4,3-cd]indol-6-one

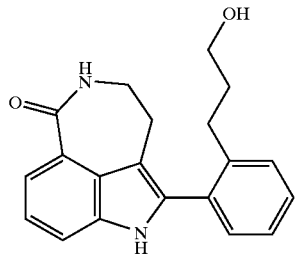

In a manner similar to that described for Example YY, 3-(2-bromo-phenyl)-propan-1-ol (215 mg, 1.00 mmol), diboron pinacol ester (279 mg, 1.10 mmol), 1,1'-bis(diphenyl phosphino) ferrocene dichloropalladium (24 mg, 0.03 mmol), and potassium acetate (294 mg, 3.00 mmol), 2-Bromo-3,4,5,6-tetrahydro-azepino[5,4,3-cd]indol-6-one (239 mg, 0.90 mmol), a second portion of 1,1'-bis(diphenylphosphino)ferrocene dichloropalladium (24 mg, 0.03 mmol), and sodium carbonate (2.5 mL of a 2.0 M aqueous solution, 5.00 mmol) were reacted to yield 2-[2-(3-hydroxy-propyl)-phenyl]-1,3,4,5-tetrahydro-azepino[5,4,3-cd]indol-6-one, 127 mg (44%) as a beige solid: m.p. 233.5–234.5° C.; $^1$H NMR (300 MHz, $d_6$-DMSO) δ 1.53 (m, 2H), 2.61 (t, J=7.8 Hz, 2H), 2.69 (m, 2H), 3.23 (ABq, J=6.6, 5.1 Hz, 2H), 3.37 (m, 2H), 4.39 (t, J=5.1 Hz, 1H), 7.19 (t, J=7.8 Hz, 1H), 7.35 (m, 4H), 7.51 (dd, J=7.8, 0.9 Hz, 1H), 7.70 (dd, J=7.5, 0.9 Hz, 1H), 8.03 (br t, 1H), 11.39 (br s, 1H). MS (FAB, MH+): 321. Anal. ($C_{20}H_{20}N_2O_2$·0.1 $CH_2Cl_2$) C, H, N.

Example CCC 2-(4-Hydroxy-phenyl)-1,3,4,5-tetrahydro-azepino[5,4,3-cd]indol-6-one

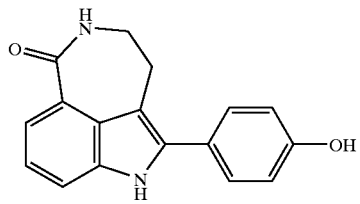

In a manner similar to that described for Compound YY, 4-iodophenol (220 mg, 1.00 mmol), diboron pinacol ester (279 mg, 1.10 mmol), 1,1'-bis(diphenyl phosphino) ferrocenedichloro palladium (24 mg, 0.03 mmol), and potassium acetate (294 mg, 3.00 mmol), 2-bromo-3,4,5,6-tetrahydro-azepino[5,4,3-cd]indol-6-one (239 mg, 0.90 mmol), a second portion of 1,1'-bis(diphenylphosphino) ferrocene dichloropalladium (24 mg, 0.03 mmol), and sodium carbonate (2.5 mL of a 2.0 M aqueous solution, 5.00 mmol) were reacted to yield 2-(4-hydroxy-phenyl)-1,3,4,5-tetrahydro-azepino[5,4,3-cd]indol-6-one, 39 mg (15%) as a beige solid: m.p. 300° C. (dec); $^1$H NMR (300 MHz, $d_6$-DMSO) δ 3.00 (m, 2H), 3.37 (m, 2H), 6.92 (d, J=8.7 Hz, 2H), 7.16 (t, J=7.8 Hz, 1H), 7.49 (m, 3H), 7.65 (dd, J=7.5, 0.9 Hz, 1H), 8.04 (br t, 1H), 9.73 (br s, 1H), 11.40 (br s, 1H). MS (electrospray, MH+): 279. Anal. ($C_{17}H_{14}N_2O_2$) C, H, N.

Example DDD 2-(2-Hydroxy-phenyl)-1,3,4,5-tetrahydro-azepino[5,4,3-cd]indol-6-one

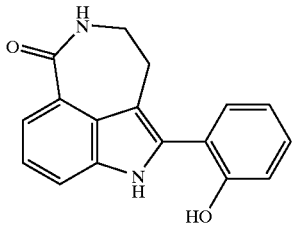

In a manner similar to that described for Example YY, 2-iodophenol (220 mg, 1.00 mmol), diboron pinacol ester (279 mg, 1.10 mmol), 1,1'-bis(diphenyl phosphino) ferrocenedichloro palladium (24 mg, 0.03 mmol), and potassium acetate (294 mg, 3.00 mmol), 2-bromo-3,4,5,6-tetrahydro-azepino[5,4,3-cd]indol-6-one (239 mg, 0.90 mmol), a second portion of 1,1'-bis(diphenylphosphino) ferrocene dichloropalladium (24 mg, 0.03 mmol), and sodium carbonate (2.5 mL of a 2.0 M aqueous solution, 5.00 mmol) were reacted to yield 2-(2-hydroxy-phenyl)-1,3,4,5-tetrahydro-azepino[5,4,3-cd]indol-6-one, 40 mg (15%) as a white solid: m.p. 305° C. (dec); $^1$H NMR (300 MHz, $d_6$-DMSO) δ 2.86 (m, 2H), 3.46 (m, 2H), 6.92 (t, J=7.5 Hz, 1H), 7.00 (d, J=7.8 Hz, 1H), 7.16 (t, J=7.8 Hz, 1H), 7.24 (m, 1H), 7.34 (dd, J=7.5, 1.2 Hz, 1H), 7.55 (d, J=7.8 Hz, 1H), 7.66 (d, J=7.5 Hz, 1H), 8.00 (br t, 1H), 9.84 (br s, 1H), 11.20 (br s, 1H). MS (FAB, MH+): 279. Anal. ($C_{17}H_{14}N_2O_2$·0.44 $CHCl_3$) C, H, N.

Example EEE

6-Oxo-3,4,5,6-tetrahydro-1H-azepino[5,4,3-cd]indole-2-carbonitrile

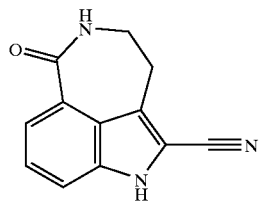

Following a procedure from *JOC* 1998, p. 8224, 2-iodo-1,3,4,5-tetrahydro-azepino[5,4,3-cd]indol-6-one (100 mg, 0.32 mmol), sodium cyanide (31 mg, 0.64 mmol), palladium tetrakis(triphenylphosphine) (19 mg, 0.05 mmol), and copper(I) iodide were combined in a schlenk tube. The vessel was evacuated and refilled with argon gas three times. Degassed propionitrile (2 mL) was added, and the reaction was stirred at 80° C. under an argon atmosphere for 15 h. The reaction mixture was partitioned between water and 25% iPrOH/CHCl$_3$. The layers were separated and the aqueous layer extracted thrice with 25% iPrOH/CHCl$_3$. The combined organic layers were dried (MgSO$_4$) and concentrated in vacuo. The yellow solid was recrystallized from CH$_2$Cl$_2$/MeOH/hexanes to yield 6-oxo-3,4,5,6-tetrahydro-1H-azepino[5,4,3-cd]indole-2-carbonitrile, 38 mg (56%) as a pale yellow solid: m.p. 315° C. (dec); $^1$H NMR (300 MHz, d$_6$-DMSO) δ 3.04 (m, 2H), 3.47 (m, 2H), 7.46 (t, J=7.5 Hz, 1H), 7.64 (dd, J=8.1, 0.9 Hz, 1H), 7.81 (dd, J=7.2, 0.9 Hz, 1H), 8.24 (br t, 1H), 12.44 (br s, 1H). MS (electrospray, [M+Na]+): 234. Anal. (C$_{12}$H$_9$N$_3$O) C, H, N.

Example FFF

6-Oxo-3,4,5,6-tetrahydro-1H-azepino[5,4,3-cd]indole-2-carboxylic acid octyl ester

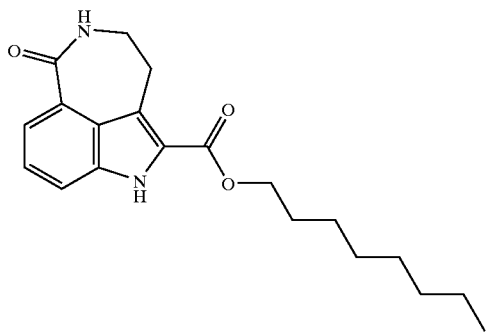

Following a procedure similar to that described for Example MM (Compound 42), 2-iodo-1,3,4,5-tetrahydro-azepino[5,4,3-cd]indol-6-one (330 mg, 1.06 mmol), triethylamine (342 mg, 3.38 mmol), and palladium tetrakis (triphenylphosphine) (61 mg, 0.05 mmol) were reacted in 20 mL 1:1 n-octanol:DMF in a sealed tube under a carbon monoxide atmosphere to yield 6-oxo-3,4,5,6-tetrahydro-1H-azepino[5,4,3-cd]indole-2-carboxylic acid octyl ester, 250 mg (58%), as a white solid: m.p. 170–171° C; $^1$H NMR (300 MHz, d$_6$-DMSO) δ 0.85 (t, J=7.2 Hz, 3H), 1.27 (m, 8H), 1.42 (m, 2H), 1.73 (m, 2H), 3.25 (m, 2H), 3.42 (m, 2H), 4.30 (t, J=6.6 Hz, 3H), 7.38 (app t, J=7.5Hz, 1H), 7.62 (dd, J=8.1,0.9 Hz, 1H), 7.74 (dd, J=7.5,0.9 Hz, 1H), 8.17 (br t, 1H), 11.86 (br s, 1H). MS (FAB, MH+) 343. Anal. (C$_{20}$H$_{26}$N$_2$O$_3$) C, H, N.

Example GGG 2-(4-Chloro-phenyl)-1,3,4,5-tetrahydro-azepino[5,4,3-cd]indol-6-one

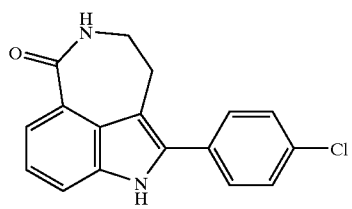

In a manner similar to that described for Compound 12, the tricyclic bromide (300 mg, 1.13 mmol) and 4-chlorophenylboronic acid (195 mg, 1.24 mmol) were coupled to yield 2-(4-chloro-phenyl)-1,3,4,5-tetrahydro-azepino[5,4,3-cd]indol-6-one, 223 mg (66%) as an off-white solid: m.p. 250–252° C.; $^1$H NMR (300 MHz, d$_6$-DMSO) δ 3.04 (m, 2H), 3.39 (m, 2H), 7.23 (app t, J=7.5 Hz, 1H), 7.58 (m, 3H), 7.68 (m, 3H), 8.10 (br t, 1H), 11.66 (br s, 1H). MS (FAB, MH+) 297. Anal. (C$_{17}$H$_{13}$ClN$_2$O.0.8 H$_2$O) C, H, N.

Example HHH

2-Pyridin-3-yl-1,3,4,5-tetrahydro-azepino[5,4,3-cd]indol-6-one

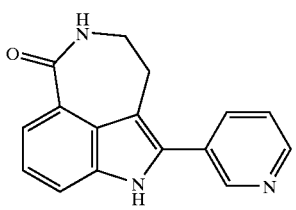

In a manner similar to that described for Compound 12, the tricyclic bromide (300 mg, 1.13 mmol) and 3-pyridylboronic acid (153 mg, 1.24 mmol) were coupled to yield 2-pyridin-3-yl-1,3,4,5-tetrahydro-azepino[5,4,3-cd]indol-6-one, 75 mg (25%) as a light brown solid: m.p. 260.5–262.0° C.; $^1$H NMR (300 MHz, d$_6$-DMSO) δ 3.07 (m, 2H), 3.40 (m, 2H), 7.25 (app t, J=7.8 Hz, 1H), 7.57 (m, 2H), 7.71 (dd, J=7.5, 0.9 Hz, 1H), 8.05 (m, 1H), 8.12 (br t, 1H), 8.59 (m, 1H), 8.88 (m, 1H), 11.75 (br s, 1H). MS (FAB, MH+) 264. Anal. (C$_{16}$H$_{13}$N$_3$O.0.2 H$_2$O) C, H, N.

Example III 2-(2-Methoxy-phenyl)-1,3,4,5-tetrahydro-azepino[5,4,3-cd]indol-6-one

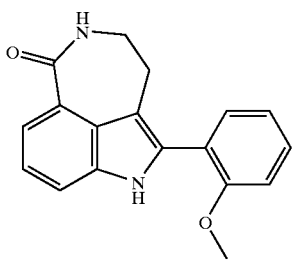

In a manner similar to that described for Compound 12, the tricyclic bromide (300 mg, 1.13 mmol) and 2-methoxyphenylboronic acid (189 mg, 1.24 mmol) were coupled to yield 2-(2-methoxy-phenyl)-1,3,4,5-tetrahydro-azepino[5,4,3-cd]indol-6-one, 177 mg (53%) as a brown solid: m.p. 254–255° C.; $^1$H NMR (300 MHz, d$_6$-DMSO) δ 2.81 (m, 2H), 3.36 (m, 2H), 3.83 (s, 3H), 7.08 (app t, J=7.5 Hz, 1H), 7.17 (m, 2H), 7.43 (m, 2H), 7.54 (dd, J=7.8, 0.6 Hz, 1H), 7.67 (dd, J=7.5, 0.6 Hz, 1H), 8.03 (br t, 1H), 11.27 (br s, 1H). MS (FAB, MH+) 293. Anal. (C$_{18}$H$_{16}$N$_2$O$_2$.0.3 H$_2$O) C, H, N.

Example JJJ

2-Pyridin-4-yl-1,3,4,5-tetrahydro-azepino[5,4,3-cd]indol-6-one

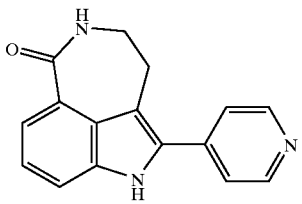

In a manner similar to that described for Compound 12, the tricyclic bromide (300 mg, 1.13 mmol) and 4-pyridylboronic acid (153 mg, 1.24 mmol) were coupled to yield 2-pyridin-4-yl-1,3,4,5-tetrahydro-azepino[5,4,3-cd]indol-6-one, 45 mg (15%) as a beige solid: m.p. 250° C. (dec); $^1$H NMR (300 MHz, d$_6$-DMSO) δ 3.13 (m, 2H), 3.41 (m, 2H), 7.29 (app t, J=7.8 Hz, 1H), 7.63 (m, 3H), 7.72 (dd, J=7.2, 0.9 Hz, 1H), 8.14 (br t, 1H), 8.69 (d, J=6.0 Hz, 2H), 11.82 (br s, 1H). MS (FAB, MH+) 364. Anal. (C$_{16}$H$_{13}$N$_3$O) C, H, N.

Example KKK

6-Oxo-3,4,5,6-tetrahydro-1H-azepino[5,4,3-cd]indole-2-carboxylic acid sodium salt

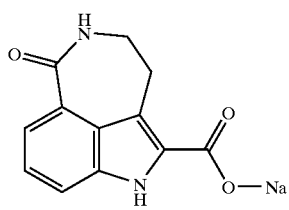

In an attempt to form the piperazine amide, 6-oxo-3,4,5,6-tetrahydro-1H-azepino[5,4,3-cd]indole-2-carboxylic acid methyl ester (100 mg, 0.41 mmol) was dissolved in 1 mL piperazine. The yellow solution was stirred under argon at 110° C. for 18 h. The reaction mixture was partitioned between saturated NaHCO$_3$ and 25% iPrOH/CHCl$_3$. The layers were separated and the aqueous layer extracted once with 25% iPrOH/CHCl$_3$. The combined organic layers were dried (MgSO$_4$) and concentrated in vacuo leaving ca. 3 mg of yellow solid. After standing overnight at room tempereature, a pale yellow solid crystallized from the aqueous layer 80 mg (78%). The compound was identified as the sodium salt of 6-oxo-3,4,5,6-tetrahydro-1H-azepino[5,4,3-cd]indole-2-carboxylic acid: m.p. 310° C (dec); $^1$H NMR (300 MHz, d$_6$-DMSO) δ 3.20 (m, 2H), 3.41 (m, 2H), 7.11 (app t, J=7.8 Hz, 1H), 7.50 (dd, J=8.1, 0.9 Hz, 1H), 7.60 (dd, J=7.5, 0.9 Hz, 1H), 7.96 (br t, 1H), 11.00 (br s, 1H). MS (electrospray, [M−Na]$^-$) 229. Anal. (C$_{12}$H$_9$N$_2$O$_3$Na.0.5 H$_2$O) C, H, N.

Example LLL 2-(2-Methylsulfanyl-phenyl)-1,3,4,5-tetrahydro-azepino[5,4,3-cd]indol-6-one

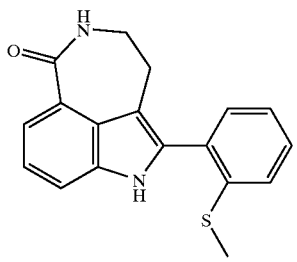

In a manner similar to that described for Compound 12, the tricyclic bromide (530 mg, 2.00 mmol) and 2-thioanisole boronic acid (370 mg, 2.20 mmol) were coupled to yield 2-(2-methylsulfanyl-phenyl)-1,3,4,5-tetrahydro-azepino[5,4,3-cd]indol-6-one, 264 mg (43%) as an off-white solid: m.p. 271–272° C.; $^1$H NMR (300 MHz, d$_6$-DMSO) δ 2.39 (s, 3H), 2.73 (m, 2H), 3.37 (m, 2H), 7.23 (m, 2H), 7.37 (m, 2H), 7.49 (m, 2H), 7.70 (d, J=7.2 Hz, 1H), 8.05 (br t, 1H), 11.41 (br s, 1H). MS (FAB, MH+) 309. Anal. (C$_{18}$H$_{16}$N$_2$OS) C, H, N.

Example MMM

2-[4-(2-Pyrrolidin-1-yl-ethyl)-phenyl]-1,3,4,5-tetrahydro-azepino[5,4,3-cd]indol-6-one

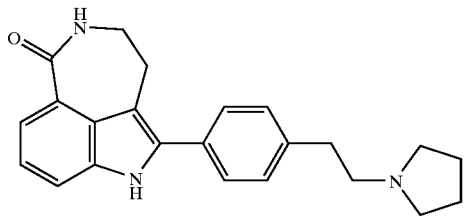

In a manner similar to that described for 2-[4-(2-diethylamino-ethyl)-phenyl]-3,4,5,6-tetrahydro-azepino[5,4,3-cd]indol-6-one (Example YY), the tricyclic bromide (198 mg, 0.75 mmol) and 1-[2-(4-bromo-phenyl)-ethyl]-pyrrolidine were coupled to yield 2-[4-(2-pyrrolidin-1-yl-ethyl)-phenyl]-1,3,4,5-tetrahydro-azepino[5,4,3-cd]indol-6-one, 160 mg (59%) as a beige solid: m.p. 228–229° C. (dec); $^1$H NMR (300 MHz, d$_6$-DMSO) δ 1.69 (m, 4H), 2.51 (m, 4H), 2.67 (m, 2H), 2.81 (m, 2H), 3.05 (m, 2H), 3.39 (m, 2H), 7.20 (t, J=7.8 Hz, 1H), 7.39 (d, J=8.1 Hz, 2H), 7.56 (m, 3H), 7.68 (d, J=7.5 Hz, 1H), 8.08 (br t, 1H), 11.31 (br s, 1H). MS (FAB, MH+): 360. Anal. (C$_{23}$H$_{25}$N$_3$O) C, H, N.

Example NNN

N-[4-Fluoro-2-(6-oxo-3,4,5,6-tetrahydro-1H-azepino[5,4,3-cd]indol-2-yl)-phenyl]-acetamide

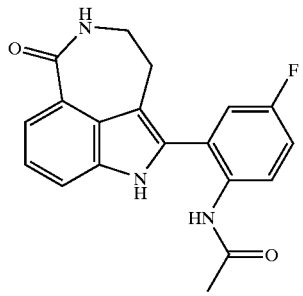

In a manner similar to that described for 2-[4-(2-diethylamino-ethyl)-phenyl]-3,4,5,6-tetrahydro-azepino[5,4,3-cd]indol-6-one (Example YY), the tricyclic bromide (300 mg, 1.13 mmol) and N-(2-bromo-4-fluoro-phenyl)-acetamide (276 mg, 1.19 mmol) were coupled to yield N-[4-fluoro-2-(6-oxo-3,4,5,6-tetrahydro-1H-azepino[5,4,3-cd]indol-2-yl)-phenyl]-acetamide, 83 mg (22%) as a beige solid: m.p. 260–261° C. (dec); $^1$H NMR (300 MHz, $d_6$-DMSO) δ 1.97 (s, 3H), 2.66 (m, 2H), 3.33 (m, 2H), 7.25 (m, 3H), 7.56 (dd, J=7.5, 0.6 Hz, 1H), 7.70 (dd, J=7.2, 0.6 Hz, 1H), 7.76 (m, 1H), 8.04 (br t, 1H), 11.50 (br s, 1H). MS (FAB, MH+): 338. Anal. ($C_{16}H_{19}FN_3O_2 \cdot 0.16\ H_2O$) C, H, N.

Example OOO

6-Oxo-3,4,5,6-tetrahydro-1H-azepino[5,4,3-cd]indole-2-carboxylic acid methylamide

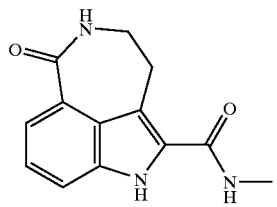

6-Oxo-3,4,5,6-tetrahydro-1H-azepino[5,4,3-cd]indole-2-carboxylic acid methyl ester (50 mg, 0.20 mmol) was suspended in 1 mL of a 33% solution of methylamine in methanol. The suspension was stirred at room temperature for 21 h. Another 2 mL 33% methylamine in methanol was added and the resulting solution stirred another 8 h at room temperature then 15 h at 30° C. The reaction mixture was concentrated in vacuo leaving a yellow solid which was crystallized from DMF/MeOH/CHCl$_3$ to yield 6-oxo-3,4,5,6-tetrahydro-1H-azepino[5,4,3-cd]indole-2-carboxylic acid methylamide, 36 mg (72%) as a yellow solid: m.p. 321–322° C. (dec); $^1$H NMR (300 MHz, $d_6$-DMSO) δ 2.81 (s, 3H), 3.15 (m, 2H), 3.40 (m, 2H), 7.32 (app t, J=7.8 Hz, 1H), 7.61 (d, J=8.1Hz, 1H), 7.74 (d, J=7.5 Hz, 1H), 7.95 (br q, 1H), 8.09 (br t, 1H), 11.46 (br s, 1H). MS (electrospray, [M+Na]$^+$) 266. Anal. ($C_{13}H_{13}N_3O_2 \cdot 0.4\ H_2O$) C, H, N.

Example PPP 2-(4-Dimethylaminomethyl-3-fluoro-phenyl)-1,3,4,5-tetrahydro-azepino[5,4,3-cd]indol-6-one

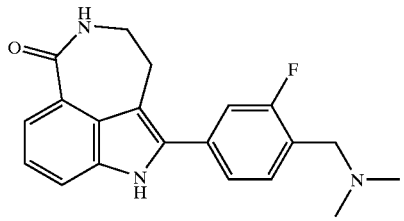

2-Fluoro-4-(6-oxo-3,4,5,6-tetrahydro-1H-azepino[5,4,3-cd]indol-2-yl)-benzaldehyde (72 mg, 0.23 mmol. Prepared via the standard two-step, one-pot suzuki coupling of the tricyclic bromide and 4-bromo-2-fluoro-benzaldehyde as described for Example YY) was dissolved in 2 mL 2.0 M dimethylamine in methanol. The orange solution was stirred at room temperature 10 min. The reaction was then cooled to 0° C. and a solution containing zinc chloride (17 mg, 0.13 mmol) and sodium cyanoborohydride (16 mg, 0.26 mmol) in 1 mL methanol, was added dropwise. The pH was adjusted to ca. 3 with concentrated HCl. The reaction was stirred for one hour as the temperature gradually warmed to room temperature. The reaction was partitioned between CHCl$_3$ and water. The pH of the aqueous layer was adjusted to ca. 13 with solid KOH. The layers were separated, and the aqueous layer extracted with 25% iPrOH/CHCl$_3$. The combined organic layers were dried (MgSO$_4$) then concentrated in vacuo. Radial chromatography (eluting with 5% MeOH/CHCl$_3$) then crystallization from CH$_2$Cl$_2$/hexanes yielded 2-(4-dimethylaminomethyl-3-fluorophenyl)-1,3,4,5-tetrahydro-azepino[5,4,3-cd]indol-6-one, 60 mg (76%) as a yellow solid.: m.p. 221.5–222.5° C.; $^1$H NMR (300 MHz, $d_6$-DMSO) δ 2.19 (s, 6H), 3.08 (m, 2H), 3.39 (m, 2H), 3.50 (s, 2H), 7.23 (app t, J=7.8 Hz, 1H), 7.50 (m, 4H), 7.69 (d, J=7.5 Hz, 1H) 8.10 (br t, 1H), 11.62 (br s, 1H). MS (FAB, MH+) 338. Anal. ($C_{20}H_{20}FN_3O$) C, H, N.

Example QQQ 2-(3-Fluoro-4-pyrrolidin-1-ylmethyl-phenyl)-1,3,4,5-tetrahydro-azepino[5,4,3-cd]indol-6-one

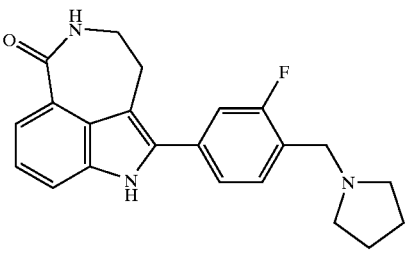

In a manner similar to that described for as described for Example YY, the tricyclic bromide (1.00 g, 3.77 mmol) and 1-(4-bromo-2-fluoro-benzyl)-pyrrolidine (1.07 g, 4.19 mmol) were coupled to yield 2-(3-fluoro-4-pyrrolidin-1-ylmethyl-phenyl)-1,3,4,5-tetrahydro-azepino[5,4,3-cd]indol-6-one, 150 mg (11%) as a beige solid: m.p. 139–140° C. (dec); $^1$H NMR (300 MHz, $d_6$-DMSO) δ 1.71 (m, 4H), 2.50 (m, 4H, obscured by solvent), 3.07 (m, 2H), 3.40 (m, 2H), 3.68 (s, 2H), 7.23 (t, J=7.8 Hz, 1H), 7.45 (m, 2H), 7.55

(m, 2H), 7.70 (dd, J=7.5, 0.6 Hz, 1H), 8.07 (br t, 1H), 11.59 (br s, 1H). MS (electrospray, MH+) 364. Anal. ($C_{22}H_{22}FN_3O.0.55 H_2O$) C, H, N.

Example RRR

2-Biphenyl-3-yl-1,3,4,5-tetrahydro-azepino[5,4,3-cd]indol-6-one

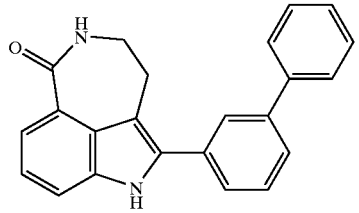

In a manner similar to that described for Compound 12, the tricyclic bromide (300 mg, 1.13 mmol) and biphenyl-3-boronic acid (213 mg, 0.83 mmol) were coupled to yield 2-biphenyl-3-yl-1,3,4,5-tetrahydro-azepino[5,4,3-cd]indol-6-one, 116 mg (30%) as an off-white crystalline solid: m.p. 160–163° C.; $^1$H NMR (300 MHz, $d_6$-DMSO) δ 3.13 (m, 2H), 3.42 (m, 2H), 7.24 (app t, J=7.8 Hz, 1H), 7.42 (m, 1H), 7.61 (m, 7H), 7.79 (m, 2H), 7.94 (b s, 1H), 8.10 (br t, 1H), 11.67 (br s, 1H). MS (FAB, MH+) 339. Anal. ($C_{23}H_{18}N_2O$) C, H, N.

Example SSS 2-(5-Chloro-2-methoxy-phenyl)-3,4,5,6-tetrahydro-azepino[5,4,3-cd]indol-6-one

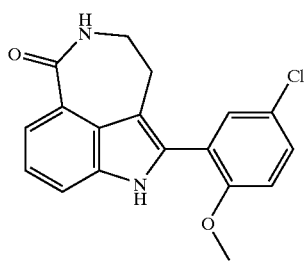

In a manner similar to that described for Compound 12, the tricyclic bromide (129 mg, 0.49 mmol) and 5-chloro-2-methoxy-phenylboronic acid (100 mg, 0.54 mmol) were coupled to yield 2-(5-chloro-2-methoxy-phenyl)-3,4,5,6-tetrahydro-azepino[5,4,3-cd]indol-6-one, 100 mg (63%) as an off-white solid: m.p. 160–162° C.; $^1$H NMR (300 MHz, $d_6$-DMSO) δ 2.81 (m, 2H), 3.34 (m, 2H), 3.84 (s, 3H), 7.20 (m, 2H), 7.46 (m, 2H), 7.55 (d, J=7.8 Hz, 1H), 7.68 (d, J=7.5 Hz, 1H), 8.05 (br t, 1H), 11.37 (br s, 1H). MS (FAB, MH+): 327. Anal. ($C_{18}H_{15}ClN_2O_2$) C, H, N, Cl.

Example TTT 1,3,4,5,1',3',4',5'-Octahydro-[2,2']bi[azepino[5,4,3-cd]indolyl]-6,6'-dione

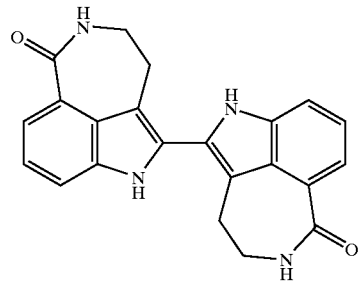

The title compound was isolated as a by-product of the coupling of the tricyclic bromide (642 mg, 2.42 mmol) under the conditions described for Example YY, 27 mg (6%) isolated as a yellow solid: m.p. <400° C. (dec); $^1$H NMR (300 MHz, $d_6$-DMSO) δ 2.97 (m, 4H), 3.39 (m, 4H), 7.26 (t, J=7.8 Hz, 2H), 7.59 (dd, J=8.1, 0.9 Hz, 2H), 7.72 (dd, J=7.5, 0.9 Hz, 2H), 8.12 (br t, 2H), 11.50 (br s, 2H). MS (electrospray, MH+): 372. Anal. ($C_{22}H_{18}N_4O_2.0.25 H_2O$) C, H. N.

Example UUU 2-(3-Amino-phenylethynyl)-1,3,4,5-tetrahydro-azepino[5,4,3-cd]indol-6-one

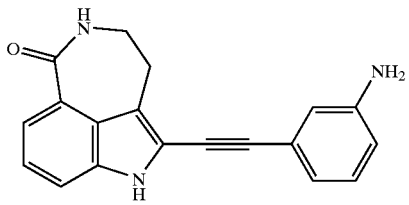

In a manner similar to that described for Example N, Compound 17,3-ethynyl-analine (129 mg, 1.10 mmol) was coupled to 2-iodo-1,3,4,5-tetrahydro-azepino[5,4,3-cd]indol-6-one (312 mmol, 1.00 mmol) to yield 2-(3-aminophenylethynyl)-1,3,4,5-tetrahydro-azepino[5,4,3-cd]indol-6-one, 250 mg (83%) as a pale yellow solid: m.p. 261–262° C. (dec); $^1$H NMR (300 MHz, $d_6$-DMSO) δ 3.00 (m, 2H), 3.45 (m, 2H), 5.31 (br s, 2H), 6.63 (m, 1H), 6.71 (m, 1H), 6.76 (m, 1H), 7.08 (app t, J=7.8 Hz, 1H), 7.26 (app t, J=7.8 Hz, 1H), 7.48 (dd, J=8.1, 0.9 Hz, 1H), 7.70 (dd, J=7.5, 0.6 Hz, 1H), 8.09 (br t, 1H), 11.75 (br s, 1H). MS (electrospray, MH+) 302. Anal. ($C_{19}H_{15}N_3O.0.15 H_2O$) C, H, N.

Example VVV 2-(1H-Indol-5-yl)-1,3,4,5-tetrahydro-azepino[5,4,3-cd]indol-6-one

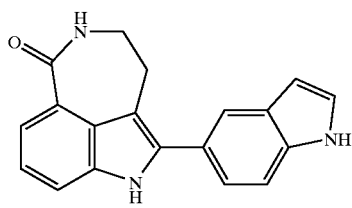

In a manner similar to that described for Compound 12, the tricyclic bromide (530 mg, 2.00 mmol) and indole-5-boronic acid (354 mg, 2.20 mmol) were coupled to yield 2-(1H-indol-5-yl)-1,3,4,5-tetrahydro-azepino[5,4,3-cd]indol-6-one, 396 mg (66%) as a beige solid: m.p. 315–317° C. (dec); $^1$H NMR (300 MHz, $d_6$-DMSO) δ 3.10 (m, 2H), 3.41 (m, 2H), 6.54 (m, 1H), 7.17 (t, J=7.8 Hz, 1H), 7.42 (m, 2H), 7.55 (m, 2H), 7.68 (d, J=7.5 Hz, 1H), 7.83 (br s, 1H), 8.05 (br t, 1H), 11.26 (br s, 1H), 11.48 (br s, 1H). MS (electrospray, MH+) 302. Anal. ($C_{19}H_{15}N_3O \cdot 0.25 H_2O$) C, H, N.

Example WWW 4-(6-Oxo-3,4,5,6-tetrahydro-1H-azepino[5,4,3-cd]indol-2-yl)-benzoic acid

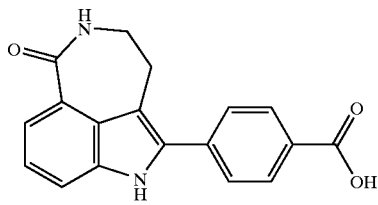

In a manner similar to that described for Compound 12, the tricyclic bromide (530 mg, 2.00 mmol) and 4-carboxyphenylboronic acid (365 mg, 2.20 mmol) were coupled to yield 4-(6-oxo-3,4,5,6-tetrahydro-1H-azepino[5,4,3-cd]indol-2-yl)-benzoic acid, 340 mg (56%) as a pale yellow solid: m.p. 345.5–346.5° C. (dec); $^1$H NMR (300 MHz, $d_6$-DMSO) δ 3.10 (m, 2H), 3.40 (m, 2H), 7.25 (t, J=7.8 Hz, 1H), 7.59 (dd, J=8.1, 0.9 Hz, 1H), 7.70 (dd, J=7.5, 0.6 Hz, 1H), 7.78 (m, 2H), 8.10 (m, 3H), 11.73 (br S, 1H), 13.00 (br s, 1H). MS (electrospray, MH+) 307. Anal. ($C_{18}H_{14}N_2O_3 \cdot 0.9 H_2O$) C, H, N.

Example XXX

6-Oxo-3,4,5,6-tetrahydro-1H-azepino[5,4,3-cd]indole-2-carboxylic acid

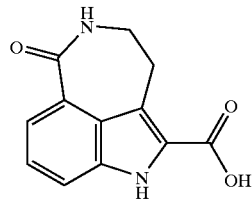

6-Oxo-3,4,5,6-tetrahydro-1H-azepino[5,4,3-cd]indole-2-carboxylic acid octyl ester (Example FFF) (350 mg, 1.02 mmol) and lithium hydroxide (122 mg, 5.11 mmol) were dissolved in 10 mL 2:1 methanol:water and stirred at room temperature for 24 h. The reaction mixture was diluted with water then washed twice with dichloromethane. The aqueous solution was acidified to ca. pH 2 with conc. HCl. The white precipitate was collected by filtration, washed with water, and dried in vacuo to yield 6-oxo-3,4,5,6-tetrahydro-1H-azepino[5,4,3-cd]indole-2-carboxylic acid, 235 mg (99%) as a white solid: m.p. 298–299° C. (dec); $^1$H NMR (300 MHz, $d_6$-DMSO) δ 3.17 (m, 2H), 3.41 (m, 2H), 7.35 (t, J=7.8 Hz, 1H), 7.59 (d, J=8.1 Hz, 1H), 7.73 (d, J=7.5 Hz, 1H), 8.14 (br t, 1H), 11.77 (br s, 1H), 13.14 (br s, 1H). MS (electrospray, MH+): 231. Anal. ($C_{12}H_{10}N_2O_3 \cdot 1.0 H_2O$) C, H, N.

Example YYY

6-Oxo-3,4,5,6-tetrahydro-1H-azepino[5,4,3-cd]indole-2-carboxylic acid (4-fluoro-phenyl)-amide

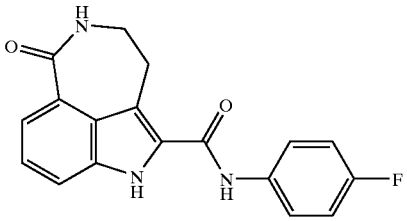

6-Oxo-3,4,5,6-tetrahydro-1H-azepino[5,4,3-cd]indole-2-carboxylic acid (100 mg, 0.43 mmol), 4-fluoroaniline (48 mg, 0.43 mmol), and diisoprophylethylamine (168 mg, 1.30 mmol) were dissolved in 5 mL dry DMF. HATU (173 mg, 0.46 mmol) was added and the resulting mixture stirred at room temperature under argon for 3 d. The reaction mixture was partitioned between water and 25% iPrOH/CHCl$_3$. The layers were separated, and the aqueous layer extracted thrice with 25% iPrOH/CHCl$_3$. The combined organic layers were dried (MgSO$_4$) and concentrated in vacuo leaving an off-white solid which was recrystallized from chloroform/methanol to yield 6-oxo-3,4,5,6-tetrahydro-1H-azepino[5,4,3-cd]indole-2-carboxylic acid (4-fluoro-phenyl)-amide, 70 mg (50%) as a pale yellow solid: m.p. 330–332° C. (dec); $^1$H NMR (300 MHz, $d_6$-DMSO) δ 3.28 (m, 2H), 3.42 (m, 2H), 7.22 (m, 2H), 7.35 (app t, J=7.8 Hz, 1H), 7.65 (dd, J=7.8, 0.6 Hz, 1H), 7.77 (m, 3H), 8.16 (br t, 1H), 10.08 (br s, 1H), 11.81 (br s, 1H). MS (electrospray, MH+) 324. Anal. ($C_{18}H_{14}FN_3O_2 \cdot 0.4 H_2O$) C, H, N.

Example ZZZ (4-Chloro-phenyl)-1,5-dihydro-[1,2]diazepino[4,5,6-cd]indol-6-one

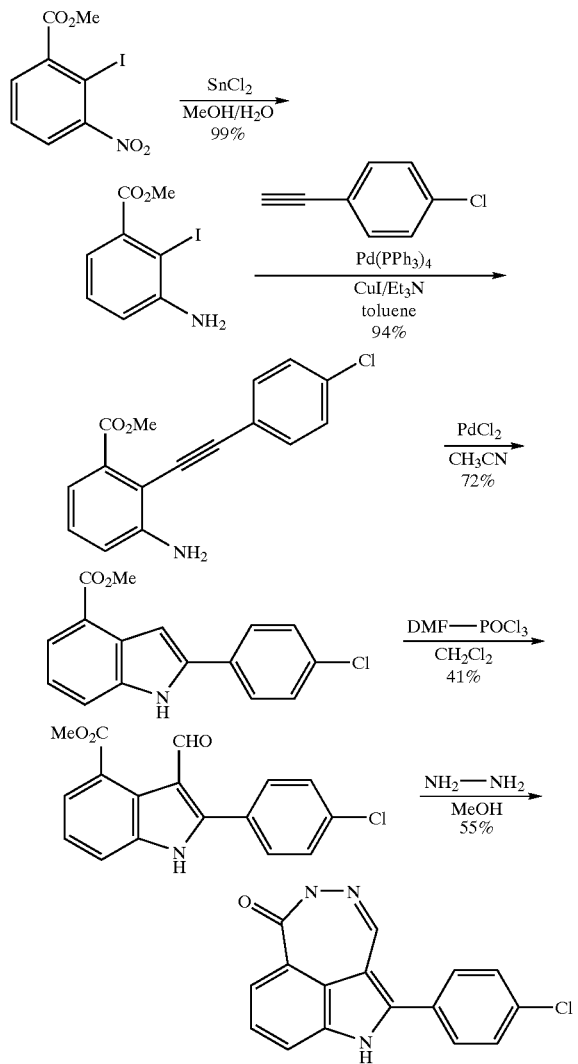

2-Iodo-3-nitro-benzoic acid methyl ester: 2-iodo-3-nitro-benzoic acid (61 g, 208 mmol, prepared as described in *Org. Syn.* Coll. Vol. I, 56–58, and 125–127), sulfuric acid (40.8 g, 416 mmol), and trimethyl orthoformate (88.4 g, 833 mmol) were dissolved in 500 mL dry MeOH. The reaction was refluxed under argon for 20 h. The reaction mixture was concentrated to 100 mL then partitioned between saturated NaHCO$_{3(aq)}$ and CH$_2$Cl$_2$. The layers were separated and the aqueous layer extrated three times with CH$_2$Cl$_2$. The combined organic layers were dried (MgSO$_4$) and concentrated in vacuo. The yellow solid was crystallized from CH$_2$Cl$_2$/hexanes yielding 2-iodo-3-nitro-benzoic acid methyl ester, 57.8 g (90%) as a yellow solid: m.p.64.0–64.5° C.; 1H NMR (300 MHz, CDCl$_3$) δ 3.99 (s, 3H), 7.54 (app t, J=7.8 Hz, 1H), 7.70 (dd, J=8.1, 1.8 Hz, 1H), 7.77 (dd, J=7.8, 1.8 Hz, 1H).

3-Amino-2-iodo-benzoic acid methyl ester: 2-Iodo-3-nitro-benzoic acid methyl ester (1.00 g, 3.26 mmol) was dissolved in 15 mL MeOH. Tin (II) chloride (2.78 g, 14.66 mmol) and water (0.35 g, 19.54 mmol) were added and the yellow solution stirred at room temperature for 20 h. Celite was added to the solution followed by 10 mL 3 M NaOH. The suspension was diluted with MeOH and the precipitate filtered off. The filter cake was washed with three portions boiling CH$_2$Cl$_2$. The layers were separated and the aqueous layers extracted once with CH$_2$Cl$_2$. The combined organic layers were dried (MgSO$_4$) and concentrated in vacuo to yield 2-iodo-3-nitro-benzoic acid methyl ester, 0.89 g (99%), as a clear oil. $^1$H NMR (300 MHz, d$_6$-DMSO) δ 3.81 (s, 3H), 5.52 (br s, 2H), 6.72 (dd, J=7.5, 1.2 Hz, 1H), 6.87 (dd, J=7.5, 1.2Hz, 1H), 6.87 (dd, J=7.8, 1.2 Hz, 1H), 7.12 (app t, J=7.5 Hz, 1H). MS (electrospray, MH+) 278.

3-Amino-2-(4-chloro-phenylethynyl)-benzoic acid methyl ester: 2-iodo-3-nitro-benzoic acid methyl ester (0.79 g, 2.84 mmol), 1-chloro-4-ethynylbenzene (0.41 g, 2.99 mmol), palladium tetrakis(triphenylphosphine) (0.16 g, 0.14 mmol), copper (I) iodide (0.03 g, 0.14 mmol), and triethylamine (1.44 g, 14.19 mmol) were dissolved in 15 mL toluene. Argon was bubbled through the resulting solution for 15 min. The reaction was stirred under argon at 80° C. for 2 h and 20 min. The reaction mixture was then washed once with water, dried (MgSO$_4$), and concentrated in vacuo. The orange oil was purified by flash chromatography eluting with 50 to 100% CHCl$_3$/hexanes to yield 3-amino-2-(4-chloro-phenylethynyl)-benzoic acid methyl ester, 0.76 g (94%) as a yellow oil. $^1$H NMR (300 MHz, d$_6$-DMSO) δ 3.84 (s, 3H), 5.84 (br s, 2H), 6.97 (dd, J=8.1, 1.3 Hz, 1H), 7.05 (dd, J=7.5, 1.2 Hz, 1H), 7.17 (app t, J=7.5 Hz, 1H), 7.49 (d, J=8.7 Hz, 2H), 7.63 (d, J=8.7 Hz, 2H). MS (electrospray, MH+) 286.

2-(4-Chloro-phenyl)-1H-indole-4-carboxylic acid methyl ester: 3-amino-2-(4-chloro-phenylethynyl)-benzoic acid methyl ester (0.73 g, 2.54 mmol) and palladium (II) chloride (23 mg, 0.13 mmol) were combined in 10 mL acetonitrile. The yellow solution was stirreed under argon at 75° C. for 17 h. The solvent was removed in vacuo leaving an orange solid which was purified by flash chromatography eluting with 50 to 100% CH—Cl$_3$/hecanes. 2-(4-chloro-henyl)-1H-indole-4-carboxylic acid methyl ester; 0.53 g (72%) was isolated as an off-white solid: m.p. 150.0–151.5° C.; $^1$H NMR (300 MHz, d$_6$-DMSO) δ 3.93 (s, 3H), 7.23 (app t, J=7.8 Hz, 1H), 7.41 (d, J=1.8 Hz, 1H), 7.57 (d, J=8.7 Hz, 2H), 7.68 (d, J=7.8 Hz, 1H), 7.75 (dd, J=7.5, 0.9 Hz, 1H), 7.95 (d, J=8.7 Hz, 2H), 11.99 (br s, 1H). HRMS (MALDI, MH+) Calcd for C$_{16}$H$_{12}$ClNO$_2$: 286.0635. Found: 286.0631.

2-(4-Chloro-phenyl)-3-formyl-1H-indole-4-carboxylic acid methyl ester: Phosphorous oxychloride (0.42 g, 2.71 mmol) was added to DMF (0.99 g, 13.57 mmol) at 0° C. The resulting colorless solution was added dropwise to a solution of 2-(4-chloro-phenyl)-1H-indole-4-carboxylic acid methyl ester (0.52 g, 1.81 mmol) in 10 mL dry CH$_2$Cl$_2$ at 0° C. The reaction was stirred at 0° C. for 10 min then quenched by addition of 5 mL 2 M NaOAc$_{(aq)}$. The layers were separated and the aqueous layer extracted once with CH2Cl2. The combined organic layers were dried (MgSO$_4$) then concentrated in vacuo leaving anorange oil which crystallized on standing. The crystals were rinsed with CH$_2$Cl$_2$ then dried in vacuo to yield 2-(4-chloro-phenyl)-3-formyl-1H-indole-4-carboxylic acid methyl ester, 231 mg (41%) as an off-white solid: m.p. 221–222° C.; $^1$H NMR (300 MHz, d$_6$-DMSO) δ 3.93 (s, 3H), 7.49 (app t, J=7.5 Hz, 1H), 7.71 (m, 4H), 7.94 (d, J=7.8 Hz, 2H), 9.71 (s, 1H), 13.67 (br s, 1H). MS (electrospray, [M–H]) 312.

(4-Chloro-phenyl)-1,5-dihydro-[1,2]diazepino[4,5,6-cd]indol-6-one:

2-(4-chloro-phenyl)-3-formyl-1H-indole-4-carboxylic acid methyl ester (100 mg, 0.32 mmol) was dissolved in 5 mL MeOH. Hydrazine (30 mg, 0.92 mmol) was added causing the immediate precipitate. Acetic acid (13 mg, 0.22 mmol) was added and the yellow suspension refluxed for 1.5 h. The yellow solid was collected by filtration, rinsed once with MeOH, then dried in vacuo to give (40chloro-phenyl)-1,5-dihydro-[1,2]diazepino[4,5,6-cd]indol-6-one, 55 mg (59%) as a bright yellow solid: m.p. 324.0–324.5° C. (dec); $^1$H NMR (300 MHz, $d_6$-DMSO) δ 7.23 (app t, J=7.8 Hz, 1H), 7.49 (s, 1H), 7.55 (m, 2H), 7.65 (d, J=8.7 Hz, 2H), 7.71 (d, J=Hz, 2H), 10.36 (s, 1H), 12.32 (br s, 1H). HRMS (MALDI, MH+) Calcd for $C_{16}H_{10}ClN_3O$: 296.0591. Found: 296.0586. Anal. ($C_{16}H_{10}ClN_3O$.0.5 $H_2O$)C, H, N.

Example AAAA 2-(4-Fluoro-phenyl)-1,5-dihydro-[1,2]diazepino[4,5,6-cd]indol-6-one

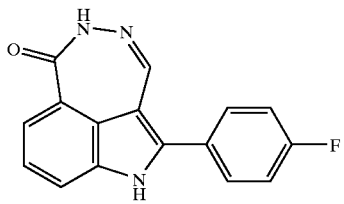

In a manner similar to that described for Example ZZZ, 2-(4-fluoro-phenyl)-3-formyl-1H-indole-4-carboxylic acid methyl ester (145 mg, 0.49 mmol) was condensed with hydrazine (45 mg, 1.41 mmol) to give 2-(4-fluoro-phenyl)-1,5-dihydro-[1,2]diazepino[4,5,6-cd]indol-6-one, 120 mg (88%) as a bright yellow solid: m.p. 340–341° C. (dec); $^1$H NMR (300 MHz, $d_6$-DMSO) δ 7.22 (app t, J=7.8 Hz 1H), 7.43 (m, 3H), 7.54 (m, 2H), 7.73 (m, 2H), 10.33 (s, 1H), 12.23 (br s, 1H). MS (electrospray, MH+) 280. Anal. ($C_{16}H_{10}FN_3O$) C, H, N.

Example BBBB

2-Thiophen-2-yl-1,3,4,5-tetrahydro-azepino[5,4,3-cd]indol-6-one

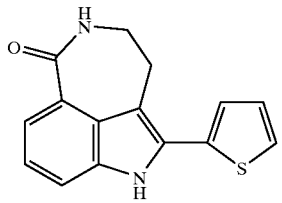

In a manner similar to that described for Compound 12, the tricyclic bromide (300 mg, 1.13 mmol) and thiophene-2-boronic acid (159 mg, 1.24 mmol) were coupled to yield 2-thiophen-2-yl-1,3,4,5-tetrahydro-azepino[5,4,3-cd]indol-6-one, 171 mg (56%) as a beige solid: m.p. 220.5–222.5° C.; $^1$H NMR (300 MHz $d_6$-DMSO) δ 3.08 (m, 2H), 3.48 (m, 2H), 7.23 (m, 2H), 7.52 (m, 2H), 7.69 (m, 2H), 8.05 (br t, 1H), 11.60 (br s, 1H). MS (electrospray, MH+) 269. Anal. ($C_{15}H_{12}N_2$)S.0.8 $H_2O$) C, H, N.

Example CCCC

2-Thiophen-3-yl-1,3,4,5-tetrahydro-azepino[5,4,3-cd]indol-6-one

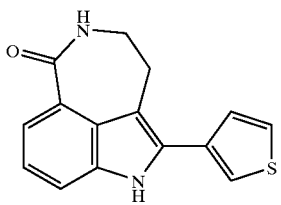

In a manner similar to that described for Compound 12, the tricyclic bromide (300 mg, 1.13 mmol) and thiophene-3-boronic acid (159 mg, 1.24 mmol) were coupled to yield 2-thiophen-3-yl-1,3,4,5-tetrahydro-azepino[5,4,3-cd]indol-6-one, 249 mg (82%) as a beige solid: m.p. 255–256° C.; $^1$H NMR (300 MHz, $d_6$-DMSO) δ 3.08 (m, 2H), 3.43 (m, 2H), 7.19 (t, J=7.8 Hz, 1H), 7.54 (m, 2H), 7.67 (dd, J=7.5, 0.9 Hz, 1H), 7.74 (m, 1H), 7.78 (m, 1H), 8.03 (br t, 1H), 11.49 (br s, 1H). MS (electrospray, MH+) 269. Anal. ($C_{15}H_{12}N_2OS$.0.35 $H_2O$) C, H, N, S.

Example DDDD 2-(1H-Pyrrol-2-yl)-1,3,4,5-etatrhydro-azepino[5,4,3-cd]indol-6-one

In a manner similar to that described for Compound 12, the tricyclic bromide (300 mg, 1.13 mmol) and 1-)t-butoxycarbonyl)pyrrole-2-boronic acid (263 mg, 1.24 mmol) were coupled with concomitant removal of the BOC group to yield 2-(1H-pyrrol-2-yl)-1,3,4,5-tetrahydro-azepino[5,4,3-cd]indol-6-one, 81 mg (28% as a greenish grey solid: m.p. >400° C. (dec); $^1$H NMR (300 MHz, $d_6$-DMSO) δ 3.02 (m, 2H), 3.42 (m, 2H), 6.22 (m, 1H), 6.44 (m, 1H), 6.97 (m, 1H), 7.14 (t, J=7.5 Hz, 1H), 7.49 (dd, J=8.1, 0.9 Hz, 1H), 7.64 (dd, J=7.5, 0.6 Hz, 1H), 7.98 (br t, 1H), 11.01 (br s, 1H), 11.13 (br s, 1H). MS (electrospray, MH+) 252. Anal. ($C_{15}H_{13}N_3O$.0.4 $H_2O$) C, H, N.

Example EEEE 2-(4-Methylsulfanyl-phenyl)-1,3,4,5-tetrahydro-azepino[5,4,3-cd]indol-6-one

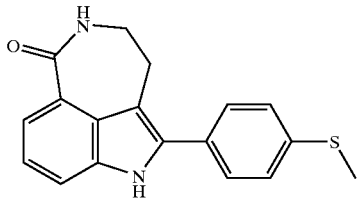

In a manner similar to that described for Compound 12, the tricyclic bormide (1.00 g, 3.77 mmol) and 4-thioanisole boronic acid (0.70 g, 4.15 mmol) were coupled to tield 2-(4-methylsulfanyl-phenyl)-1,3,4,5-tetrahydro-azepino[5,4,3-cd]indol-6-one, 416 mg (36%) as a beige solid: m.p. 250–251° C.; $^1$H NMR (300 MHz, d$_6$-DMSO) δ 2.54 (s, 3H), 3.03 (m, 2H), 3.39 (m, 2H), 7.20 (t, J=7.8 Hz, 1H), 7.41 (d, J=7.5, 0.9 Hz, 1H), 8.04 (br t, 1H), 11.52 (br s, 1H). MS (electrospray, MH+) 309. Anal. (C$_{13}$H$_{16}$N$_2$OS.0.6 H$_2$O) C, H, N.

Example FFFF 2-(4-Methanesulfinyl-phenyl)-1,3,4,5-tetrahydro-azepino[5,4,3-ed]indol-6-one

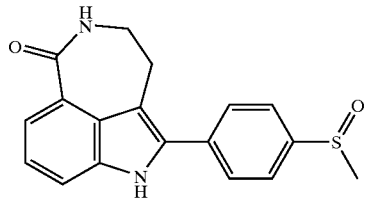

2-(4-methylsulfanyl-phenyl)-1,3,4,5-tetrahydro-azepino[5,4,3-cd]indol-6-one (100 mg, 0.32 mmol) was dissolved in 10 mL 1:1 MeOH:CH$_2$Cl$_2$. The solution was cooled to 0° C. and oxone (259 mg, 0.42 mmol) was added dropwise as a solution in 1.5 mL H$_2$O). The bright yellow reaction mixture was stirred at 0° C. for 15 min. Saturated Na$_2$S$_2$O$_{5(aq)}$ (4 mL) was added. The layers were separated and the aqueous layer extracted twice with 25% iPrPH/CHCl$_3$. The combined organic layers were dried (MgSO$_4$), concentrated in vacuo, and the two products (2-(4-methanesulfinyl-phenyl)-1,3,4,5-tetrahydro-azepino[5,4,3-cd]indol-6-one and 2-(4-methanesulfonyl-phenyl)-1,3,4,5-tetrahydro-azepino[5,4,3-cd]indol-6-one) separated by radial chromatography eluting with 5% MeOH/CHCl$_3$. Each was then crystallized from CH$_2$Cl$_2$/MeOH. 2-(4-Methanesulfinyl-phenyl)-1,3,4,5-tetrahydro-azepino[5,4,3-cd]indol-6-one, 39 mg (37%), was isolated as a white solid: m.p. 316–317° C. (dec); $^1$H NMR (300 MHz, d$_6$-DMSO) δ 2.81 (s, 3H), 3.09 (m, 2H), 3.40 (m, 2H), 7.25 (t, J=7.8 Hz, 1H), 7.59 (dd, J=8.1, 0.9 Hz, 1H), 7.71 (dd, J=7.5, 0.9 Hz, 1H), 7.84 (m, 4H), 8.08 (br t, 1H), 11.68 (br s, 1H). MS (electrospray, MH+) 325. Anal. (C$_{18}$H$_{16}$N$_2$O$_2$S) C, H, N, S.

Example GGGG 2-(4-Methanesulfonyl-phenyl)-1,3,4,5-tetrahydro-azepino[5,4,3-cd]indol-6-one

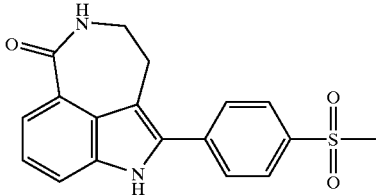

2-(4-methanesulfonyl-phenyl)-1,3,4,5-tetrahydro-azepino[5,4,3-cd]indol-6-one, 20 mg (18%) was isolated in the chromatography described above as a white solid: m.p. 308–309° C. (dec); $^1$H NMR (300 MHz, d$_6$-DMSO) δ 3.10 (m, 2H), 3.28 (s, 3H), 3.41 (m, 2H), 7.28 (t, J=7.8 Hz, 1H), 7.61 (dd, J=8.1, 0.6 Hz, 1H), 7.72 (dd, J=7.5, 0.6 Hz, 1H), 7.91 (d, J=8.4 Hz, 2H), 8.06 (d, J=8.4 Hz, 2H), 8.11 (br t, 1H), 11.77 (br s, 1H). MS (electrospray, MH+) 341. Anal. (C$_{18}$H$_{16}$N$_2$O$_3$S) C, H, N, S.

Example HHHH

2-Bromo-8-fluoro-1,3,4,5-tetrahydro-azepino[5,4,3-cd]indol-6-one

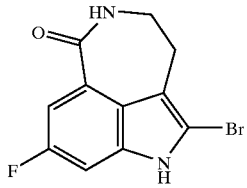

The title compound was prepared in a manner similar to that used for 2-bromo-1,3,4,5-tetrahydro-azepino[5,4,3-cd]indol-6-one, starting from 5-fluoro-2-methylbenzoic acid. 2-Bromo-8-fluoro-1,3,4,5-tetrahydro-azepino[5,4,3-cd]indol-6-one was isolated as an orange solid: m.p. 203–204° C. (dec); $^1$H NMR (300 MHz, d$_6$-DMSO) δ 2.79 (m, 2H), 3.41 (m, 2H), 7.29 (dd, J=8.7, 1.2 Hz, 1H), 7.74 (dd, J=10.8, 1.5 Hz, 1H), 8.23 (br t, 1H), 12.12 (br s, 1H). MS (electrospray, [M+Na]$^+$) 305/307.

8-Fluoro-2-(3-methylaminomethyl-phenyl)-1,3,4,5-tetrahydro-azepino[5,4,3-cd]indol-6-one

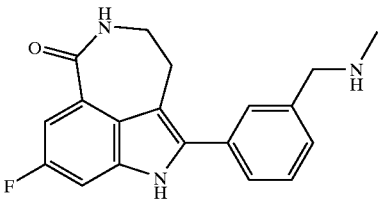

3-(8-fluoro-6-oxo-3,4,5,6-tetrahydro-1H-azepino[5,4,3-cd]indol-2-yl)-benzaldehyde (247 mg, 0.80 mmol; prepared in a manner similar to that described for compound 12 from 2-bromo-8-fluoro-1,3,4,5-tetrahydro-azepino[5,4,3-cd]indol-6-one and 3-formylphenylboronic acid) was reacted with methylamine (4.91 mmol) as described for Compound PPP to yield 8-fluoro-2-(3-methylaminomethyl-phenyl)-1,3,4,5-tetrahydro-azepino[5,4,3-cd]indol-6-one, 193 mg (74%) as an off-white solid: m.p. 270–272° C. (dec); $^1$H NMR (300 MHz, d$_6$-DMSO) δ 2.34 (s, 3H), 3.05 (m, 2H), 3.39 (m, 2H), 3.78 (s, 2H), 7.42 (m, 5H), 7.61 (br s, 1H), 8.26 (br t, 1H), 11.70 (br s, 1H). HRMS (MALDI, MH+) Calcd for C$_{19}$H$_{18}$N$_3$OF: 324.1512. Found: 324.1498. Anal. (C$_{19}$H$_{18}$N$_3$OF.1.5 H$_2$O.0.35 CHCl$_3$) C, H, N.

Example IIII

8-Fluoro-2-(4-methylaminomethyl-phenyl)-1,3,4,5-tetrahydro-azepino[5,4,3-cd]indol-6-one

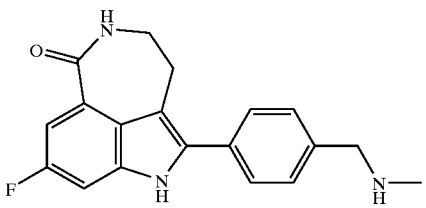

4-(8-fluoro-6-oxo-3,4,5,6-tetrahydro-1H-azepino[5,4,3-cd]indol-2-yl)-benzaldehyde (100 mg, 0.32 mmol; prepared in a manner similar to that described for compound 12 for 2-bromo-8-fluoro-1,3,4,5-tetrahydro-azepino[5,4,3-cd]indol-6-one and 4-formylphenylboronic acid) was reacted with methylamine (1.62 mmol) as described for Compound PPP to yield 8-fluoro-2-(4-methylaminomethyl-phenyl)-1,3,4,5-tetrahydro-azepino[5,4,3-cd]indol-6-one, 32 mg (31%) as a yellow solid: m.p. 1543–155° C.; $^1$H NMR (300 MHz, d$_6$-DMSO) δ 2.28 (s, 3H), 3.04 (m, 2H), 3.40 (m, 2H), 3.69 (s, 2H), 7.32 (dd, J=9.0, 2.4 Hz, 1H), 7.44 (m, 3H), 7.57 (d, J=8.1 Hz, 2H), 8.25 (br t, 1H), 11.67 (br s, 1H). HRMS (MALDI MH+) Calcd for C$_{19}$H$_{18}$N$_3$OF: 324,1512. Found: 325.1524. Anal. (C$_{19}$H$_{18}$N$_3$OF.0.3 H$_2$O) C, H, N.

Example JJJJ

8-Fluoro-2-(4-pyrrolidin-1-ylmethyl-phenyl)-1,3,4,5-tetrahydro-azepino[5,4,3-cd]indol-6-one

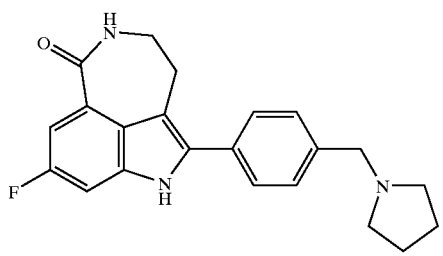

In a manner similar to that described for Compound PPP, 4-(8-fluoro-6-oxo-3,4,5,6-tetrahydro-1H-azepino[5,4,3-cd]indol-2-yl) benzaldehyde (100 mg, 0.32 mmol; prepared in a manner similar to that described for compound 12 from 2-bromo-8-fluoro-1,3,4,5-tetrahydro-azepino[5,4,3-cd]indol-6-one and 4-formylphenylboronic acid) was reacted with pyrrolidine (115 mg, 1.62 mmol) to yield 8-fluoro-2-(4-pyrrolidin-1-ylmethyl-phenyl)-1,3,4,5-tetrahydro-azepinop5,4,3-cd]indol-6-one, 16 mg (14%) as a yellow solid: m.p. 264–265° C. (dec), $^1$H NMR (300 MHz, d$_6$-DMSO) δ 1.72 (m, 4H), 2.49 (m, 4H), 3.04 (m, 2H), 3.39 (m, 2H), 3.64 (br s, 2H), 7.31 (dd, J=9.3, 2.4 Hz, 1H), 7.43 (m, 3H), 7.58 (d, J=8.1 Hz, 2H), 8.25 (br t, 1H), 11.66 (br s, 1H). HRMS (MALDI MH+) Calcd for C$_{22}$H$_{22}$N$_3$OF: 362.1825. Found: 364.1810. Anal. (C$_{22}$H$_{22}$N$_3$OF.0.5 H$_2$O) C, H, N.

Example KKKK

6-Oxo-1,3,4,5-tetrahydro-1H-azepino[5,4,3-cd]indole-2-carboxylic acid phenylamide

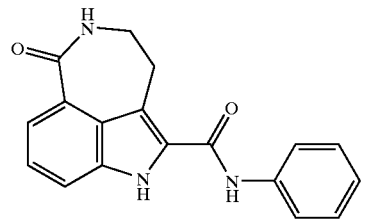

In a manner similar to that described for Compound YYY, 6-oxo-3,4,5,6-tetrahydro-1H-azepino[5,4,3-cd]indole-2-carboxylic acid (60 mg, 0.26 mmol) was coupled with aniline (27 mg, 0.29 mmol) to yield 6-oxo-1,3,4,5-tetrahydro-1H-azepino[5,4,3-cd]indole-2-carboxylic acid phenylamide as a white solid: m.p. 320–322° C. (dec); $^1$H NMR (300 MHz, d$_6$-DMSO) δ 3.28 (m, 2H), 3.42 (m, 2H), 7.11 (app t, J=7.5 Hz, 1H), 7.37 (m, 3H), 7.64 (d, J=8.1 Hz, 1H), 7.74 (m, 3H), 8.15 (br t, 1H), 9.98 (br s, 1H), 11.78 (br s, 1H). MS (electrospray, MH+) 306. Anal. (C$_{18}$H$_{15}$N$_3$O$_2$.0.25 H$_2$O) C, H, N.

Example LLLL

6-Oxo-1,3,4,5-tetrahydro-1H-azepino[5,4,3-cd]indole-2-carboxylic acid (4-chloro-phenyl)-amide

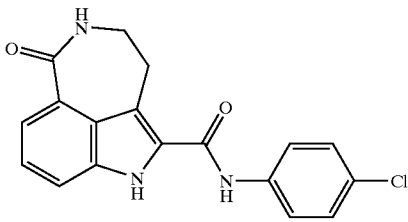

In a manner similar to that described for Compound YYY, 6-oxo-3,4,5,6-tetrahydro-1H-azepino[5,4,3-cd]indole-2-carboxylic acid (60 mg, 0.26 mmol) was coupled with 4-chloroaniline (37 mg, 0.29 mmol) to yield 6-oxo-1,3,4,5-tetrahydro-1H-azepino[5,4,3-cd]indole-2-carboxylic acid (4-chloro-phenyl)-amide as a white solid: $^1$H NMR (300 MHz, d$_6$-DMSO) δ 3.26 (m, 2H), 3.42 (m, 2H), 7.36 (app t, J=7.8 Hz, 1H), 7.44 (d, J=8.7 Hz, 2H), 7.65 (d, J=8.1 Hz, 1H), 7.76 (m, 3H), 8.16 (br t, 1H), 10.12 (br s, 1H), 11.79 (br s, 1H). MS (electrospray, MH+) 340. Anal. (C$_{18}$H$_{14}$ClN$_3$O$_2$) C, H. N.

Example MMMM

6-Oxo-1,3,4,5-tetrahydro-1H-azepino[5,4,3-cd]
indole-2-carboxylic acid naphthalen-2-ylamide

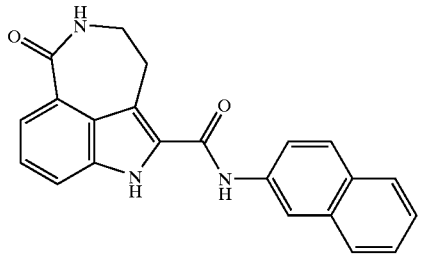

In a manner similar to that described for Compound YYY, 6-oxo-3,4,5,6-tetrahydro-1H-zepino[5,4,3-cd]indole-2-carboxylic acid (60 mg, 0.26 mmol) was coupled with 2-naphthylamine (41 mg, 0.29 mmol) to yield 6-oxo-1,3,4,5-tetrahydro-1H-azepino[5,4,3-cd]indole-2-carboxylic acid naphthalen-2-ylamide as a white solid: $^1$H NMR (300 MHz, $d_6$-DMSO) δ 3.33 (m, 2H), 3.45 (m, 2H), 7.38 (app t, J=7.8 Hz, 1H), 7.47 (m, 2H), 7.68 (d, J=8.1 Hz, 1H), 7.78 (m, 2H), 7.91 (m, 3H), 8.19 (br t, 1H), 8.43 (br s, 1H), 10.21 (br s, 1H), 11.84 (br s, 1H). MS (electrospray, MH+__356. Anal. ($C_{22}H_{17}N_3O_2$.0.7 $H_2O$) C, H, N.

Example NNNN

6-Oxo-1,3,4,5-tetrahydro-1H-azepino[5,4,3-cd]
indole-2-carboxylic acid naphthalen-1-ylamide

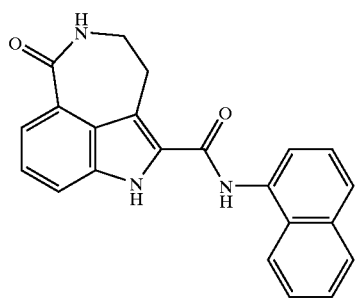

In a manner similar to that described for Compound YYY, 6-oxo-3,4,5,6-tetrahydro-1H-azepino[5,4,3-cd]indole-2-carboxylic acid (60 mg, 0.26 mmol) was coupled with 1-naphthylamine (41 mg, 0.29 mmol) to yield 6-oxo-1,3,4,5-tetrahydro-1H-azepino[5,4,3-cd]indole-2-carboxylic acid naphthalen-1-ylamide as a white solid: m.p. 330–332° C. (dec); $^1$H NMR (300 MHz, $d_6$-DMSO) δ 3.33 (m, 2H), 3.48 (m, 2H), 7.38 (app t, J=7.8 Hz, 1H), 7.57 (m, 3H), 7.68 (d, J=7.8 Hz, 1H), 7.77 (m, 2H), 7.87 (d, J=7.8 Hz, 1H), 7.99 (m, 1H), 8.13 (m, 2H), 10.06 (br s, 1H), 11.87 (br s, 1H). MS (electrospray, MH+) 356. Anal. ($C_{22}H_{17}N_3O_2$.0.5 $H_2O$) C, H, N.

Example OOOO

6-Oxo-1,3,4,5-tetrahydro-1H-azepino[5,4,3-cd]
indole-2-carboxylic acid prop-2-ynylamide

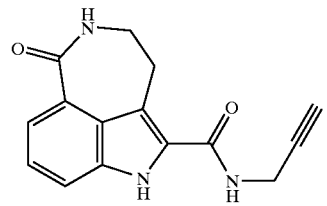

In a manner similar to that described for Compound YYY, 6-oxo-3,4,5,6-tetrahydro-1H-azepino[5,4,3-cd]indole-2-carboxylic acid (60 mg, 0.26 mmol) was coupled with propargylamine (16 mg, 0.29 mmol) to yield 6-oxo-1,3,4,5-tetrahydro-1H-azepino[5,4,3-cd]indole-2-carboxylic acid prop-2-ynylamide as a white solid: m.p. 191–192° C.; $^1$H NMR (300 MHz, $d_6$-DMSO) δ 3.19 (m, 3H), 3.39 (m, 2H), 4,10 (m, 2H), 7.32 (app t, J=7.8 Hz, 1H), 7.59 (d, J=8.1 Hz, 1H), 7.72 (d, J=7.2 Hz, 1H), 8.12 (br t, 1H), 8.43 (br t, 1H), 11.60 (br s, 1H). MS (electrospray, MH+) 268. Anal. ($C_{15}H_{13}N_3O_2$.2$H_2O$) C, H, N.

Example PPPP

6-Oxo-1,3,4,5-tetrahydro-1H-azepino[5,4,3-cd]
indole-2-carboxylic acid isopropyl-amide

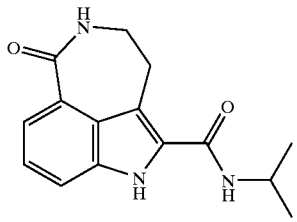

In a manner similar to that described for Compound YYY, 6-oxo-3,4,5,6-tetrahydro-1H-azepino[5,4,3-cd]indole-2-carboxylic acid (60 mg, 0.26 mmol) was coupled with isopropylamine (17 mg, 0.29 mmol) to yield 6-oxo-1,3,4,5-tetrahydro-1H-azepino[5,4,3-cd]indole-2-carboxylic acid isopropylamide as a white solid: m.p. 261–262° C. (dec); $^1$H NMR (300 MHz, $d_6$-DMSO) δ 1.20 (d, J=6.6 Hz, 1H) 3.22 (m, 2H), 3.38 (m, 2H), 4.90 (m, 1H), 7.32 (app t, J=7.8 Hz, 1H), 7.59 (d, J=8.1 Hz, 1H), 7.71 (d, J=7.2 Hz, 1H), 7.81 (d, J=7.5 Hz, 1H), 8.10 (br t, 1H), 11.53 (br s, 1H). MS (electrospray, MH+) 272. Anal. ($C_{15}H_{17}N_3O_2$.0.2$H_2O$) C, H, N.

Example QQQQ

6-Oxo-1,3,4,5-tetrahydro-1H-azepino[5,4,3-cd]
indole-2-carboxylic acid cyclopropylamide

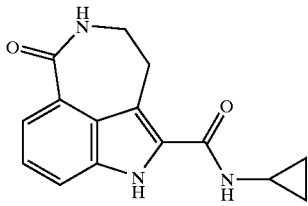

In a manner similar to that described for Compound YYY, 6-oxo-3,4,5,6-tetrahydro-1H-azepino[5,4,3-cd]indole-2-carboxylic acid (60 mg, 0.26 mmol) was coupled with cyclopropylamine (17 mg, 0.29 mmol) to yield 6-oxo-1,3,4,5-tetrahydro-1H-azepino[5,4,3-cd]indole-2-carboxylic acid cyclopropyleamide as a white solid: m.p 249–251° C.; $^1$H NMR (300 MHz, $d_6$-DMSO) δ 0.56 (m, 2H), 0.75 (m, 2H), 2.95 (m, 2H), 3.37 (m, 2H), 3.61 (m, 1H), 7.30 (app t, J=7.5 Hz, 1H), 7.58 (d, J=8.1 Hz, 1H), 7.70 (d, J=7.2 Hz, 1H), 8.09 (m, 2H), 11.48 (br s, 1H). MS (electrospray, MH+270. Anal. ($C_{15}H_{15}N_3O_2$·1H$_2$O) C, H, N.

Example RRRR (rac)-3-(4-Methoxyphenyl)-3,4,5,6-tetrahydro-1H-
azepino[5,4,3-cd]indol-6-one

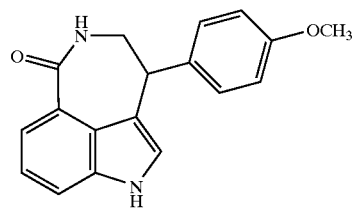

In a manner similar to that described for the preparation of Example Q, methyl indole-4-carboxylate and p-methoxy nitrostyrene were condensed and the resulting nitro alkane was reduced/cyclized to give, after recrystallization (CH$_2$Cl$_2$/MeOH/hexanes), (rac)-3-(4-methoxyphenyl)-3,4,5,6-tetrahydro-1H-axepino[5,4,3-cd]indol-6-one, 16.9 mh (50%) as a white solid: m.p. 221–223° C.; $^1$H NMR (300 MHz, $d_4$-MeOH) δ 3.57 (br m, 5H), 5.15 (br s, 1H) 6.62 (m, 2H), 6.86 (m, 2H), 7.08 (app t, J=7.8 Hz, 1H), 7.11 (s, 1H), 7.37 (d, J=7.9 Hz, 1H), 7.73 (d, J=7.5 Hz, 1H). Anal. ($C_{19}H_{16}N_2O_2$·0.25 H$_2$O) C, H, N.

Example SSSS 2-(3-Morpholin-4-ylmethylphenyl)-3,4,5,6-
tetrahydro-1H-azepino[5,4,3-cd]indol-6-one

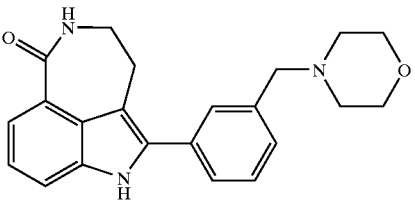

In a manner similar to that described for Compound 22, the aldehyde 15 (29 mg, 0.1 mmol) in MeOH (1 mL) was treated with morpholine (0.04 mL, 0.5 mmol) and a solution of sodium cyanoborohydride (0.15 mmol) and zinc chloride (0.08 mmol) in MeOH (1 mL) to give, after radial chromatography (5% MeOH in CHCl$_3$), 2-(3-morpholin-4-ylmethylphenyl)-3,4,5,6-tetrahydro-1H-azepinop5,4,3-cd]indol-6-one, 35 mg (99%) as sticky white solid: $^1$H NMR (300 MHz, $d_6$-DMSO) δ 2.37 (m, 4H), 3.02 (m, 2H), 3.35 (m, 2H), 3.51 (m, 6H), 7.17 (app t, J=7.7 Hz, 1H), 7.30 (br d, 1H), 7.52 (m, 4H), 7.64 (d, J=7.5 Hz, 1H), 8.03 (br t, 1H), 11.53 (br s, 1H). HRMS (FAB, MH+) Calcd for $C_{22}H_{24}N_3O_2$: 362.1869. Found: 362.1866.

Compound TTT 2-(3-Pyrrolidin-1-ylmethylphenyl)-3,4,5,6-tetrahydro-1H-
azepino[5,4,3-cd]indol-6-one

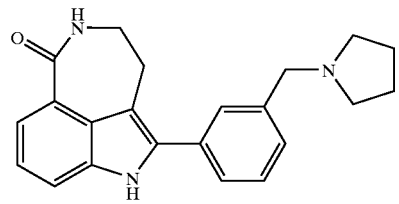

In a manner similar to that described for Compound 22, the aldehyde 15 (200 mg, 0.69 mmol) in MeOH (10 mL) was treated with pyrrolidine (0.34 mL, 4.14 mmol) and a solution of sodium cyanoborohydride (0.76 mmol) and zinc chloride (0.38 mmol) in MeOH (1.4 mL) to give, after crystallization (CH2Cl2/MeOH/hexanes), 2-(3-pyrrolidin-1-ylmethylphenyl)-3,4,5,6-tetrahydro-1H-azepino[5,4,3-cd]indol-6-one, 139 mg (58%) as pale yellow solid: m.p. 219–223° C. (dec); $^1$H NMR (300 MHz, $d_6$-DMSO) δ 1.73 (m, 4H), 2.49 (m, 4H), 3.06 (m, 2H), 3.40 (m, 2H), 3.69 (s, 2H), 7.22 (t, J=7.7 Hz, 1H), 7.34 (br d, 1H), 7.53 (m, 4H), 7.68 (dd, J=7.7, 0.8 Hz, 1H), 8.08 (br t, 1H), 11.59 (br s, 1H). HRMS (FAB, MH+) Calcd for $C_{22}H_{24}N_3O$: 346,1919. Found: 346.1910. Anal. ($C_{23}H_{25}N_3O$·0.6 H$_2$O) C, H, N.

Example UUUU 2-(4-Pyrrolidin-1-ylmethylphenyl)-3,4,5,6-tetrahydro-1H-azepino[5,4,3-cd]indol-6-one

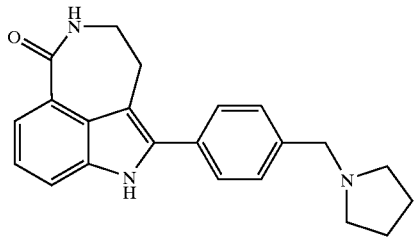

In a manner similar that described for Compound 22, the para-aldehyde (150 mg, 0.52 mmol) in MeOH (10 mL) was treated with pyrrolidine (0.26 mL, 3.10 mmol) and a solution of sodium cyanoborohydride (0.57 mmol) and zinc chloride (0.28 mmol) in MeOH (1.1. mL) to give, after crystallization ($CH_2Cl_2$/MeOH/hexanes), 2-(4-pyrrolidin-1-ylmethylphenyl)-3,4,5,6-tetrahydro-1H-azepino[5,4,3-cd]indol-6-one, 141 mg (79%) as pale yellow solid: m.p. 221–225° C. (dec); $^1$H NMR (300 MHz, $d_6$-DMSO) δ 1.71 (m, 4H), 2.46 (m, 4H), 3.06 (m, 2H), 3.41 (m, 2H), 3.41 (m, 2H), 3.63 (s, 2H), 7.21 (t, J=7.8 Hz, 2H), 7.45 (d of Abq, J=8.2 Hz, 2H), 7.55 (dd, J=7.9, 0.9 Hz, 1H), 7.59 (d of Abq, J=8.2 Hz, 2H), 7.68 (br d, 1H), 8.07 (br t, 1H), 11.54 (br s, 1H). HRMS (FAB, MH+) Calcd for $C_{22}H_{24}N_3O$: 346.1919. Found: 346.1911. Anal. ($C_{23}H_{25}N_3O.0.5\ H_2O$) C, H, N.

Example VVVV 2-(4-Morpholin-4-ylmethylphenyl)-3,4,5,6-tetrahydro-1H-azepino[5,4,3-cd]indol-6-one

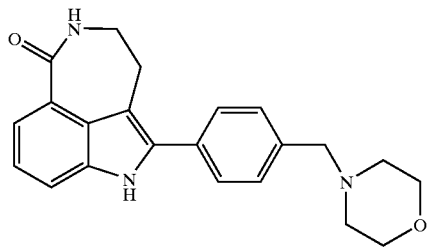

In a manner similar to that described for Compound 22, the para-aldehyde (264 mg, 0.91 mmol) in MeOH (10 mL) was treated with morpholine (0.40 mL, 4.55 mmol) and a solution of sodium cyanoborohydride (1.36 mmol) and zinc chloride (0.68 mmol) in MeOH (2.0 mL) to give, after recrystallization ($CH_2Cl_2$/MeOH/hexanes) and radial chromatography, 2-(4-morpholin-4-ylmethylphenyl)-3,4,5,6-tetrahydro-1H-azepino[5,4,3-cd]indol-6-one, 44.8 mg (14%) as solid: $^1$H NMR (300 MHz, $d_6$-DMSO) δ 2.39 (m, 4H), 3.06 (m, 2H), 3.41 (m, 2H), 3.53 (s, 2H), 3.59 (m, 4H), 7.21 (br t, 1H), 7.46 (d of Abq, J=8.0 Hz, 2H), 7.55 (br d, 1H), 7.62 (d of Abq, J=8.0 Hz, 2H), 7.68 (br d, 1H, 8.07 (br t, 1H), 11.55 (br s, 1H). HRMS (FAB, MH+) Calcd for $C_{22}H_{24}N_3O_2$: 362.1869. Found: 362.1861.

Example WWWW 2-(4-Hydroxymethylphenyl)-3,4,5,6-tetrahydro-1H-azepino[5,4,3-cd]indol-6-one

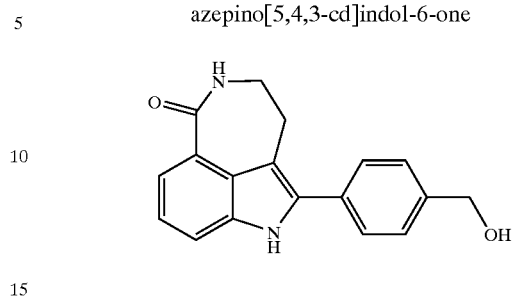

The title compound was isolated as a reduction by-product from the reductive amination of the para-paldehyde with morpholine and sodium cyanoborohydride, and recrystallized ($CH_2Cl_2$/MeOH/hexanes) to give 2-(4-hydroxymethylphenyl)-3,4,5,6-tetrahydro-1H-azepino[5,4,3-cd]indol-6-one, 64 mg (24%) as a white solid: $^1$H NMR (300 MHz, $d_6$-DMSO) δ 3.05 (m, 2H), 3.39 (m, 2H), 4.57 (d, J=5.6 Hz, 2H), 5.27 (t, J=5.6 Hz, —OH), 7.21 (br t, 1H), 7.47 (d of Abq, J=7.9 Hz, 2H), 7.55 (br d, 1H), 7.62 (d of Abq, J=7/9 Hz, 2H), 7.68 (br d, 1H), 8.07 (br t, 1H), 11.55 (s, 1H). Anal. ($C_{18}H_{16}N_2O_2.0.9\ H_2O$) C, H, N.

Example XXXX 2-(4-(N,N-Dimethylamino)methylphenyl)-3,4,5,6-tetrahydro-1H-azepino[5,4,3-cd]indol-6-one, N-oxide

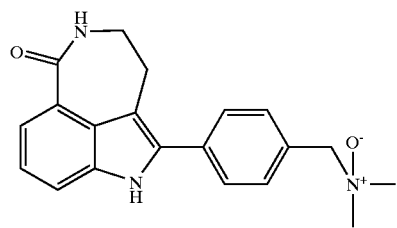

A solution of Compound 21 (58 mg) in acetone (7.0 mL) was treated with 30% aqueous hydrogen peroxide (0.6 mL) at room temperature and the yellow solution was allowed to stir for three days. The acetone was removed in vacuo and the residue was taken-up in isopropyl alcohol. A solid was precipitated with the addition of an equal volume of cold hexanes and collected by a quick filtration. Precautions were taken to prevent the solid from absorbing moisture from the atmosphere. The solid was recrystallized (isopropanol/acetone/$CH_2Cl_2$/hexanes) to give 2-(4-(N,N-dimethylamino)methylphenyl)-3,4,5,6-tetrahydro-1H-azepino[5,4,3-ced]indol-6-one, N-oxide, 37 mg (60%) as a pale yellow solid: $^1$H NMR (300 MHz, $d_6$-DMSO) δ 3.22 (s, 6H), 3.56 (br m, 4H), 4.63 (s, 2H), 7.40 (br t, 1H), 7.76 (br d, 1H), 7.87 (m, 5H), 8.29 (br t, 1H), 12.00 (br s, 1H). HRMS (FAB, MH$^+$—H2O) Calcd for $C_{20}H_{20}N_3O$: 318.1606. Found: 318.1606. Anal. ($C_{20}H_{21}N_3O_2.3.5\ H_2O$) C, H, N.

Example YYYY 1,5-Dihydro-3-(4-trifluoromethylphenyl-[1,2]diazepino[4,5,6-cd]-indol-6-one

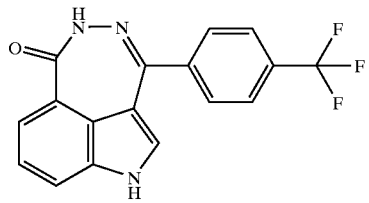

In a manner similar to that described for Compound 28, a solution of methyl indole-4-carboxylate (250 mg, 1.43 mmol) in dichloroethane (3 mL) was treated with p-trifluoromethylbenzoyl chloride (445 mg, 2.14 mmol) and aluminum chloride (572 mg). The intermediate ketone (95 mg, 0.27 mmol) in MeOH (3 mL) and conc. HCl (0.05 mL) was treatewd, as described, with hydrazine hydrate (0.1 mL). The reaction was quenched at 0° C. with w M NaOAc and the aqueous layer was adjusted to pH=8 with 1 M NaOH. The product was isolated by extraction with $CH_2Cl_2$, and recrystallized ($CH_2Cl_2$/hexanes) to give 1,5-dihydro-3-(4-trifluoromethylphenyl-[1,2]diazepino[4,5,6-cd]indol-6-one, 30 mg (34%) as a yellow solid: $^1$H NMR (300 MHz, $d_6$-DMSO) δ 7.24 (app br t, 1H), 7.29 (d, J=2.8 Hz, 2H), 7.60 (m, 2H), 7.82 (m, 4H), 10.57 (s, 1H), 12.01 (s, 1H). HRMS (FAB, Mna$^+$) Calcd for $C_{11}H_{10}N_3Ona$: 352.0674. Found: 352.0668.

Example ZZZZ 1,5-Dihydro-3-pentafluoroethyl-[1,2]diazepino[4,5,6-cd]-indol-6-one

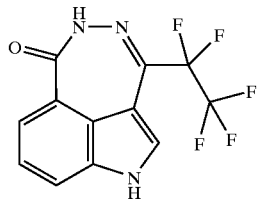

In a manner similar to that described for Compound 28, a solution of methyl indole-4-carboxylate (351 mg, 2.01 mmol) in dichloroethane (7 mL) was treated with pentafluoropropionyl chloride (2.51 mmol) and aluminum chloride (575 mg). The intermediate ketone (50 mg, 0.16 mmol) in MeOH (2 mL) and conc. HCl (0.02 mL) was treated, as described, with hydrazine hydrate (0.1 mL). The reaction was quenched at 0° C. with 1 M NaOAc and the aqueous layer was adjusted to pH=8 with 1 M NaOH. The product was isolated by extraction with $CH_2Cl_2$, and recrystallized ($CH_2Cl_2$/MeOH/hexanes) to give 1,5-dihydro-3-pentafluoroethyl-[1,2]diazepino[4,5,6-cd]-indol-6-one, 15 mg (28%) as a yellow solid: $^1$H NMR (300 MHz, $d_6$-DMSO) δ 7.16 (app br t, 1H), 7.54 (m, 2H), 7.65 (m, 1H), 10.87 (s, 1H), 12.15 (s, 1H). HRMS (FAB, Mna$^+$) Calcd for $C_{11}H_{10}N_3Ona$: 352.0674. Found: 352.0668.

PARP Enzyme Inhibition Assay:

The PARP enzyme-inhibiting activities of the compounds of the invention were assayed as described by Simonin et al. (*J. Biol. Chem.* (1993), 268:8529–8535) and Marsischky et al. (*J. Biol. Chem.* (1995), 270:3247–3254) with minor modifications as follows. Samples (50 μL) containing 20 nM purified PARP protein, 10 μg/mL DNAse I-activated calf thymus DNA (sigma), 500 μM NAD$^+$, 0.5 μCi [$^{32}$P]NAD$^+$, 2% DMSO, and various concentrations of test compounds were incubated in sample buffer (50 mM Tris pH 8.0, 10 mM $MgCl_2$, 1 mM tris(carboxyethyl)phosphine HCl) at 25° C. for 5 minutes. Under these conditions, the reaction rate was linear for times up to 10 minutes. The reaction was stopped by the addition of an equal volume of ice-cold 40% trichloroacetic acid to the samples, which were then incubated on ice for 15 minutes. The samples were then transferred to a Bio-Dot microfiltration apparatus (BioRad), filtered through Whatman GF/C glass-fiber filter paper, washed 3 times with 150 μL of wash buffer (5% trichloroacetic acid, 1% inorganic pyrophosphate), and dried. [$^{32}$P]ADP-Ribose incorporation into the acid-insoluble material was quantitated using a PhosphorImager (Molecular Dynamics) and ImageQuant software. Inhibition constants ($K_i$) were calculated by non-linear regression analyses using the velocity equation for competitive inhibition (Segel, *Enzyme Kinetics: Behavior and Analysis of Rapid Equilibrium and Steady-State Enzyme Systems*, John Wiley & Sons, Inc., New York (1975), 100–125). In the case of tight-binding inhibitors, 5 nM enzyme was used and the reaction was incubated at 25° C. for 25 minutes. $K_i$ values for tight-binding inhibitors were calculated using the equation described by Sculley et al. (*Biochim. Biophys. Acta* (1986), 874:44–53).

Cytotoxicity Potentiation Assay:

A549 cells (ATCC, Rockville, Md.) were seeded into 96-well cell culture plates (Falcon brand, Fisher Scientific, Pittsburgh, Pa.) 16 to 24 hours before experimental manipulation. Cells were then treated with a test compound (or a combination of test compounds where indicated) for either 3 days or 5 days, at a concentration of 0.4 μm. At the end of treatments, relative cell number was determined either by MTT assay or SRB assay. For the MTT assay, 0.2 μg/μl of MTT (3-(4,5-dimethylthiazol-2-yl)-2,5-diphenyltetrazolium bromide, Sigma Chemical Co., St. Louis, Mo.) was added to each well of a plate, and the plate was incubated in a cell-culture incubator for 4 hours. Metabolized MTT in each well was solubilized in 150 μl of DMSO (Sigma Chemical Co.) with shaking and quantified with a Wallac 1420 Victor plate reader (EG&G Wallac, Gaithersburg, Md.) at 540 nm. For the SRB assay, cells were fixed with 10% trichloroacetic acid (Sigma Chemical Co) for an hour at 4° C. After extensively washing, fixed cells were stained for 30 minutes with 0.4% sulforhodamine B (SRB, Sigma Chemical Co.) in 1% acetic acid (Sigma Chemical Co). Unbound SRB was washed away with 1% acetic acid. Then the cultures were air-dried, and bound dye was solubilized with 10 mM unbuffered Tris base (Sigma Chemical Co) with shaking. The bound dye was measured photometrically with the Wallac Victor plate reader at 515 nm. The ratio of the OD (optical density) value of a compound-treated culture to the OD value of a mock-treated culture, expressed in percentage, was used to quantify the cytotoxicity of a compound. The concentration at which a compound causes 50% cytotoxicity is referred to as $IC_{50}$. To quantify the potentiation of the cytotoxicity of topotecan or temozolomide by test compounds, a dimensionless parameter $PF_{50}$ is used and is defined as the ratio of the $IC_{50}$ of topotecan or temozolomide alone to the $IC_{50}$ of topotecan or temozolomide in combination with a test compound. For the compounds of the invention, $PF_{50}$ values were determined by testing with topotecan.

Inhibition constants ($K_i$ values) and cytotoxicity potentiation parameters ($PF_{50}$ values) as determined for exemplary compounds of the invention are presented in Table 1 below. If there are two $K_i$ values for a single compound, it means that the compound $K_i$ was tested twice.

TABLE 1

PARP Enzyme Inhibition and Cytotoxicity Potentiation

| Compound No. | Inhibition Constant $K_i$ (nM) | Cytotoxicity Potentiation $PF_{50}$ |
|---|---|---|
|  | 69 | 1.1 |
| 3 | 2.8 | N.D. |
| 6 | 0.7, 1 | 2.2 |
| 10 | 38 | N.D. |
| 12 | 4.2 | 1.8 |
| 13 | 6.2, 4.5 | N.D. |
| 14 | 1.4 | N.D. |
| 16 | 5.0 | 1.9 |
| 17 | 6.5 | N.D. |
| 18 | >>1,000 | N.D. |
| 19 | 62 | N.D. |
| 20 | 45 | N.D. |
| 21 | 5.0 | 2.4 |
| 22 | 7.2 | 2.3 |
| 23 | 4.8, 3.1 | 2.3 |
| 24 | 57 | N.D. |
| 25 | 4.0 | N.D. |
| 26 | 22, 18 | N.D. |
| 27 | 3.4 | 1.3 |
| 28 | 4, 3.8 | 1 |
| 29 | 8 | 1 |
| 30 | 6.3 | 2.4 |
| 31 | 5 | N.D. |
| 32 | 11.3 | N.D. |
| 33 | 230 | N.D. |
| 34 | 3.9 | N.D. |
| 35 | 3.8, 5.8 | N.D. |
| 36 | 29 | N.D. |
| 37 | 24 | N.D. |
| 38 | 8.4 | N.D. |
| 39 | 4.8 | N.D. |
| 40 | 5.2 | N.D. |
| 41 | 5.1 | N.D. |
| 42 | 5.1 | N.D. |
| 11 | 7.3 | N.D. |
| 43 | 2.6 | N.D. |
| OO | 4.1 | 2.4 |
| PP | 5.3 | 2.3 |
| QQ | 5.5, 4.5 | N.D. |
| RR | 6.9 | N.D. |
| SS | 14 | N.D. |
| TT | 12.2, 4.2 | N.D. |
| UU | 10 | 1.8 |
| VV | 10 | 2.0 |
| WW | 4.4 | N.D. |
| XX | 4.6 | N.D. |
| YY | 15.1 | N.D. |
| ZZ | 9.7 | N.D. |
| AAA | 11.4 | N.D. |
| BBB | 20 | N.D. |
| CCC | 7.3 | N.D. |
| DDD | 23 | N.D. |
| EEE | 10.6 | N.D. |
| FFF | 125 | N.D. |
| GGG | 4.1 | 1.9 |
| HHH | 6.6 | N.D. |
| III | 40 | N.D. |
| JJJ | 5.3 | N.D. |
| KKK | 222 | N.D. |
| LLL | 32 | N.D. |
| MMM | 9.4 | 2.3 |
| NNN | 172 | N.D. |
| OOO | 14 | N.D. |
| PPP | 9.4 | 2.1 |
| QQQ | 10.2 | 2.3 |
| RRR | 23 | N.D. |
| SSS | 66 | N.D. |
| TTT | 26 | N.D. |
| UUU | 11.4 | N.D. |
| VVV | 9.1 | N.D. |

TABLE 1-continued

PARP Enzyme Inhibition and Cytotoxicity Potentiation

| Compound No. | Inhibition Constant $K_i$ (nM) | Cytotoxicity Potentiation $PF_{50}$ |
|---|---|---|
| WWW | 263 | N.D. |
| XXX | 370 | N.D. |
| YYY | 6.3 | 1.5 |
| ZZZ | 0.7 | N.D. |
| AAAA | 1.1 | N.D. |
| BBBB | 4.8 | N.D. |
| CCCC | 4.8 | N.D. |
| DDDD | 7.7 | N.D. |
| EEEE | 2.9 | N.D. |
| FFFF | 4.7 | N.D. |
| GGGG | 6.2 | N.D. |
| HHHH | 2.2 | 1.9 |
| IIII | 1.4 | 2.6 |
| JJJJ | 4.4 | 2.4 |
| KKKK | 9.6 | N.D. |
| LLLL | 8.6 | N.D. |
| MMMM | 16 | N.D. |
| NNNN | 10 | N.D. |
| OOOO | 13 | N.D. |
| PPPP | 32 | N.D. |
| QQQQ | 21 | N.D. |
| RRRR | 61 | N.D. |
| SSSS | 19 | N.D. |
| TTTT | 7.4 | 1.6 |
| UUUU | 5.6 | 2.0 |
| VVVV | 13.2 | 2.1 |
| WWWW | 5.7 | N.D. |
| XXXX | 18 | 1.7 |
| YYYY | 9 | N.D. |
| ZZZZ | 40 | N.D. |

Note
N.D. = not determined.

While the invention has been described by reference to preferred embodiments and specific examples, those skilled in the art will recognize that various changes and modifications can be made without departing from the spirit and scope of the invention. Thus, the invention should be understood as not being limited by the foregoing detailed description, but as being defined by the appended claims and their equivalents.

What is claimed is:

1. A method of preparing a compound of formula I

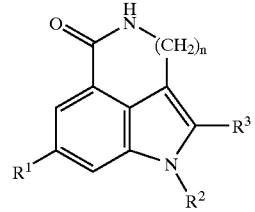

wherein $R^1$ is hydrogen or halogen;

$R^2$ is hydrogen or methyl;

$R^3$ is:
optionally substituted aryl, alkyl, alkenyl, alkynyl, cycloalkyl, heterocycloalkyl, heteroaryl; or
—C(O)OR$^7$, wherein $R^7$ is optionally substituted alkyl;

n is 1 or 2;

the method comprising:

a) converting a compound of formula II, wherein $R^4$ is —(CH$_2$)$_n$NH$_2$; $R^5$ is —CO$_2$CH$_3$

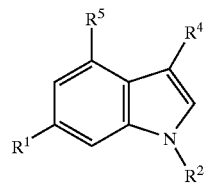

into a compound of formula III

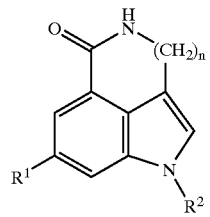

b) converting the compound of formula III into a compound of formula IV, wherein X is bromine or iodine; and

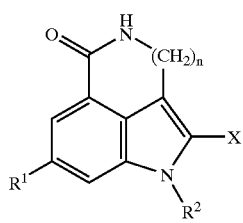

c) transforming the compound of formula IV into the compound of formula I.

2. The method of claim 1, wherein the compound of formula II is formed by reduction of a compound of formula V, wherein $R^6$ is —CH=NOH or —CH=CHNO$_2$.

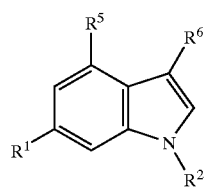

3. The method of claim 2, wherein the compound of formula V is formed by transformation of the compound of formula VI.

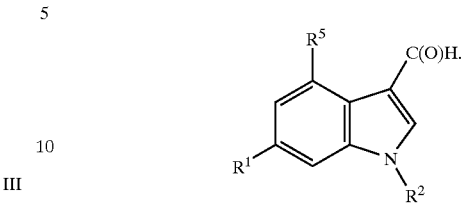

4. The method of claim 3, wherein the compound of formula VI is formed by Vilsmeier formylation or Friedel-Crafts acylation of the compound of formula VII.

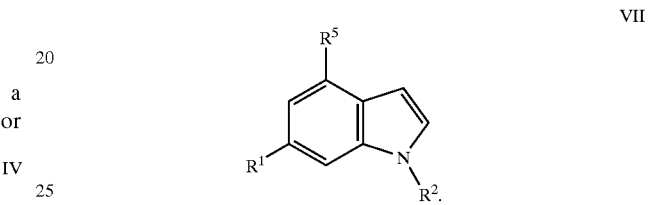

5. The method of claim 1, wherein the step b) comprises treating the compound of formula III with pyridinium tribromide to form the compound of formula IV.

6. The method of claim 1, wherein the step c) comprises reacting the compound of formula IV with $R^3B(OH)_2$ in the presence of tetrakis(triphenylphosphine)palladium to form the compound of formula I, wherein $R^3$ is optionally substituted aryl, alkyl, alkenyl, alkynyl, cycloalkyl, heterocycloalkyl, heteroaryl.

7. The method of claim 1 further comprising reacting the compound of formula I, wherein $R^1$ is fluorine, $R^2$ is hydrogen, $R^3$ is -Ph-CHO, n is 2, with methylamine to form the compound of formula I, wherein $R^1$ is fluorine, $R^2$ is hydrogen, $R^3$ is -Ph-CH$_2$—NCH$_3$.

8. The method of claim 1, wherein the step c) comprises reacting the compound of formula IV with Pd/CO/R$^7$OH, wherein $R^7$ is optionally substituted alkyl, to form the compound of formula I, wherein $R^3$ is —C(O)OR$^7$.

* * * * *